US011246963B2

(12) United States Patent
Slager et al.

(10) Patent No.: US 11,246,963 B2
(45) Date of Patent: *Feb. 15, 2022

(54) COMPOSITIONS AND METHODS FOR DELIVERY OF HYDROPHOBIC ACTIVE AGENTS

(71) Applicant: SurModics, Inc., Eden Prairie, MN (US)

(72) Inventors: Joram Slager, St. Louis Park, MN (US); Dale G. Swan, St. Louis Park, MN (US); Darin DuMez, Minneapolis, MN (US); Joseph Ventura, Elk Grove, CA (US); Shannon Wadman, Minneapolis, MN (US); Joseph Schmidt McGonigle, Minneapolis, MN (US); Robert W. Hergenrother, Eden Prairie, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/280,170

(22) Filed: May 16, 2014

(65) Prior Publication Data

US 2014/0336571 A1 Nov. 13, 2014

Related U.S. Application Data

(63) Continuation-in-part of application No. 14/072,520, filed on Nov. 5, 2013, now Pat. No. 9,555,119.

(60) Provisional application No. 61/722,735, filed on Nov. 5, 2012, provisional application No. 61/740,713, filed on Dec. 21, 2012, provisional application No. 61/824,160, filed on May 16, 2013.

(51) Int. Cl.
| | | |
|---|---|---|
| *A61K 47/32* | (2006.01) | |
| *A61L 29/04* | (2006.01) | |
| *A61L 29/08* | (2006.01) | |
| *A61K 31/337* | (2006.01) | |
| *A61K 31/436* | (2006.01) | |
| *A61M 25/10* | (2013.01) | |
| *A61L 29/16* | (2006.01) | |
| *A61K 47/34* | (2017.01) | |
| *A61K 9/00* | (2006.01) | |

(52) U.S. Cl.
CPC .......... *A61L 29/041* (2013.01); *A61K 31/337* (2013.01); *A61K 31/436* (2013.01); *A61K 47/34* (2013.01); *A61L 29/085* (2013.01); *A61L 29/16* (2013.01); *A61M 25/10* (2013.01); *A61K 9/0019* (2013.01); *A61L 2300/416* (2013.01); *A61L 2300/62* (2013.01); *A61L 2300/63* (2013.01); *A61L 2400/06* (2013.01); *A61L 2420/06* (2013.01); *A61L 2420/08* (2013.01); *A61M 2025/105* (2013.01)

(58) Field of Classification Search
None
See application file for complete search history.

(56) References Cited

U.S. PATENT DOCUMENTS

| | | | |
|---|---|---|---|
| 3,389,099 | A | 6/1968 | Dressier et al. |
| 3,936,391 | A | 2/1976 | Gabby et al. |
| 4,195,637 | A | 4/1980 | Gruntzig et al. |
| 4,456,627 | A | 6/1984 | Van Heteren |
| 4,490,421 | A | 12/1984 | Levy |
| 4,638,045 | A | 1/1987 | Kohn et al. |
| 4,722,906 | A | 2/1988 | Guire |
| 4,973,493 | A | 11/1990 | Guire |
| 4,979,959 | A | 12/1990 | Guire |
| 5,002,582 | A | 3/1991 | Guire et al. |
| 5,041,089 | A | 8/1991 | Mueller et al. |
| 5,073,641 | A | 12/1991 | Bundgaard et al. |
| 5,087,246 | A | 2/1992 | Smith |
| 5,102,402 | A | 4/1992 | Dror et al. |

(Continued)

FOREIGN PATENT DOCUMENTS

| | | |
|---|---|---|
| CA | 2836266 | 11/2012 |
| CA | 2760187 | 1/2018 |

(Continued)

OTHER PUBLICATIONS

Avella (Carbohydrate Polymers vol. 69, Issue 3, Jun. 25, 2007, pp. 503-511).*
Akiyama, Yohko et al., "In Vitro and in Vivo evaluation of Mucoadhesive Microspheres Prepared for the Gastrointestinal Tract Using Polyglycerol Esters of Fatty Acids and a Poly(acrylic acid) Derivative," Pharmaceutical Research, vol. 12, No. 3, 1995 1995,397-405.
Babayan, V K. "Preparation and Properties of Some Polyglycerol Esters of Short and Medium Length Fatty Acids," Journal of the American Oil Chemists' Society Jul. 1971 Jul. 1971, 307-309.
Babayan, V K. et al., "Nutritional Studies of Polyglycerol Esters," The Journal of the American Oil Chemist' Society vol. 41, Jun. 1964 Jun. 1964, 434-438.

(Continued)

*Primary Examiner* — Tigabu Kassa
(74) *Attorney, Agent, or Firm* — Pauly, DeVries Smith & Deffner LLC

(57) ABSTRACT

Disclosed herein is a delivery composition for administering a hydrophobic active agent. In one embodiment, a delivery composition for local administration of a hydrophobic active agent to a tissue or organ of a patient is disclosed. In one embodiment, the delivery composition includes a cationic delivery agent, a therapeutically effective amount of a hydrophobic active agent and a pharmaceutically acceptable aqueous carrier. In one embodiment, the cationic delivery agent includes polyethyleneimine (PEI). In an embodiment, the invention includes a drug delivery device including a substrate; and coated therapeutic agent particles disposed on the substrate, the coated therapeutic agent particles comprising a particulate hydrophobic therapeutic agent; and a vinyl amine polymer. Methods of making the delivery composition, as well as kits and methods of use are also included herein.

13 Claims, 15 Drawing Sheets

(56) References Cited

U.S. PATENT DOCUMENTS

| | | |
|---|---|---|
| 5,201,753 A * | 4/1993 | Lampropoulos ......... G01D 9/00 604/100.03 |
| 5,263,992 A | 11/1993 | Guire |
| 5,297,607 A | 3/1994 | Beauchamp |
| 5,304,121 A | 4/1994 | Sahatjian |
| 5,318,587 A | 6/1994 | Davey |
| 5,334,146 A | 8/1994 | Ozasa |
| 5,382,234 A | 1/1995 | Cornelius et al. |
| 5,397,307 A | 3/1995 | Goodin |
| 5,414,075 A | 5/1995 | Swan et al. |
| 5,466,719 A | 11/1995 | Jakobson et al. |
| 5,502,219 A | 3/1996 | Harris |
| 5,512,329 A | 4/1996 | Guire et al. |
| 5,556,383 A | 9/1996 | Wang et al. |
| 5,558,642 A | 9/1996 | Schweich, Jr. et al. |
| 5,571,089 A | 11/1996 | Crocker |
| 5,585,506 A | 12/1996 | Harvey |
| 5,616,608 A | 4/1997 | Kinsella et al. |
| 5,632,773 A | 5/1997 | Graham et al. |
| 5,637,460 A | 6/1997 | Swan et al. |
| 5,714,360 A | 2/1998 | Swan et al. |
| 5,728,732 A | 3/1998 | Corey |
| 5,741,551 A | 4/1998 | Guire et al. |
| 5,776,101 A | 7/1998 | Goy |
| 5,807,331 A | 9/1998 | Den Heijer et al. |
| 5,811,447 A | 9/1998 | Kunz et al. |
| 5,833,657 A | 11/1998 | Reinhardt et al. |
| 5,858,653 A | 1/1999 | Duran et al. |
| 5,882,336 A | 3/1999 | Janacek |
| 5,891,451 A | 4/1999 | Guerrero et al. |
| 5,980,948 A | 11/1999 | Goedemoed et al. |
| 6,007,833 A | 12/1999 | Chudzik et al. |
| 6,077,698 A | 6/2000 | Swan et al. |
| 6,168,748 B1 | 1/2001 | Wang et al. |
| 6,177,522 B1 | 1/2001 | Brady et al. |
| 6,210,364 B1 | 4/2001 | Anderson et al. |
| 6,278,018 B1 | 8/2001 | Swan |
| 6,299,604 B1 | 10/2001 | Ragheb et al. |
| 6,328,710 B1 | 12/2001 | Wang et al. |
| 6,340,465 B1 | 1/2002 | Hsu et al. |
| 6,394,995 B1 | 5/2002 | Solar et al. |
| 6,436,440 B1 | 8/2002 | Meffert et al. |
| 6,444,324 B1 | 9/2002 | Sjoquist et al. |
| 6,465,178 B2 | 10/2002 | Chappa et al. |
| 6,482,348 B1 | 11/2002 | Wang et al. |
| 6,506,411 B2 | 1/2003 | Hunter et al. |
| 6,506,895 B2 | 1/2003 | Guire et al. |
| 6,544,544 B2 | 1/2003 | Hunter et al. |
| 6,514,734 B1 | 2/2003 | Clapper et al. |
| 6,515,009 B1 | 2/2003 | Kunz et al. |
| 6,517,515 B1 | 2/2003 | Eidenschink |
| 6,603,040 B1 | 8/2003 | Swan |
| 6,613,066 B1 | 9/2003 | Fukaya et al. |
| 6,620,904 B2 | 9/2003 | Lemke |
| 6,623,452 B2 | 9/2003 | Chien et al. |
| 6,623,504 B2 | 9/2003 | Vrba et al. |
| 6,663,662 B2 | 12/2003 | Pacetti et al. |
| 6,703,040 B2 | 3/2004 | Katsarava et al. |
| 6,730,064 B2 | 5/2004 | Ragheb et al. |
| 6,762,019 B2 | 7/2004 | Swan et al. |
| 6,896,842 B1 | 5/2005 | Hamilton et al. |
| 7,034,765 B2 | 4/2006 | Fischer et al. |
| 7,138,541 B2 | 11/2006 | Swan |
| 7,163,523 B2 | 1/2007 | Devens, Jr. et al. |
| 7,309,593 B2 | 12/2007 | Ofstead et al. |
| 7,438,710 B2 | 10/2008 | Anderson et al. |
| 7,507,469 B2 | 3/2009 | Yao et al. |
| 7,696,259 B2 | 4/2010 | Hanley et al. |
| 7,731,685 B2 | 6/2010 | Schaeffer et al. |
| 7,736,689 B2 | 6/2010 | Chappa et al. |
| 7,758,892 B1 | 7/2010 | Chen et al. |
| 7,797,033 B2 | 9/2010 | D'andrea et al. |
| 7,803,149 B2 | 9/2010 | Schaeffer et al. |
| 7,807,750 B2 | 10/2010 | Taton et al. |
| 7,820,193 B2 | 10/2010 | Hunter et al. |
| 7,850,727 B2 | 12/2010 | Shanley et al. |
| 8,034,765 B2 | 10/2011 | De et al. |
| 8,039,524 B2 | 10/2011 | Ralph et al. |
| 8,158,106 B2 | 4/2012 | Guire et al. |
| 8,172,793 B2 | 5/2012 | Choules et al. |
| 8,202,530 B2 | 6/2012 | Hossainy et al. |
| 8,246,576 B2 | 8/2012 | Slager |
| 8,257,305 B2 | 9/2012 | Scheller et al. |
| 8,293,262 B2 | 10/2012 | Chen et al. |
| 8,439,868 B2 | 5/2013 | Scheller et al. |
| 8,469,943 B2 | 6/2013 | Bates et al. |
| 8,487,137 B2 | 7/2013 | Guire et al. |
| 8,513,320 B2 | 8/2013 | Rooijmans |
| 8,557,272 B2 | 10/2013 | Zhao et al. |
| 8,673,387 B2 | 3/2014 | Bates et al. |
| 8,697,112 B2 | 4/2014 | Ditizio et al. |
| 8,809,411 B2 | 8/2014 | Rooijmans |
| 8,871,819 B2 | 10/2014 | Meyering et al. |
| 8,889,760 B2 | 11/2014 | Kurdyumov et al. |
| 8,952,103 B2 | 2/2015 | Blondel et al. |
| 9,375,517 B2 | 6/2016 | Babcock |
| 9,555,119 B2 | 1/2017 | Ventura et al. |
| 9,757,497 B2 | 9/2017 | Slager |
| 9,861,727 B2 | 1/2018 | Slager et al. |
| 9,999,675 B2 | 6/2018 | Ventura et al. |
| 10,058,634 B2 | 8/2018 | Chappa et al. |
| 10,213,528 B2 | 2/2019 | Slager et al. |
| 10,213,529 B2 | 2/2019 | Slager |
| 10,617,793 B2 | 4/2020 | Slager et al. |
| 10,898,446 B2 | 1/2021 | Kloke |
| 11,027,049 B2 | 6/2021 | Chappa et al. |
| 2002/0006493 A1* | 1/2002 | Chabrecek ............ A61L 27/34 428/64.1 |
| 2002/0123801 A1 | 9/2002 | Pacetti et al. |
| 2003/0065355 A1 | 4/2003 | Weber |
| 2003/0195611 A1 | 10/2003 | Greenhalgh et al. |
| 2003/0211135 A1 | 11/2003 | Greenhalgh et al. |
| 2004/0044404 A1 | 3/2004 | Stucke et al. |
| 2004/0051201 A1 | 3/2004 | Greenhalgh et al. |
| 2004/0105839 A1 | 6/2004 | Park |
| 2004/0117007 A1 | 6/2004 | Whitbourne et al. |
| 2005/0100580 A1* | 5/2005 | Osborne ............... A61L 29/085 424/424 |
| 2005/0187605 A1 | 8/2005 | Greenhalgh et al. |
| 2005/0255142 A1 | 11/2005 | Chudzik et al. |
| 2005/0281857 A1 | 12/2005 | Heyer et al. |
| 2006/0018948 A1 | 1/2006 | Guire et al. |
| 2006/0067908 A1 | 3/2006 | Ding et al. |
| 2006/0148982 A1 | 7/2006 | Uchegbu et al. |
| 2006/0200232 A1 | 9/2006 | Phaneuf et al. |
| 2006/0240194 A1 | 10/2006 | Lemke et al. |
| 2007/0026037 A1 | 2/2007 | Kloke et al. |
| 2007/0032882 A1 | 2/2007 | Lodhi et al. |
| 2007/0048351 A1 | 3/2007 | Lunn |
| 2007/0065481 A1 | 3/2007 | Chudzik et al. |
| 2007/0154591 A1 | 7/2007 | Andersen |
| 2007/0155906 A1 | 7/2007 | Hissink et al. |
| 2007/0218102 A1 | 9/2007 | Chudzik et al. |
| 2007/0224247 A1 | 9/2007 | Chudzik et al. |
| 2007/0260054 A1 | 11/2007 | Chudzik |
| 2008/0020013 A1 | 1/2008 | Reyes et al. |
| 2008/0220054 A1 | 9/2008 | Shastri et al. |
| 2008/0233183 A1 | 9/2008 | Mccook et al. |
| 2009/0030504 A1 | 1/2009 | Weber et al. |
| 2009/0043276 A1 | 2/2009 | Weber et al. |
| 2009/0043378 A1 | 2/2009 | Cheng et al. |
| 2009/0081276 A1 | 3/2009 | Alsberg et al. |
| 2009/0221767 A1 | 9/2009 | Malet |
| 2009/0226501 A1 | 9/2009 | Parsonage et al. |
| 2009/0227946 A1 | 9/2009 | Kangas |
| 2010/0015240 A1 | 1/2010 | Biggs |
| 2010/0040766 A1 | 2/2010 | Chappa et al. |
| 2010/0076377 A1 | 3/2010 | Ehrenreich et al. |
| 2010/0076401 A1 | 3/2010 | Von et al. |
| 2010/0087783 A1 | 4/2010 | Weber et al. |
| 2010/0096320 A1 | 4/2010 | Opperman et al. |
| 2010/0130837 A1 | 5/2010 | Matott |
| 2010/0272774 A1 | 10/2010 | Chappa |
| 2010/0292668 A1 | 11/2010 | Slager |

(56) References Cited

U.S. PATENT DOCUMENTS

| | | | |
|---|---|---|---|
| 2011/0008260 A1* | 1/2011 | Flanagan | A61P 35/00 424/9.3 |
| 2011/0022027 A1 | 1/2011 | Morishita et al. | |
| 2011/0144373 A1 | 6/2011 | Swan et al. | |
| 2011/0245367 A1 | 10/2011 | Kurdyumov et al. | |
| 2011/0250255 A1 | 10/2011 | Parsonage et al. | |
| 2011/0257339 A1* | 10/2011 | Fischer | C08F 6/02 525/185 |
| 2011/0275725 A1 | 11/2011 | Meyering et al. | |
| 2012/0039983 A1 | 2/2012 | Uhrich et al. | |
| 2012/0046384 A2 | 2/2012 | Kurdyumov et al. | |
| 2012/0078227 A1 | 3/2012 | Kangas | |
| 2012/0083734 A1 | 4/2012 | Ayres et al. | |
| 2012/0148852 A1 | 6/2012 | Jelle et al. | |
| 2012/0177742 A1 | 7/2012 | Mcclain et al. | |
| 2012/0177910 A1 | 7/2012 | Weber et al. | |
| 2012/0296274 A1 | 11/2012 | Slager | |
| 2013/0143056 A1 | 6/2013 | Swan et al. | |
| 2013/0190689 A1 | 7/2013 | Slager | |
| 2013/0302529 A1 | 11/2013 | Kurdyumov | |
| 2014/0142166 A1 | 5/2014 | Ventura | |
| 2014/0162083 A1 | 6/2014 | Kurdyumov et al. | |
| 2014/0193474 A1 | 7/2014 | Babcock et al. | |
| 2014/0276636 A1 | 9/2014 | Lee et al. | |
| 2015/0140107 A1 | 5/2015 | Slager et al. | |
| 2015/0283092 A1 | 10/2015 | Ruddy et al. | |
| 2017/0072057 A1 | 3/2017 | Ventura et al. | |
| 2017/0112973 A1 | 4/2017 | Slager et al. | |
| 2018/0110903 A1 | 4/2018 | Slager et al. | |
| 2018/0169032 A1 | 6/2018 | Kloke | |
| 2018/0272040 A1 | 9/2018 | Chappa et al. | |
| 2020/0237971 A1 | 7/2020 | Slager et al. | |

FOREIGN PATENT DOCUMENTS

| | | |
|---|---|---|
| CN | 1950114 | 4/2007 |
| CN | 1964750 | 5/2007 |
| CN | 103442741 | 12/2013 |
| CN | 103906505 | 7/2014 |
| CN | 103990221 | 8/2014 |
| CN | 105163794 | 12/2015 |
| EP | 0882461 | 12/1998 |
| EP | 1176993 | 6/2003 |
| EP | 1430917 | 6/2004 |
| EP | 1994950 | 11/2008 |
| EP | 1997525 | 12/2008 |
| EP | 2098230 | 6/2012 |
| EP | 2292225 | 6/2012 |
| EP | 2569023 | 3/2013 |
| JP | 10328293 | 12/1998 |
| JP | 2009523493 | 6/2009 |
| JP | 2014515348 | 6/2014 |
| WO | 9964086 | 12/1999 |
| WO | 0110468 | 2/2001 |
| WO | 014572 | 6/2001 |
| WO | 2004017943 | 5/2004 |
| WO | 2005079754 | 9/2005 |
| WO | 2006019848 | 2/2006 |
| WO | 2006026187 | 3/2006 |
| WO | 2006053175 | 5/2006 |
| WO | 2007012051 | 1/2007 |
| WO | 2007106441 | 9/2007 |
| WO | 2007136504 | 11/2007 |
| WO | 2009051614 | 4/2009 |
| WO | 2009121629 | 10/2009 |
| WO | 2010111517 | 9/2010 |
| WO | 20100129328 A2 | 11/2010 |
| WO | 2011005421 | 1/2011 |
| WO | 2011024831 | 3/2011 |
| WO | 2011052089 | 5/2011 |
| WO | 2011143237 A1 | 11/2011 |
| WO | 2012162061 | 11/2012 |
| WO | WO2013169879 * | 11/2013 |
| WO | 2014071387 | 5/2014 |
| WO | 2014186729 | 11/2014 |
| WO | 2016123480 | 8/2016 |
| WO | 2018118671 | 6/2018 |

OTHER PUBLICATIONS

Birnbaum, Duane T. et al., "Microparticle Drug Delivery Systems," Chapter 6, Drug Delivery Systems in Cancer Therapy, 2003, (pp. 117-135).

Bodansky, M et al., "Utilization of Polyglycerol Esters," Biochemistry vol. 32 Aug. 30, 1938, 1938-1942.

Charlemagne, D et al., "Enzymatic Synthesis of Polyglycerol-Fatty Acid Esters in a Solvent-Free System," Journal for American Oil Chemists' Society vol. 72. No. 1 (1995) 1995, 61-65.

"Communication Pursuant to Article 94(3) EPC," for European Patent Application No. 11720694.6, dated Oct. 25, 2013 (6 pages).

"Communication Pursuant to Rules 161(1) and 162 EPC," for European Patent Application No. 12723063.9, dated Jan. 21, 2014 (2 pages).

De Meulenaer, B et al., "Development of Chromatographic Method for the Determination of Degree of Polymerisation of Polyglycerols and Polyglycerol Fatty Acid Esters," Chromatographia vol. 51, No. 1/2, Jan. 2000 Jan. 2000, 44-52.

Dobson, Kevin S. et al., "The Preparation of Polyglycerol Esters Suitable as Low-Caloric Fat Substitutes," Journal of The American Oil Chemists' Society vol. 70, No. 11 (Nov. 1993) Nov. 1993, 1089-1092.

Dow Corning Corp., "A guide to Silane Solutions," 2005.

Fao Nutrition Meetings REPORT, "Toxicological Evaluation of Some Antimicrobials, Antioxidants, Emulsifiers, Stabilizers, Flour-treatment Agents, Acids and Bases," Fao Nutrition Meetings Report Series No. 40A, B, C WHO/Food Add. 67.29 1966, 1-4.

File History for Related U.S. Appl. No. 13/104,383 downloaded May 11, 2015, 204 pages.

File History for Related U.S. Appl. No. 13/469,844 downloaded May 11, 2015, 239 pages.

File History for Related U.S. Appl. No. 13/793,390 downloaded May 11, 2015, 134 pages.

File History for Related U.S. Appl. No. 14/072,520 downloaded May 11, 2015, 101 pages.

File History for Related U.S. Appl. No. 14/609,270 downloaded May 11, 2015, 137 pages.

Finkel, Toren "Relief with Rapamycin: mTOR Inhibition Protects Against Radiation-Induced Mucositis," Cell Stem Cell, vol. 11:3, Sep. 7, 2012 (4 pages).

"First Office Action," for Chinese Patent Application No. 2012800328049, dated Mar. 2, 2015 (7 pages) including English translation.

From Wikipedia, "Electrospinning," From Wikipedia, the free encyclopedia, http://en.wikipedia.org/wiki/Electrospinning, downloaded Sep. 13, 2010; last updated Sep. 2, 2010, 2009, (pp. 1-6).

Ghonaim, Hassan M. et al., "N1,N12-Diacyl Spermines: SAR Studies on Non-viral Lipopolyamine Vectors for Plasmid DNA and siRNA Formulation," Pharmaceutical Research, vol. 27, No. 1, Jan. 2010 (p. 17-29) Oct. 30, 2009.

Hagemeier, C J. "Ocular Tolerability of Poly(lactide-co-glyoliide) Microspheres Following Subconjunctival and Inravitreal Injection in Rabbit Eyes," ARVO 2010 Presented ARVO 2010, Hall B/C, May 6, 2010 8:30am-10:15am May 6, 2010.

Howes, D et al., "The Fate of Ingested Glyceran Esters of Condensed Castor Oil Fatty Acids [Polyglycerol Polyricinoleate (PGPR)] in the Rat," Food and Chemical Toxicology 36 (1998) 719-738 1998, 719-738.

"International Preliminary Report on Patentability," for PCT/US2011/035951, dated Nov. 22, 2012 (8 pages).

"International Preliminary Report on Patentability," for PCT/US2012/038158, dated Nov. 28, 2013 (8 pages).

"International Search Report and Written Opinion," for PCT/US2012/035951, dated Aug. 3, 2011 (12 pages).

"International Search Report and Written Opinion," for PCT/US2012/038158, dated Sep. 27, 2012 (13 pages).

(56) References Cited

OTHER PUBLICATIONS

"International Search Report and Written Opinion," for PCT/US2013/068539, dated Jan. 22, 2014 (12 pages).
"International Search Report and Written Opinion," for PCT/US2014/038435, dated Aug. 25, 2014 (13 pages).
Kallinteri, Paraskevi et al., "Novel Functionalized Biodegradable Polymers for Nanoparticle Drug Delivery Systems," Biomacromolecules 2005 2006, 6, 1885-1894; American Chemical Society Apr. 27, 2005, 1885-1894.
Kumar, Majeti N.V. R. "Nano and Microparticles as Controlled Drug Delivery Devices," J. Pharm Pharmaceut Sci, 3(2), 2000 (pp. 234-258).
Liu, Rong "Water-Insoluble Drug Formulation," CRC Press, 2nd Ed., 2008 (pp. 1-3).
Love, Kevin T. et al., "Lipid-like materials for low-dose, in vivo gene silencing," www.pnas.org/cgi/doi/10.1073/pnas.0910603106 (6 pages).
Mcintyre, R T. "Polyglycerol esters," Journal of American Oil Chemists' Society Nov. 1979 (vol. 56) Nov. 1979, 835A-840A.
Orafei, Hossein et al., "Novel Poly(glycerol-adipate) Polymers Used for Nanoparticle Making: A Study of Surface Free Energy," Iranian Journal of Pharmaceutical Research (2008), 7 (1): 11-19 2008, 11-19.
Puri, Sanyogita "Drug Incorporation and Release of Water Soluble Drugs from Novel Functionalized Poly(glycerol adipate) Nanoparticles," Journal of Controlled Release 125 (2008) 59-67 Oct. 10, 2007, 59-67.
Renkin, Eugene M. "Filtration, Diffusion, and Molecular Sieving Through Porous Cellulose Membranes," Nov. 20, 1954 (pp. 1-19).
"Response to Communication Pursuant to Rule 161 and 162 EPC," for European Patent Application 12723063.9, dated Jan. 21, 2014 and filed with the EPO Jul. 18, 2014 (4 pages).
Salamone, Joseph "Hydrophic Polymers (for Friction Reduction)," Polymeric Materials Encyclopedia, vol. 12 (1996) p. 3107.
Santoyo, Antonio B. et al., "Biosynthesis of Polyglycerol Polyricinoleate (PGPR) with Rhizopus Arrhizus Lipase," Journal of Biotechnology 131S (2007) S74-S97 2007, S82.
Solvay Chemicals, "Polyglycerols for Ester Production," PGLC-05-002 Revised Aug. 2008 CGR4004, From www.solvaychemicals.us Aug. 2008, 1-7.
Takatori, Toshihito "Design of Controlled-Release Morphine Suppositories Containing Polyglycerol Ester of Fatty Acid," Biological Phamacy Bulletin 28(8) 1480-1484 (2005), vol. 28, No. 8 Aug. 2005, 1480-1484.
Yamagata, Yutaka et al., "Novel Sustained Release Dosage Forms of Proteins Using Polyglycerol Esters of Fatty Acids," Journal of Controlled Release vol. 63, Issue 3 Feb. 3, 2000, 319-329.
"Final Office Action," for U.S. Appl. No. 13/793,390 dated Nov. 16, 2015 (16 pages).
"Final Office Action," for U.S. Appl. No. 14/072,520 dated Oct. 26, 2015 (23 pages).
"International Preliminary Report on Patentability", for PCT/US2014/038435, dated Nov. 26, 2015 (10 pages).
"Communication Pursuant to Rules 161(1) and 162 EPC," for European Application No. 13792207.6, dated Aug. 5, 2015 (2 pages).
"Communication Under Rule 71(3) EPC," for European Patent Application No. 11720694.6, dated Jun. 1, 2015 (6 pages).
"International Preliminary Report on Patentability," for PCT/US2013/068539, dated May 14, 2015 (9 pages).
"Non-Final Office Action," for Japanese Patent Application No. 2013-510249, dated Jun. 2, 2015 (6 pages) with English Summary.
"Response to Non-Final Office Action," for U.S. Appl. No. 13/793,390, dated Feb. 5, 2015 and filed with the USPTO Jul. 6, 2015 (11 pages).
"Response to Non-Final Office Action," for U.S. Appl. No. 14/072,520, dated Feb. 18, 2015 and filed with the USPTO Jul. 17, 2015 (8 pages).
"Response to Non-Final Office Action," for U.S. Appl. No. 14/609,270, dated Mar. 27, 2015 and filed with the USPTO Jun. 25, 2015 (9 pages).

"Final Office Action," for U.S. Appl. No. 13/469,844 dated Jul. 14, 2016 (15 pages).
"International Search Report & Written Opinion," for PCT/US2016/015644 dated Jul. 11, 2016 (17 pages).
"Non-Final Office Action," for U.S. Appl. No. 14/609,270 dated Aug. 3, 2016 (14 pages).
"Communication Pursuant to Rules 161(1) and 162 EPC," for European Patent Application No. 14730381.2, dated Jan. 15, 2016 (2 pages).
"Final Office Action," for U.S. Appl. No. 14/609,270 dated Dec. 8, 2015 (27 pages).
"Final Office Action," For U.S. Appl. No. 13/793,390, dated Feb. 12, 2016 (08 pages).
"Invitation to Pay Additional Fees and Partial Search Report," for PCT Application No. PCT/US2016/015644, dated May 3, 2016 (8 pages).
"Non-Final Office Action," for U.S. Appl. No. 13/469,844 dated Dec. 3, 2015 (19 pages).
"Non-Final Office Action," for U.S. Appl. No. 14/072,520, dated Mar. 24, 2016 (4 pages).
"Response to Communication Pursuant to Rules 161(1) and 162 EPC," for European Application No. 13792207.6, filed with the EPO Feb. 3, 2016 (4 pages).
"Response to Final Office Action," for U.S. Appl. No. 13/793,390, dated Feb. 12, 2016 and filed with the USPTO Jul. 11, 2016 (13 pages).
"Response to Final Office Action," for U.S. Appl. No. 13/793,390, dated Nov. 16, 2015 and filed with the USPTO Jan. 19, 2016 (17 pages).
"Response to Final Office Action," for U.S. Appl. No. 14/072,520, dated Oct. 26, 2015 and filed with the USPTO Jan. 26, 2016 (7 pages).
"Response to Final Office Action," for U.S. Appl. No. 14/609,270, dated Dec. 8, 2015 and filed with the USPTO Apr. 1, 2016 (12 pages).
"Response to Non-FInal Office Action," for U.S. Appl. No. 13/469,844, dated Dec. 3, 2015 and filed with the USPTO Mar. 30, 2016 (9 pages).
"Response to Non-Final Office Action," for U.S. Appl. No. 14/072,520, dated Mar. 24, 2016 and filed with the USPTO Jun. 24, 2016 (6 pages).
"Communication Pursuant to Article 94(3) EPC," For European Application No. 10716714, dated Feb. 13, 2015 (6 pages).
"Decision of Refusal," for Japanese Patent Application No. 2012-508637, dated Feb. 3, 2015 (3 pages) with summary.
"File History", for U.S. Appl. No. 12/769,127, filed Apr. 28, 2010 to Mar. 2, 2017 (418 pages).
"Final Rejection," from CN Application No. 201080018767.7, dated Jan. 6, 2014 (10 pages).
"International Search Report and Written Opinion," for PCT/US2010/032741 dated Dec. 13, 2010 (11 pages).
"Invitation to Respond to Written Opinion," for SG Patent Application No. 201107896-1, dated Jun. 12, 2012 (6 pages).
"Non-Final Office Action," for Japanese Patent Application No. 2012-508637, dated Mar. 18, 2014 (4 pages) with translation.
"Non-Final Office Action," for Mexican Patent Application No. MX/a/2011/011389, dated Aug. 18, 2015 (1 page).
"Non-Final Office Action," for Mexican Patent Application No. MX/a/2011/011389, dated Feb. 22, 2016 (1 page).
"Non-Final Office Action," for U.S. Appl. No. 15/385,112, dated Feb. 24, 2017 (14 pages).
"Notification for Patent Reexamination," for Chinese Patent Application No. 201080018767.7, dated Sep. 25, 2014 (12 pages) with translation.
"Office Action," for Canadian Patent Application No. 2,760,187 dated Jan. 12, 2017 (3 pages).
"Office Action," for Canadian Patent Application No. 2,760,187 dated Mar. 24, 2016 (4 pages).
"Office Action," for Japanese Patent Application No. 2014511494 dated Feb. 5, 2016 (13 pages) with translation.
"Office Action," for Japanese Patent Application No. 2014511494 dated Nov. 25, 2016 (6 pages) with translation.

(56) References Cited

OTHER PUBLICATIONS

"International Preliminary Reporton Patentability," for PCT/US10/032741, dated Nov. 10, 2011 (8 pages).
"Response to Communication Pursuant to Article 94(3) EPC," for European Application No. 10716714.0 filed with EPO Aug. 11, 2015 (53 pages).
"Response to Final Office Action," for U.S. Appl. No. 13/469,844, dated Feb. 24, 2015 and filed with the USPTO Jul. 24, 2015 (7 pages).
"Response to Office Action," for Canadian Patent Application No. 2,760,187 filed with CIPO Feb. 15, 2017 (5 pages).
"Response to Office Action," for Canadian Patent Application No. 2,760,187 filed with CIPO Sep. 22, 2016 (22 pages).
Scheller, Bruno et al., "Paclitaxel Balloon Coating, a Novel Method for Prevention and Therapy of Restenosis," Circulation, Journal of the American Heart Association; 2004 (110), pp. 810-814. Online version of article http://circ.ahajournals.org/cgi/content/full/11/7/810, downloaded Jan. 12, 2011 2004, 6 pages.
"Second Office Action," for China Patent Application No. 2012800328049, dated Jan. 26, 2016 (9 pages), with translation.
"Third Office Action," for Chinese Patent Application No. 2012800328049, dated Aug. 11, 2016 (12 pages) with translation.
"Final Office Action," for U.S. Appl. No. 13/793,390 dated Dec. 19, 2016 (6 pages).
"Response to Non-Final Office Action," for U.S. Appl. No. 14/609,270, dated Aug. 3, 2016 and filed with the USPTO Dec. 15, 2016 (12 pages).
"Communication Pursuant to Article 94(3) EPC," for European Application No. 13792207.6, dated Sep. 29, 2017 (5 pages).
"Communication Pursuant to Rules 161(1) and 162 EPC," for European Patent Application No. 16703247.3 dated Sep. 15, 2017 (2 pages).
"Final Office Action," for U.S. Appl. No. 13/793,390 dated Sep. 7, 2017 (9 pages).
"Final Office Action," for U.S. Appl. No. 15/357,496 dated Sep. 20, 2017 (8 pages).
"Final Office Action," for U.S. Appl. No. 15/385,112 dated Aug. 24, 2017 (13 pages).
"International Preliminary Report on Patentability," for PCT Application No. PCT/US2016/015644 dated Aug. 10, 2017 (12 pages).
Mugabe, Clement et al., "Paclitaxel Incorporated in Hydrophobically Derivatized Hyperbranched Polyglycerols for Intravesical Bladder Cancer Therapy," BJU International, 2008, vol. 103, p. 978-986.
"Office Action," for Japanese Patent Application No. 2015-540868 dated Aug. 31, 2017 (10 pages) with English translation.
"Communication Pursuant to Article 94(3) EPC," for European Application No. 10716714, dated Jan. 18, 2013 (5 pages).
"Communication Pursuant to Article 94(3) EPC," for European Patent Application No. 12723063.9 dated Jun. 12, 2017 (5 pages).
"First Office Action," for Chinese Patent Application No. 201510411761.0 dated Jun. 30, 2017 (13 pages) with English translation.
"Fourth Office Action," for Chinese Patent Application No. 2012800328049, dated May 3, 2017 (8 pages) with English translation.
"Non-Final Office Action," for U.S. Appl. No. 12/769,127 dated Mar. 10, 2017 (33 pages).
"Non-Final Office Action," for U.S. Appl. No. 14/609,270 dated Apr. 10, 2017 (24 pages).
"Non-Final Office Action," for U.S. Appl. No. 15/357,496 dated Mar. 9, 2017 (8 pages).
"Response to Communication Pursuant to Article 94(3) EPC," for European Application No. 10716714.0 filed with EPO Jun. 10, 2013 (9 pages).
"Response to Final Office Action," for U.S. Appl. No. 13/793,390, dated Dec. 19, 2016 and filed with the USPTO May 19, 2017 (20 pages).
"Response to Non-Final Office Action," for U.S. Appl. No. 15/357,496, dated Mar. 9, 2017 and filed with the USPTO Jun. 9, 2017 (9 pages).
"Response to Non-Final Office Action," for U.S. Appl. No. 15/385,112, dated Feb. 24, 2017 and filed with the USPTO May 19, 2017 (10 Pages).
"Response to Non-Final Office Action," for U.S. Appl. No. 14/609,270, dated Apr. 10, 2017 and filed with the USPTO Jul. 21, 2017 (10 Pages).
"Communication Pursuant to Article 94(3) EPC," for European Patent Application No. 14730381.2 dated Nov. 21, 2017 (4 pages).
"Final Office Action," for U.S. Appl. No. 13/793,390 dated Jan. 11, 2018 (11 pages).
"Non-Final Office Action," for U.S. Appl. No. 15/385,112 dated Jan. 11, 2018 (11 pages).
"Non-Final Office Action," for U.S. Appl. No. 15/850,010 dated Jan. 24, 2018 (7 pages).
"Notice of Allowance," for U.S. Appl. No. 12/769,127 dated Nov. 13, 2017 (14 pages).
"Response to Communication Pursuant to Article 94(3) EPC," for European Patent Application No. 12723063.9 filed with the EPO Nov. 16, 2017 (9 pages).
"Response to Communication Pursuant to Article 94(3) EPC," for European Patent Application No. 14730381.2, filed with the European Patent Office Dec. 21, 2017 (68 pages).
"Response to Final Office Action," for U.S. Appl. No. 13/793,390, dated Sep. 7, 2017 and filed with the USPTO Dec. 7, 2017 (20 pages).
"Response to Final Office Action," for U.S. Appl. No. 15/385,112, dated Aug. 24, 2017 and filed with the USPTO Nov. 22, 2017 (13 pages).
"Response to Final Office Action," for U.S. Appl. No. 15/357,496, dated Sep. 20, 2017 and filed with the USPTO Dec. 20, 2017 (6 pages).
"Second Office Action," for Chinese Patent Application No. 201510411761.0 dated Dec. 22, 2017 (11 pages) with English translation.
"International Search Report and Written Opinion," for PCT Application No. PCT/US2017/066573 dated Apr. 3, 2018 (10 pages).
"Notice of Allowance," for U.S. Appl. No. 12/769,127 dated Feb. 23, 2018 (19 pages).
"Office Action," for Japanese Patent Application No. 2016-514136 dated Apr. 10, 2018 (7 pages) with English translation.
"Office Action," for Russian Patent Application No. 2014133462 dated Nov. 17, 2016 (7 pages) with English translation.
"Response to Communication Pursuant to Article 94(3) EPC," for European Patent Application No. 13792207.6, filed with the EPO Mar. 29, 2018 (25 pages).
"Response to Communication Pursuant to Rules 161(1) and 162 EPC," for European Patent No. 16703247.3 filed with the EPO on Mar. 22, 2018 (4 pages).
"Response to Non-Final Office Action," for U.S. Appl. No. 15/385,112, filed with the USPTO Apr. 20, 2018 (15 pages) for Non-Final Office Action dated Jan. 11, 2018.
"Communication Pursuant to Article 94(3) EPC," for European Patent Application No. 12723063.9 dated Jan. 16, 2019 (5 pages).
"Non-Final Office Action," for U.S. Appl. No. 15/850,010 dated Feb. 26, 2019 (13 pages).
"Office Action," for Canadian Patent Application No. 2,836,266 dated Nov. 30, 2018 (4 pages).
"Response to Communication Pursuant to Article 94(3) EPC," for European Patent Application No. 16703247.3 filed Dec. 20, 2018 (7 pages).
"Response to Final Office Action," for U.S. Appl. No. 15/850,010 filed with the USPTO Jan. 24, 2019 (10 pages).
"Response to First Examination Report," for Indian Patent Application No. 3723/KOLNP/2013 filed Feb. 20, 2019 (18 pages).
"Response to Non-Final Office Action," for U.S. Appl. No. 15/840,540 filed with the USPTO Dec. 20, 2018 (9 pages).
"Communication Pursuant to Article 94(3) EPC," for European Patent Application No. 16703247.3 dated Sep. 4, 2018 (5 pages).
"Decision of Rejection," for Chinese Patent Application No. 201510411761.0 dated Nov. 30, 2018 (8 pages, with English summary.
"Final Office Action," for U.S. Appl. No. 15/850,010 dated Oct. 2, 2018 (35 pages).

(56) References Cited

OTHER PUBLICATIONS

"First Examination Report," for Indian Patent Application No. 3723/KOLNP/2013 dated Sep. 28, 2018 (5 pages).
"Non-Final Office Action," for U.S. Appl. No. 13/793,390 dated Jul. 13, 2018 (48 pages).
"Non-Final Office Action," for U.S. Appl. No. 15/385,112 dated Aug. 13, 2018 (8 pages).
"Non-Final Office Action," for U.S. Appl. No. 15/840,540 dated Oct. 17, 2018 (38 pages).
"Notice of Allowance," for U.S. Appl. No. 13/793,390 dated Oct. 31, 2018 (10 pages).
"Notice of Allowance," for U.S. Appl. No. 15/385,112 dated Oct. 5, 2018 (10 pages).
"Office Action," for Canadian Patent Application No. 2,836,266 dated Apr. 11, 2018 (3 pages).
"Office Action," for Japanese Patent Application No. 2015-540868 dated May 21, 2018 (6 pages) with English translation.
"Office Action," for Mexican Patent Application No. MX/a/2015/015589 dated Sep. 9, 2018 (1 page), translation only.
"Product Data Sheet," for PEBAX MV 1074 SA 01 MED from Arkema (2013, pp. 1-2) 2 pages.
"Response to Final Office Action," for U.S. Appl. No. 13/793,390, dated Jan. 11, 2018 and filed with the USPTO Jun. 11, 2018 (17 pages).
"Response to Non-Final Office Action," for U.S. Appl. No. 15/850,010, dated Jan. 24, 2018 and filed with the USPTO Jun. 11, 2018 (8 pages).
"Response to Non-Final Rejected," dated Aug. 13, 2018, for U.S. Appl. No. 15/385,112, submitted via EFS-Web on Sep. 12, 2018, 5 pages.
"Response to Non-Final Rejection," dated Jul. 13, 2018, for U.S. Appl. No. 13/793,390, submitted via EFS-Web on Sep. 12, 2018, 6 pages.
"Response to Office Action," for Canadian Patent Application No. 2,836,266 filed with CIPO Sep. 20, 2018 (28 pages).
"Third Office Action," for Chinese Patent Application No. 201510411761.0 dated Jul. 25, 2018 (14 pages) with English translation.
"Communication Pursuant to Article 94(3) EPC," for European Patent Application No. 16703247.3 dated Apr. 23, 2019 (5 pages).
"International Preliminary Report on Patentability," for PCT Application No. PCT/US2017/066573 dated Jul. 4, 2019 (7 pages).
"Final Office Action," for U.S. Appl. No. 15/840,540 dated Mar. 15, 2019 (15 pages).
"Office Action," for Israeli Patent Application No. 242545 dated May 28, 2019 (8 pages) with English Translation.
"Response to communication Pursuant to Article 94(3) EPC," for European Patent Application No. 12723063.9 filed Jul. 2, 2019 (56 pages).
"Response to Final Rejection," dated Mar. 15, 2019 for U.S. Appl. No. 15/840,540, submitted via EFS-Web on May 15, 2019, 13 pages.
"Response to Non-Final Rejection," dated Feb. 26, 2019 for U.S. Appl. No. 15/850,010, submitted via EFS-Web on Jun. 26, 2019, 6 pages.
"Response to Office Action," for Canadian Patent Application No. 2,836,266 filed May 29, 2019 (19 pages).
Chen, Xia-Chao et al., "Humidity-Triggered Self-Healing of Microporous Polyelectrolyte Multilayer Coatings for Hydrophobic Drug Delivery," Advanced Functional Materials, vol. 25, No. 48, Dec. 1, 2015 pp. 7470-7477 (8 pages).
"Communication Pursuant to Article 94(3) EPC," for European Patent Application No. 16703247.3 dated Feb. 12, 2020 (7 pages).
"Communication Pursuant to Article 94(3) EPC," for European Patent Application No. 17835893.3 dated Jun. 29, 2020 (5 pages).
"Final Office Action," for U.S. Appl. No. 15/840,540 dated Dec. 11, 2019 (22 pages).
"Final Office Action," for U.S. Appl. No. 15/994,263 dated Jan. 16, 2020 (29 pages).

"First Examination Report," for Indian Patent Application No. 201747029823 dated Nov. 25, 2019 (6 pages).
"First Office Action," for Chinese Patent Application No. 2016800187265 dated Nov. 5, 2019 (9 pages) with English Translation.
"First Office Action," for Russian Patent Application No. 2017129933 dated Jun. 27, 2019 (10 pages) with English Translation.
"Non-Final Office Action," for U.S. Appl. No. 15/840,540 dated Aug. 20, 2019 (20 pages).
"Non-Final Office Action," for U.S. Appl. No. 15/840,540 dated Mar. 30, 2020 (22 pages).
"Non-Final Office Action," for U.S. Appl. No. 15/994,263 dated Aug. 14, 2019 (50 pages).
"Notice of Allowance," for U.S. Appl. No. 15/850,010 dated Oct. 23, 2019 (14 pages).
"Office Action Response," for Israeli Patent Application No. 242545 filed Sep. 28, 2019 (133 pages) English Translation.
"Office Action," for Canadian Patent Application No. 2,836,266 dated Oct. 23, 2019 (3 pages).
"Office Action," for Canadian Patent Application No. 2,890,205 dated Sep. 18, 2019 (5 pages).
"Office Action," for Canadian Patent Application No. 2,912,690 dated Apr. 29, 2020 (5 pages).
"Office Action," for Israeli Patent Application No. 242545 dated Feb. 6, 2020 (7 pages) with English Translation.
"Office Action," for Japanese Patent Application No. 2017-540169 dated Nov. 21, 2019 (12 pages) with English Translation.
"Office Action," for Russian Patent Application No. 2017129933 dated Mar. 2, 2020 (9 pages) with English Translation.
"Office Action," for Russian Patent Application No. 2017129933 dated Oct. 21, 2019 (9 pages) with English Translation.
"Preliminary Office Action," for Brazilian Patent Application No. 1120170136420 dated Oct. 15, 2019 (7 pages) with English Translation.
"Reexamination Notification," for Chinese Patent Application No. 201510411761.0 dated Jun. 3, 2020 (13 pages) with English Translation.
"Response to Communication Pursuant to Article 94(3) EPC," for European Patent Application No. 16703247.3 filed Aug. 30, 2019 (10 pages).
"Response to Communication Pursuant to Rules 161(1) and 162 EPC," for European Patent Application No. 17835893.3 filed Jan. 21, 2020 (7 pages).
"Response to Final Office Action," for U.S. Appl. No. 15/840,540 filed with the USPTO Mar. 5, 2020 (13 pages).
"Response to Final Office Action," for U.S. Appl. No. 15/994,263 filed Apr. 16, 2020 (8 pages).
"Response to First Examination Report," for Indian Patent Application No. 201747029823 filed May 22, 2020 (13 pages).
"Response to Non-Final Office Action," for U.S. Appl. No. 15/840,540 filed with the USPTO Nov. 20, 2019 (13 pages).
"Response to Non-Final Office Action," for U.S. Appl. No. 15/944,253 filed with the USPTO Nov. 12, 2019 (15 pages).
"Response to Office Action," for Canadian Patent Application No. 2,836,266 filed Apr. 15, 2020 (18 pages).
"Response to Office Action," for Canadian Patent Application No. 2,890,205 filed Mar. 18, 2020 (28 pages).
"Response to Office Action," for Israeli Patent Application No. 242545 filed Jun. 7, 2020 (15 pages).
"Second Office Action," for Chinese Patent Application No. 2016800187265 dated Jun. 10, 2020 (10 pages) with English Translation.
"Written Submissions in Respect of Hearing on Nov. 14, 2019," for Indian Patent Application No. 3723/KOLNP/2013 filed Nov. 23, 2019 (19 pages).
"Non-Final Office Action," for U.S. Appl. No. 15/994,263 dated Jul. 15, 2020 (24 pages).
"Non-Final Office Action," for U.S. Appl. No. 16/847,272 dated Jan. 7, 2021 (36 pages).
"Notice of Allowance," for U.S. Appl. No. 15/840,540 dated Sep. 16, 2020 (18 pages).
"Notice of Allowance," for U.S. Appl. No. 15/994,263 dated Feb. 3, 2021 (13 pages).

(56) References Cited

OTHER PUBLICATIONS

"Office Action," for Canadian Patent Application No. 2,836,266 dated Jul. 23, 2020 (3 pages).
"Office Action," for Canadian Patent Application No. 2,912,690 dated Feb. 23, 2021 (3 pages).
"Office Action," for Canadian Patent Application No. 2,912,690 dated Nov. 5, 2020 (3 pages).
"Office Action," for Israeli Patent Application No. 253612 dated Jul. 31, 2020 (8 pages) with English Translation.
"Office Action," for Japanese Patent Application No. 2017-540169 dated Jul. 30, 2020 (9 pages) with English Translation.
"Office Action," for Mexican Patent Application No. MX/a/2017/009688 dated Dec. 10, 2020 (6 pages) with English Translation.
"Office Action," for Mexican Patent Application No. MX/a/2017/009688 dated Jul. 14, 2020 (5 pages) with English Translation.
"Response to Communication Pursuant to Article 94(3) EPC," for European Patent Application No. 16703247.3 filed Aug. 11, 2020 (10 pages).
"Response to Communication Pursuant to Article 94(3) EPC," for European Patent Application No. 17835893.3 filed Oct. 29, 2020 (7 pages).
"Response to Non-Final Office Action," for U.S. Appl. No. 15/840,540, filed Jul. 23, 2020 (15 pages).
"Response to Non-Final Office Action," for U.S. Appl. No. 15/994,263, filed Oct. 15, 2020 (10 pages).
"Response to Office Action," for Canadian Patent Application No. 2,836,266 filed Oct. 19, 2020 (8 pages).
"Response to Office Action," for Canadian Patent Application No. 2,912,690 filed Aug. 13, 2020 (39 pages).
"Response to Office Action," for Canadian Patent Application No. 2,912,690 filed Jan. 8, 2021 (21 pages).
"Response to Office Action," for Canadian Patent Application No. 2,912,690 filed Mar. 29, 2021 (16 pages).
"Third Office Action," for Chinese Patent Application No. 2016800187265 dated Feb. 1, 2021 (11 pages) with English Translation.
"Final Office Action," for U.S. Appl. No. 16/847,272 dated Aug. 4, 2021 (13 pages).
"First Office Action," for Chinese Patent Application No. 2017800790755 dated May 18, 2021 (21 pages) with English Translation.
"Fourth Office Action," for Chinese Patent Application No. 2016800187265 dated Jul. 26, 2021 (11 pages) with English Translation.
"Office Action," for Mexican Patent Application No. MX/a/2017/009688 dated Apr. 14, 2021 (9 pages) with English translation.
"Response to Non-Final Office Action," for U.S. Appl. No. 16/847,272, filed May 6, 2021 (5 pages).

* cited by examiner

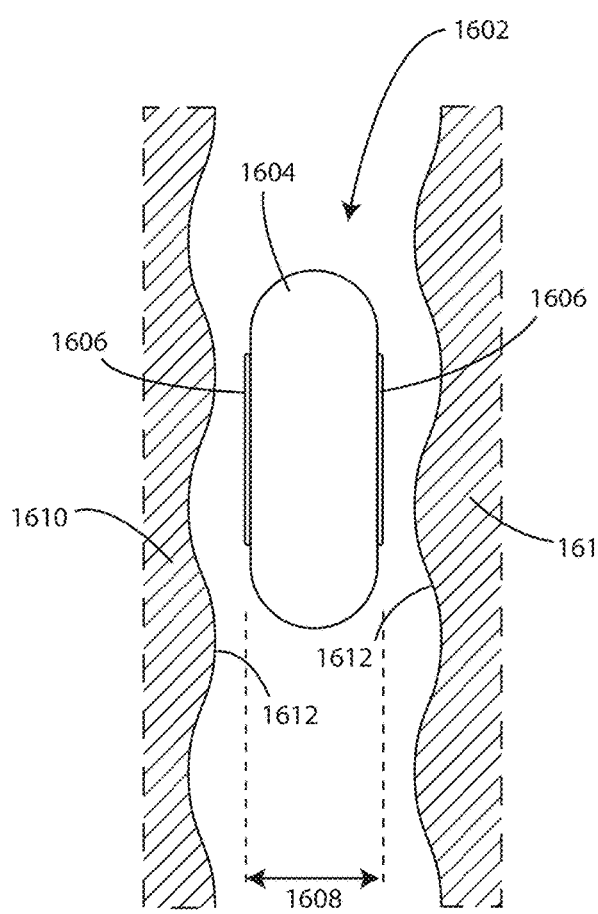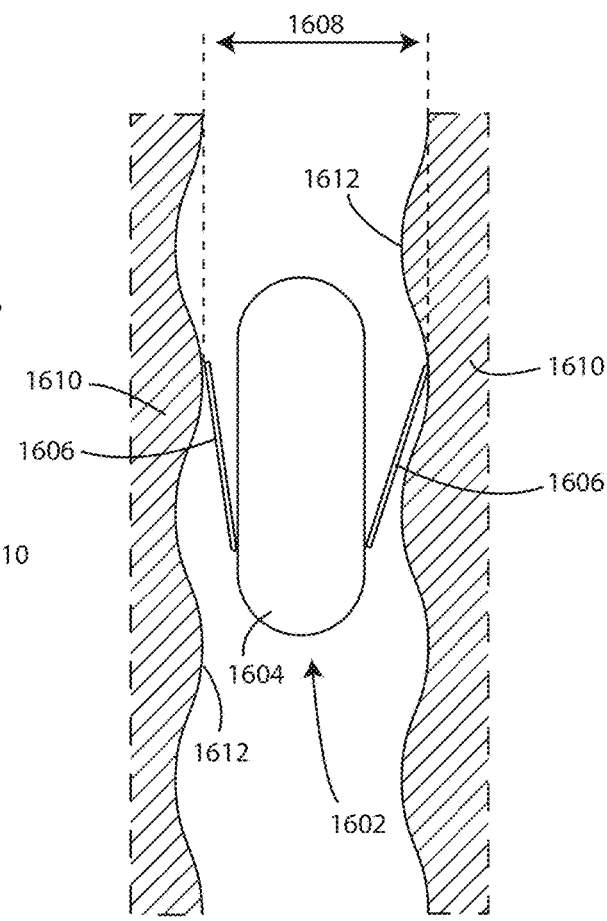
FIG. 16　　　　　FIG. 17
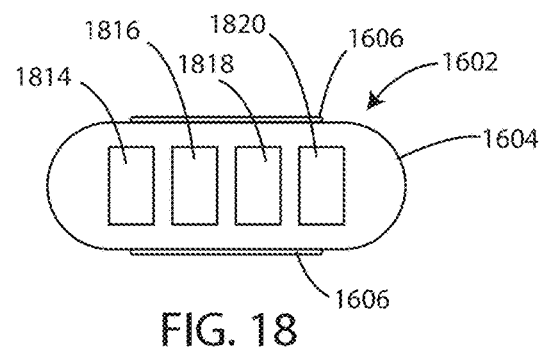
FIG. 18

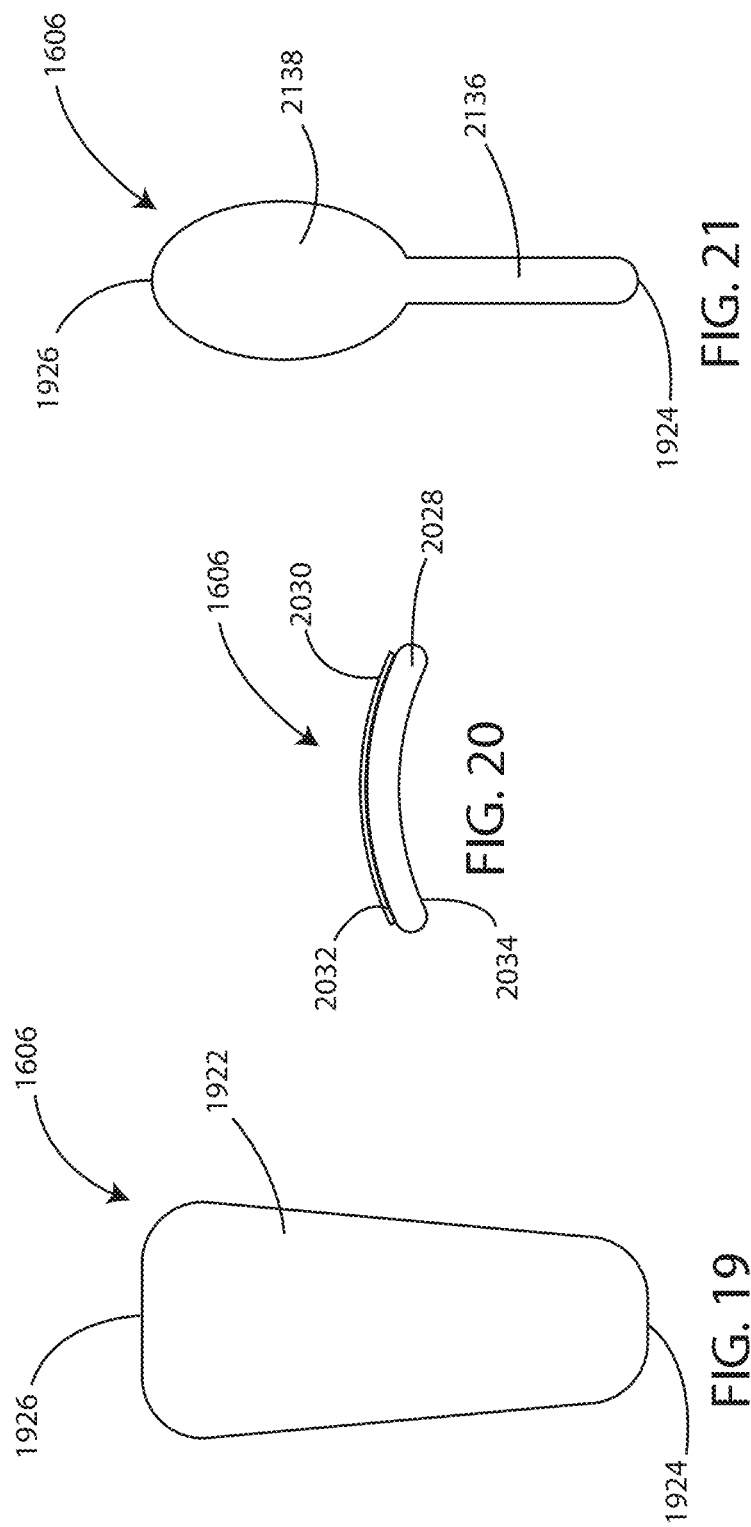

COMPOSITIONS AND METHODS FOR DELIVERY OF HYDROPHOBIC ACTIVE AGENTS

This application is a continuation-in-part of U.S. application Ser. No. 14/072,520, filed Nov. 5, 2013, which claims the benefit of U.S. Provisional Application No. 61/722,735, filed Nov. 5, 2012 and U.S. Provisional Application No. 61/740,713, filed Dec. 21, 2012. This application also claims the benefit of U.S. Provisional Application No. 61/824,160, filed May 16, 2013. The contents of all of these applications are herein incorporated by reference.

FIELD OF THE INVENTION

The present invention relates to compositions and methods for delivering biologically active agents to a patient. More specifically, the present invention relates to compositions and methods for local administration of hydrophobic active agents to a patient, such as coated hydrophobic active agent particles with excipients.

BACKGROUND OF THE INVENTION

Generally, the initial focus during development of a biologically active agent is the physiochemical properties of the pharmaceutical compound, in particular the therapeutic function of the compound. Once the biological activity of the active agent is defined, the design focus typically shifts to the systems and formulations by which the active agent is delivered. In particular, one focus during development of delivery systems and formulations is the provision of a system or formulation in which therapeutic titers of the active agent are able to reach the appropriate anatomical location or compartment after administration.

The phrase "route of administration" refers to the path by which an active agent is brought into contact with the body and is determined primarily by the properties of the active agent and by the therapeutic objectives. The route of administration that is chosen for a particular active agent may have a profound effect upon the speed and efficiency of the active agent upon administration.

In general, routes of administration can be classified by whether the effect is local or systemic. For local delivery, an active agent is applied directly to the tissue or organ for which treatment is sought. The effect of local delivery is limited primarily to the tissue or organ to which the active agent is applied. For example, local delivery may be accomplished through the use of compositions such as liniments, lotions, drops, ointments, creams, suppositories, emulsions, solutions, suspensions and the like. Local delivery can also be accomplished using special delivery devices such as catheters, syringes or implantables designed to convey drug to a specific region in the body. In contrast, an active agent administered systemically enters the blood or lymphatic supply and may be felt some distance from the site of administration. For systemic delivery, oral and parenteral routes are typically used.

A particular example of a site of administration is the vascular system. The vascular system of the human is subject to blockage due to plaque within the arteries. Partial and even complete blockage of arteries by the formation of an atherosclerotic plaque is a well-known and frequent medical problem. Frequently, such blockage occurs in the coronary arteries. Blockages may also occur secondary to past treatment of specific sites (restenosis—such as that stemming from rapidly dividing smooth muscle cells). In addition, blockages can also occur in the context of peripheral arteries.

Blockages may be treated using atherectomy devices, which mechanically remove the plaque; hot or cold lasers, which vaporize the plaque; stents, which hold the artery open; and other devices and procedures designed to increase blood flow through the artery.

One common procedure for the treatment of blocked arteries is percutaneous transluminal coronary angioplasty (PTCA), also referred to as balloon angioplasty. In this procedure, a catheter having an inflatable balloon at its distal end is introduced into the coronary artery, the deflated, folded balloon is positioned at the stenotic site, and then the balloon is inflated. Inflation of the balloon disrupts and flattens the plaque against the arterial wall, and stretches the arterial wall, resulting in enlargement of the intraluminal passageway and increased blood flow. After such expansion, the balloon is deflated, and the balloon catheter removed. A similar procedure, called percutaneous transluminal angioplasty (PTA), is used in arteries other than coronary arteries in the vascular system. In other related procedures, a small mesh tube, referred to as a stent is implanted at the stenotic site to help maintain patency of the coronary artery. In rotoblation procedures, also called percutaneous transluminal rotational atherectomy (PCRA), a small, diamond-tipped, drill-like device is inserted into the affected artery by a catheterization procedure to remove fatty deposits or plaque. In a cutting balloon procedure, a balloon catheter with small blades is inflated to position the blades, score the plaque and compress the fatty matter into the artery wall. During one or more of these procedures, it may be desirable to deliver a therapeutic agent or drug to the area where the treatment is occurring to prevent restenosis, repair vessel dissections or small aneurysms or provide other desired therapy.

Additionally, it may be desirable to transfer therapeutic agents to other locations in a mammal, such as the skin, neurovasculature, nasal, oral, the lungs, the mucosa, sinus, the GI tract or the renal peripheral vasculature.

SUMMARY OF THE INVENTION

Disclosed herein is a delivery composition for administration of a hydrophobic active agent, along with kits that include the delivery compositions, methods of making the delivery composition, and methods of using the delivery composition. In particular the invention provides a delivery composition for local administration of a hydrophobic active agent.

In one embodiment, the delivery composition includes a cationic delivery agent, a therapeutically effective amount of the hydrophobic active agent; and a pharmaceutically acceptable aqueous carrier. In one embodiment, the hydrophobic active agent is combined with the pharmaceutically acceptable aqueous carrier to form a suspension. In another embodiment, the cationic delivery agent is dissolved in the pharmaceutically acceptable carrier to form a solution. In a more particular embodiment, the cationic delivery agent includes polyetheyleneimine (PEI), for example, dissolved PEI, more particularly, branched PEI. In one embodiment, the cationic delivery agent includes branched PEI with a molecular weight of at least about 25 kD and up to about 5000 kD, at least about 70 kD and up to about 4000 kD, at least about 100 kD and up to about 3000 kD, or at least about 500 kD and up to about 1000 kD. In one embodiment, the branched PEI has a ratio of primary:secondary:tertiary amines between about 1:3:1 and about 1:1:1, or between about 1:2:1 and about 1:1:1. In one embodiment, the delivery composition includes cationic delivery agent:hydrophobic active agent at a ratio of at least about 1:1 and up to about 1:25, at least about 1:2 and up to about 1:20, or at least about 1:5 and up to about 1:10. In another embodiment, the delivery composition includes at least about 0.05 mg/ml, 0.1 mg/ml, 0.5 mg/ml or 1 mg/ml and up to about 25 mg/ml cationic delivery agent and at least about 5 mg/ml and up to about 125 mg/ml hydrophobic active agent. In another embodiment, the aqueous carrier includes water. In another embodiment, the delivery composition has a pH between 5 and 9, 6 and 8, or 7 and 8. In one embodiment, the hydrophobic active agent is an antiproliferative, analgesic, anti-inflammatory, anti-arrhythmic, anti-bacterial, anti-coagulant, anti-hypertensive, anti-muscarinic, anti-neoplastic, beta-blocker, cardiac inotropic agent, corticosteroids, lipid regulating agents, anti-anginal agents, or combinations thereof. In a more particular embodiment, the hydrophobic active agent is an antiproliferative selected from paclitaxel, sirolimus (rapamycin), everolimus, biolimus A9, zotarolimus, tacrolimus, and pimecrolimus and mixtures thereof.

The invention also provides a method of making the delivery compositions. In one embodiment, the method includes combining the hydrophobic active agent with a pharmaceutically acceptable aqueous carrier to form an active agent suspension; and adding the cationic delivery agent to the active agent suspension to form the delivery composition. In one embodiment, the method includes a step of crystallizing the hydrophobic active agent before combining the hydrophobic active agent with the aqueous carrier to form the active agent suspension. In another embodiment, the method includes a step of combining the cationic delivery agent with an aqueous solution to form a cationic delivery agent solution before adding the cationic delivery agent to the active agent suspension. In one embodiment, the pH of the cationic delivery agent solution is adjusted to a pH between 5 and 9 before adding the cationic delivery agent to the active agent suspension.

In another embodiment, the method of making the delivery composition includes combining the hydrophobic active agent with the cationic delivery agent to form an active agent mixture; and combining the active agent mixture with the aqueous carrier to form the delivery composition. In one embodiment, the method includes a step of crystallizing the active agent mixture before combining the mixture with the aqueous carrier.

The invention also provides kits that include a therapeutically effective amount of hydrophobic active agent; and cationic delivery agent. The kit components (i.e., the hydrophobic active agent and/or the cationic delivery agent) can be included in the kit as solids or as aqueous solutions, either individually or combined. The solid kit component can be either crystalline or amorphous.

In an embodiment, the invention includes a drug delivery device including a substrate, a hydrophilic polymer layer disposed on the substrate, and coated therapeutic agent particles disposed on the hydrophilic polymer layer. The coated therapeutic agent particles can include a particulate hydrophobic therapeutic agent and a vinyl amine polymer component.

In an embodiment, the invention includes a drug delivery coating comprising a polymeric layer, the polymeric layer comprising a hydrophilic surface. The coating can further include coated therapeutic agent particles disposed on the hydrophilic surface, the coated therapeutic agent particles including a particulate hydrophobic therapeutic agent core, and a vinyl amine polymer component.

In an embodiment, the invention includes a method of forming a drug delivery coating. The method can include applying a hydrophilic base coat onto a substrate, forming coated therapeutic agent particles, the coated therapeutic agent particles comprising a particulate hydrophobic therapeutic agent and a vinyl amine polymer component, and applying the coated therapeutic agent particles to the substrate.

In an embodiment, the invention includes a medical device comprising a capsule housing; control circuitry disposed with in the capsule housing; and at least one moveable element operably connected to the capsule housing. The moveable element can include a substrate and a coating disposed on the substrate, the coating comprising; a hydrophilic polymer layer disposed on the substrate; and coated therapeutic agent particles disposed on the hydrophilic polymer layer, the coated therapeutic agent particles comprising a particulate hydrophobic therapeutic agent; and a vinyl amine polymer component.

In an embodiment, the invention includes a medical device including a capsule housing; control circuitry disposed with in the capsule housing; at least one moveable element operably connected to the capsule housing, the moveable element comprising a substrate and a coating disposed on the substrate, the coating comprising a cationic delivery agent; a therapeutically effective amount of the hydrophobic active agent; and a pharmaceutically acceptable aqueous carrier.

The invention also provides methods for local administration of a therapeutically or prophylactically effective amount of a hydrophobic active agent to a tissue or organ of a patient.

BRIEF DESCRIPTION OF THE FIGURES

The invention may be more completely understood in connection with the following drawings, in which:

FIG. 16 is a schematic view of a device in accordance with an embodiment of the invention.

FIG. 17 is a schematic view of the device shown in FIG. 16 in a different configuration.

FIG. 18 is a schematic view of a device in accordance with an embodiment of the invention.

FIG. 19 is a schematic view of a moveable element in accordance with various embodiments herein.

FIG. 20 is a schematic end view of a moveable element in accordance with various embodiments herein.

FIG. 21 is a schematic view of a moveable element in accordance with various embodiments herein.

Figure 1:
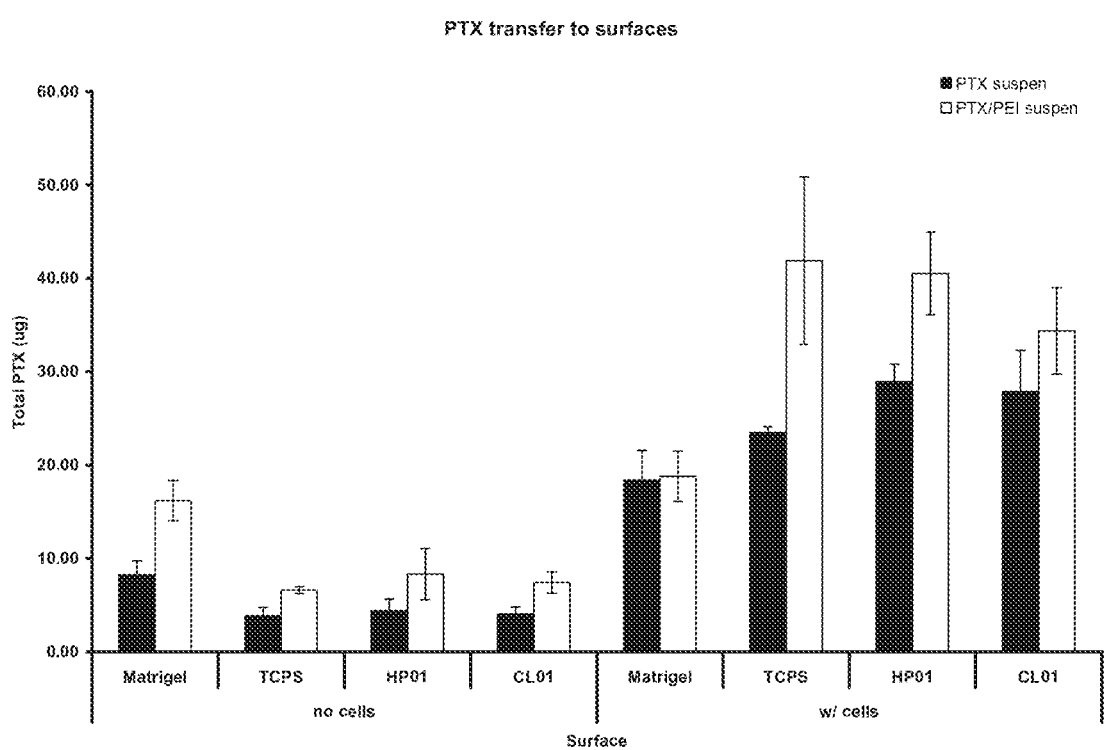
FIG. 1 is a graph showing the amount of paclitaxel adhered and/or transferred to different surfaces with or without seeded endothelial cells in the presence or absence of PEI.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As described above, in association with procedures such as percutaneous transluminal coronary angioplasty (PTCA), percutaneous transluminal angioplasty (PTA), and the like, it can be desirable to deliver a therapeutic agent or drug to the area where the treatment is occurring to prevent restenosis, repair vessel dissections or small aneurysms or provide other desired therapy. One approach for accomplishing this is to deliver a therapeutic agent (or active agent) to the desired tissue site using a drug delivery device such as a drug eluting balloon catheter or a drug-containing balloon catheter.

Drug delivery coatings for certain medical applications desirably exhibit various properties. By way of example, in the context of a drug eluting balloon catheter or a drug-containing balloon catheter, the coating should maintain structural integrity during steps associated with preparation of the balloon catheter device include pleating, folding, and curing (such as heat treatment). In addition, it is desirable for the coating to maintain structural integrity during the process of passing through the vasculature through a catheter and/or over the guide wire, with limited loss of the active agent. Yet, it is also desirable upon inflation of the balloon at the desired site to transfer a substantial amount of the active agent from the balloon and onto the vessel wall. In addition, it is desirable to maximize uptake of the active agent into the tissue of the of the vessel wall and reduce the amount of active agent that is washed away into the blood flowing through the treatment site in the vasculature.

Embodiments herein can be useful to enhance one or more desirable properties of drug delivery coatings, such as those properties desirable in the context of drug eluting balloon catheters, drug-containing balloon catheters and similar devices. In various embodiments, a drug delivery device is provided that includes a substrate and coated therapeutic agent particles disposed on the substrate. The coated therapeutic agent particles can include a particulate hydrophobic therapeutic agent and a vinyl amine polymer component disposed over the particulate hydrophobic therapeutic agent.

The invention described herein provides compositions and methods for delivery of an active agent to a patient. The compositions are referred to herein as "delivery compositions." As used herein, the term "route of administration" refers to the path by which an active agent is brought into contact with the body. The particular route of administration used with a particular active agent is determined primarily by properties of the active agent and by therapeutic objectives. In one embodiment, the invention provides compositions and methods for local administration of an active agent to a patient. As used herein, the term "local administration" refers to a route of administration in which a therapeutically effective amount of an active agent is applied directly to the tissue or organ for which treatment is sought, wherein the therapeutic effect of the active agent is limited primarily to the tissue or organ to which the active agent is applied. One advantage of local administration of an active agent is the ability to attain a pharmaceutically relevant concentration of active agent at a desired site, while reducing the risk of systemic toxicity. It is noted that some active agent may disperse from the local site of administration during local delivery. In general, less than about 50%, 40%, 30%, 20%, 10%, 5%, 4%, 3%, 2% or 1% of the active agent disperses from the site of administration during local administration. In contrast, for systemic delivery, the active agent is administered at a convenient access site, for example, intravascularly, intramuscularly, or orally and travels through the blood stream to the tissues or organs for which treatment is sought. In systemic delivery, more than 50% of the active agent disperses from the site of administration during systemic administration.

In a more particular embodiment, the invention provides compositions and methods for local delivery of a therapeutic amount of a hydrophobic active agent to a tissue or organ of a patient. In one embodiment, the invention provides a composition for local delivery of a hydrophobic active agent, wherein the composition includes the hydrophobic active agent and a cationic delivery agent. Suitable cationic delivery agent delivery and hydrophobic therapeutic agents are described in greater detail below. In another embodiment, one or more additives may be included in the delivery composition. Exemplary additive components are described in greater detail below.

Figure 7:
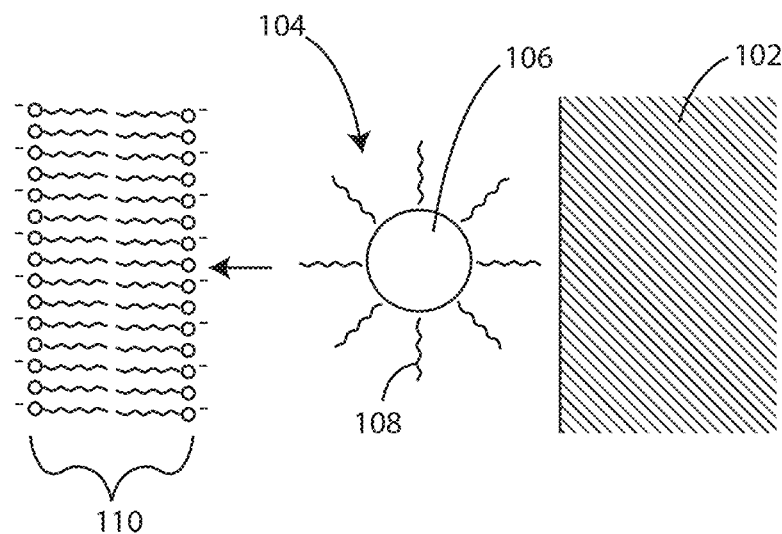
FIG. 7 is a schematic cross-sectional diagram of a coating in accordance with an embodiment herein.

Referring now to FIG. 7, a schematic cross-sectional diagram (not to scale) is provided of a coating in accordance with an embodiment herein. In this embodiment, coated therapeutic agent particles 104 are disposed on a substrate 102. Exemplary substrates are described in greater detail below. The coated therapeutic agent particles 104 can include a vinyl amine polymer component 108 disposed over a particulate hydrophobic therapeutic agent 106. It will be appreciated that as actually applied there will be many hydrophobic therapeutic agent particulates within a given coating and that a single particulate is shown in FIG. 7 just for purposes of ease of illustration. Exemplary vinyl amine polymer component compositions and hydrophobic therapeutic agents are described in greater detail below.

Figure 8:
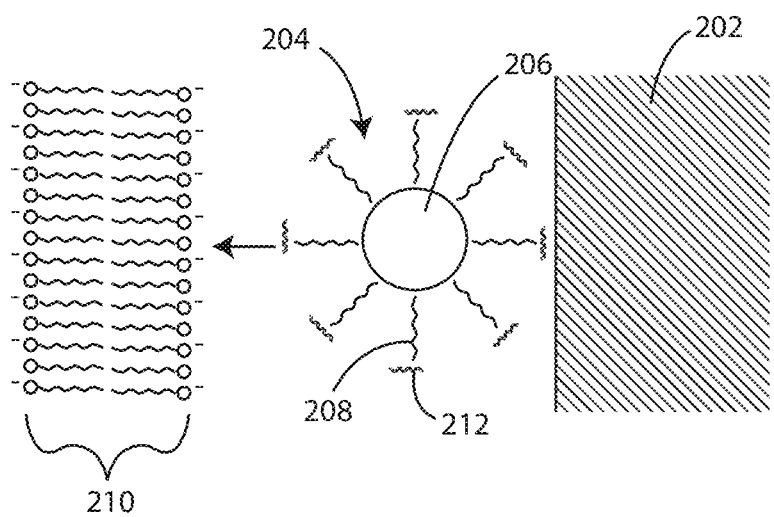
FIG. 8 is a schematic cross-sectional diagram of a coating in accordance with an embodiment herein.

In some embodiments, nucleic acids may also be included in coatings herein. By way of example, nucleic acids, including but not limited to siRNA, may be associated with the vinyl amine polymer. Exemplary nucleic acids are described in greater detail below. Referring now to FIG. 8, a schematic cross-sectional diagram (not to scale) is provided of another embodiment herein. In this embodiment, coated therapeutic agent particles 204 are disposed on a substrate 202. The coated therapeutic agent particles 204 can include a plurality of vinyl amine polymers 208 disposed over a particulate hydrophobic therapeutic agent 206. Nucleic acids 212 can be associated with the vinyl amine polymers.

Figure 9:
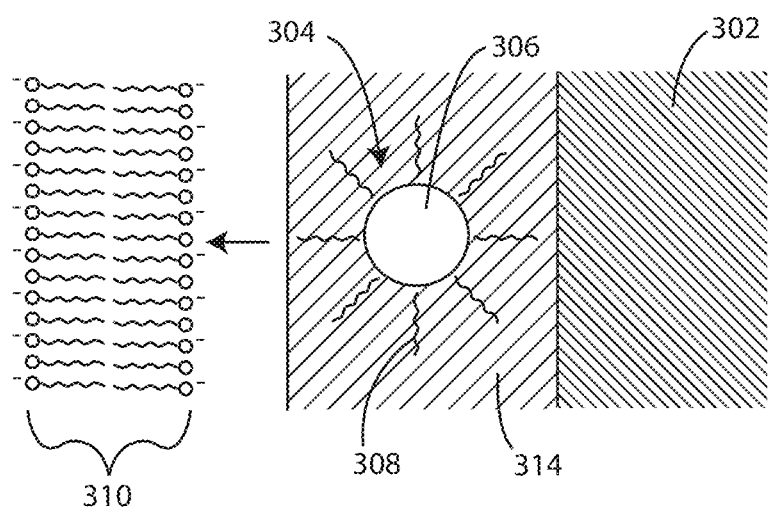
FIG. 9 is a schematic cross-sectional diagram of a coating in accordance with an embodiment herein.

In some embodiments, an additive may be included along with the coated therapeutic agent particles 304 in coatings herein. Referring now to FIG. 9, a schematic cross-sectional diagram (not to scale) is provided of another embodiment. In this embodiment, coated therapeutic agent particles 304 are disposed on a substrate 302. An additive 314 can be disposed along with the coated therapeutic agent particles 304. The amount of the additive 314 can be more than, less than, or equal to the amount of the coated therapeutic agent particles 304. In some embodiments, the additive 314 can form a matrix or layer in which the coated therapeutic agent particles 304 are disposed. In various embodiments, the additive can be hydrophilic. Exemplary additive components are described in greater detail below. The coated therapeutic agent particles 304 can include a plurality of vinyl amine polymers 308 disposed over a particulate hydrophobic therapeutic agent 306.

Figure 10:
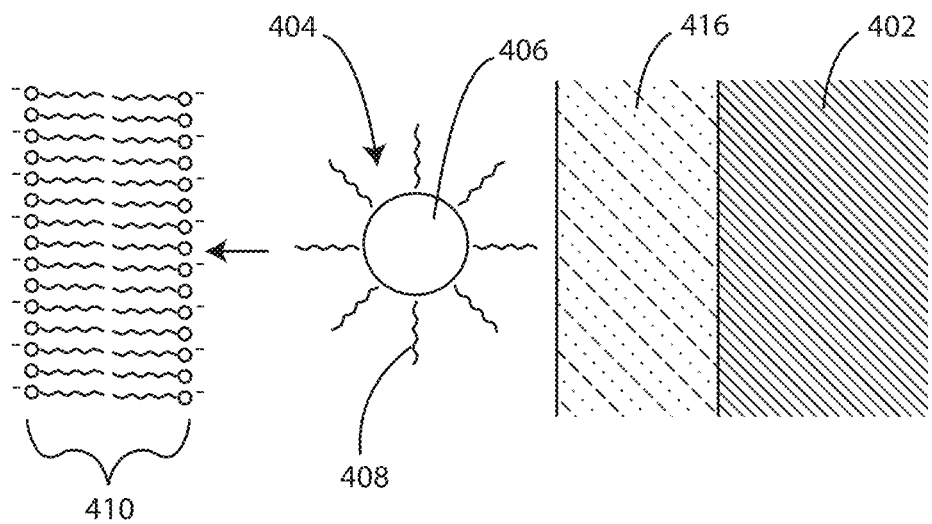
FIG. 10 is a schematic cross-sectional diagram of a coating in accordance with an embodiment herein.

In some embodiments, a hydrophilic polymer layer can be disposed on the surface of the substrate, between the coated therapeutic agent particles and the surface of the substrate. Exemplary polymers for the hydrophilic polymer layer are described in greater detail below. Referring now to FIG. 10, a schematic cross-sectional diagram (not to scale) is provided of another embodiment herein. In this embodiment, coated therapeutic agent particles 404 are disposed on a hydrophilic polymer layer 416, which is in turn disposed on a substrate 402. The coated therapeutic agent particles 404 can include a plurality of vinyl amine polymers 408 disposed over a particulate hydrophobic therapeutic agent 406.

Figure 11:
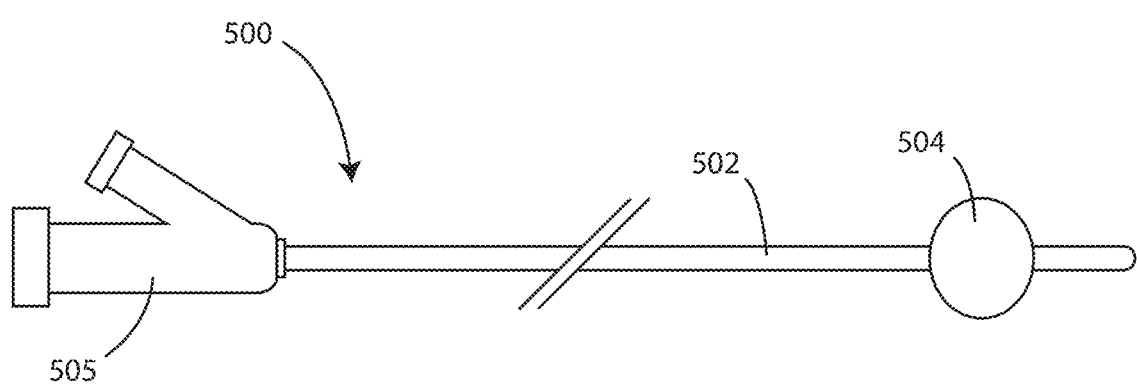
FIG. 11 is a schematic diagram of a device in accordance with an embodiment herein.

Referring now to FIG. 11, a schematic view of an exemplary device is shown in accordance with an embodiment. The device 500 can be, for example, an angioplasty balloon catheter or a drug eluting balloon catheter or a drug-containing balloon catheter. However, further examples of exemplary devices are described in greater detail below. The device 500 includes a catheter shaft 502 and a manifold end 505. The device 500 also includes an inflatable balloon 504 disposed around the catheter shaft 502. In FIG. 11, the balloon 504 is shown in an inflated configuration. The catheter shaft 502 can include a channel to convey fluid through the catheter shaft 502 and to or from the balloon 504, so that the balloon 504 can selectively go from a deflated configuration to the inflated configuration and back again.

The manufacture of expandable balloons is well known in the art, and any suitable process can be carried out to provide the expandable substrate portion of the insertable medical device as described herein. Catheter balloon construction is described in various references, for example, U.S. Pat. Nos. 4,490,421, 5,556,383, 6,210,364, 6,168,748, 6,328,710, and 6,482,348. Molding processes are typically performed for balloon construction. In an exemplary molding process, an extruded polymeric tube is radially and axially expanded at elevated temperatures within a mold having the desired shape of the balloon. The balloon can be subjected to additional treatments following the molding process. For example, the formed balloon can be subjected to additional heating steps to reduce shrinkage of the balloon.

Referring back to FIG. 11, the insertable medical device 500 can also have one or more non-expandable (or inelastic) portions. For example, in a balloon catheter, the catheter shaft 502 portion can be the non-expandable portion. The non-expandable portion can be partially or entirely fabricated from a polymer. Polymers include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, polyamides such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone. The non-expandable portion can also be partially or entirely fabricated from a metal.

Hydrophobic Active Agents

In one embodiment, the delivery composition includes one or more hydrophobic active agents. In general, the term "hydrophobic active agent" refers to an active agent having solubility in water of less than about 100 μg/mL at 25° C. and neutral pH, less than about 10 μg/mL at 25° C. and neutral pH, or less than about 5 μg/ml at 25° C. and neutral pH. In one embodiment, the hydrophobic active agent is crystalline. In general, the term "crystalline" refers to a thermodynamically stable solid form of an active agent having "long range molecular order" in which the molecules are packed in a regularly ordered, repeating pattern. In another embodiment, the hydrophobic active agent is amorphous. The term "amorphous" refers to a solid form of an active agent in which the molecules do not have "long range molecular order", but rather are randomly arranged or retain only a "short range molecular order" typical of liquids. In general, crystalline forms of an active agent tend to have a higher level of purity and more stability than amorphous forms of the same active agent. Additionally, the crystalline form of an active agent tends to be more soluble than the amorphous form. One of skill in the art is aware of methods for determining whether an active agent is in a crystalline or amorphous form, for example, using x-ray diffraction.

The amount of hydrophobic active agent included in the delivery composition can vary depending upon many factors including the desired therapeutic outcome. However, the composition of the invention can include at least about 1 mg/ml, 2 mg/ml, 3 mg/ml, 4 mg/ml, 5 mg/ml, or 10 mg/ml, 15 mg/ml, 20 mg/ml, or 25 mg/ml or up to about 25 mg/ml, 50 mg/ml, 75 mg/ml, 100 mg/ml, 125 mg/ml or 150 mg/ml hydrophobic active agent.

It will be appreciated that hydrophobic active agents can include agents having many different types of activities. In some embodiments, hydrophobic active agents can include, but are not limited to, antiproliferatives such as paclitaxel, sirolimus (rapamycin), everolimus, biolimus A9, zotarolimus, tacrolimus, and pimecrolimus and mixtures thereof; analgesics and anti-inflammatory agents such as aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac; anti-arrhythmic agents such as amiodarone HCl, disopyramide, flecamide acetate, quinidine sulphate; anti-bacterial agents such as benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim; anti-coagulants such as dicoumarol, dipyridamole, nicoumalone, phenindione; anti-hypertensive agents such as amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL; anti-muscarinic agents: atropine, benzhexyl HCl, biperiden, ethopropazine HCl, hyoscyamine, mepenzolate bromide, oxyphencylcimine HCl, tropicamide; anti-neoplastic agents and immunosuppressants such as aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone; beta-blockers such as acebutolol, alprenolol, atenolol, labetalol, metoprolol, nadolol, oxprenolol, pindolol, propranolol; cardiac inotropic agents such as aminone, digitoxin, digoxin, enoximone, lanatoside C, medigoxin; corticosteroids such as beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; lipid regulating agents such as bezafibrate, clofibrate, fenofibrate, gemfibrozil, probucol; nitrates and other anti-anginal agents such as amyl nitrate, glyceryl trinitrate, isosorbide dinitrate, isosorbide mononitrate, pentaerythritol tetranitrate.

Other hydrophobic active agents include, but are not limited to, active agents for treatment of hypertension (HTN), such as guanethidine.

In a particular embodiment, the hydrophobic active agent includes paclitaxel, sirolimus (rapamycin), everolimus, biolimus A9, zotarolimus, tacrolimus, and pimecrolimus and mixtures thereof.

In one embodiment, the hydrophobic active agent includes chemotherapeutics, exemplified by the family of fluorouracils (e.g. 4-FU and 5-FU) and Carmustine (bis-chloroethylnitrosourea; BCNU).

In one embodiment, the hydrophobic active agent is combined with a cationic delivery agent in solution. In another embodiment, solid hydrophobic active agent, amorphous or crystalline, is combined with pure or neat cationic delivery agent, amorphous or crystalline, to form a mixture. In other embodiments, the hydrophobic active agents is conjugated to a cationic delivery agent. The conjugation can include a hydrophobic active agent covalently bonded to the cationic delivery agent. In some embodiments wherein the hydrophobic agent is conjugated to the cationic delivery agent a linking agent can be used to attach the hydrophobic agent to the cationic delivery agent. Suitable linking agents include, but are not limited to, polyethylene glycol, polyethylene oxide and polypeptides of naturally-occurring and non-naturally occurring amino acids. In some embodiments, linking agents can be biodegradable or cleavable in vivo to assist in release of the hydrophobic active agents. Exemplary linking agents can further include alkane or aromatic compounds with heteroatom-substitutions such as N, S, Si, Se or O.

In some embodiments, the particulate hydrophobic therapeutic agent can have an average diameter ("dn", number average) that is less than about 10 µm. Also, in some embodiments, the particulate hydrophobic therapeutic agent can have an average diameter of about 100 nm or larger. For example, the microparticulates associated with the expandable elastic portion can have an average diameter in the range of about 100 nm to about 10 µm, about 150 nm to about 2 µm, about 200 nm to about 5 µm, or even about 0.3 µm to about 1 µm.

Vinyl Amine Polymer Component

Embodiments herein can include a vinyl amine polymer component. By way of example, the vinyl amine polymer component can include poly(N-vinyl amine) (pNVA). In some embodiments, the vinyl amine polymer component can include the hydrolysis products of N-vinyl formamide (pNVF). The pNVF can be hydrolyzed to various degrees. In various embodiments, the pNVF can be at least about 10, 20, 30, 40, 50, 60, 70, 80, 90, or 95 percent hydrolyzed. In some embodiments, the pNVF can be 100% hydrolyzed to PNVA.

It will be appreciated that the vinyl amine polymer component in accordance with embodiments herein can also include copolymers, terpolymers, and the like including N-vinyl amine and/or N-vinyl formamide subunits. In some embodiments, the vinyl amine polymer component can include a copolymer having the formula A-B, wherein subunit A is N-vinyl amine and subunit B is N-vinyl formamide. Alternatively, subunit B can be an accessory subunit, such as 1-vinyl-2-pyrrolidone. Further examples of accessory subunits are described in greater detail below. The relative amounts of the subunits can vary. In some embodiments, the mole percent amount of subunit A can be at least about 10, 20, 30, 40, 50, 60, 70, 80, 90, 95, or 100 percent with the balance comprising subunit B. In some embodiments, the vinyl amine polymer component can include a copolymer having Formula I, wherein x is from 1 to 100 mole percent, and y is from 0 to 99 mole percent.

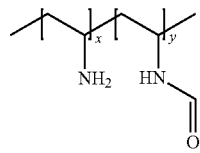

Formula I

In some embodiments, the vinyl amine polymer component can include a terpolymer having the formula A-B-C, wherein subunit A is N-vinyl amine, subunit B is N-vinyl formamide, and subunit C is an accessory subunit. In some embodiments, the mole percent amount of subunit A can be at least about 10, 20, 30, 40, 50, 60, 70, 80, 90, 95, or 100 percent with the balance comprising subunits B and/or C. In some embodiments, the vinyl amine polymer can include a terpolymer having Formula II, wherein x is from 1 to 100 mole percent, y is from 0 to 99 mole percent, and z is from 0 to 99 mole percent.

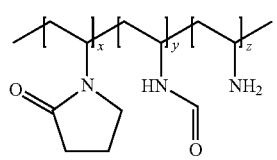

Formula II

Accessory subunits can include, but are not limited to, vinyl esters, (meth)acrylate esters, vinyl imidazoles, vinyl pyridines, vinyl alcohols, vinyl halides, acrylonitriles, acrylamides, vinyl silanes, styrenes, and the like. In some embodiments, the accessory subunit can be 1-vinyl-2-pyrrolidone.

In some embodiments, the vinyl amine polymer component can include blends of poly(N-vinyl amine) and poly (N-vinyl formamide). In some embodiments, the vinyl amine polymer component can include blends of poly(N-vinyl amine), poly(N-vinyl formamide), and other polymers such as polymers of the accessory subunits referred to above.

It will be appreciated that the vinyl amine polymer component along with any additive components and other components such as solvents and the like can have a particular pH. In some embodiments, the pH can be from about 2 to about 11. The pH range can include 2, 3, 4, 5, 6, 7, 8, 9, 10, or 11, wherein any of those numbers can serve as the bottom or top bound of a range. In particular embodiments the pH can be from about 2 to about 5. In some embodiments, the pH can be from about 3 to about 4. In some embodiments, the pH can be from about 4 to about 8. In some embodiments, the pH can be from about 5 to about 7.

Cationic Delivery Agents

In one embodiment, the delivery composition includes a hydrophobic active agent and cationic delivery agent. While not wishing to be bound by theory, it is believed that the charge provided by the cationic delivery agents results in the composition being electrostatically attracted to negative charges and/or polar groups associated with the lipid bilayer present on or in a tissues or organs of a patient or charged/polar groups associated with the extracellular matrix (e.g, collagen, fibronectin, laminin, etc.). Consequently, combining an active agent, particularly a hydrophobic active agent with a cationic delivery agent in a composition for local administration helps retain the hydrophobic active agent near the site of administration. It is also thought that the cationic delivery agent may increase tissue permeability, thereby enhancing uptake of the active agent by the target tissue and/or organ.

In general, the upper limit for the amount of cationic delivery agent that is included in the delivery composition is guided by the toxicity limit for the given cationic delivery agent or the solubility of the cationic delivery agent in the aqueous carrier used in the composition. However, in one embodiment, the ratio of cationic delivery agent:hydrophobic active agent can be up to 1:1. The lower limit for the amount of cationic delivery agent that is included in the composition is guided by the efficacy of the composition. In general, the inventors have found that a ratio of cationic delivery agent:hydrophobic active agent of 1:50 has limited efficacy. Consequently, the composition generally has a ratio of cationic delivery agent:hydrophobic active agent of at least 1:25. In one embodiment, the ratio of cationic delivery agent:hydrophobic active agent is between about 1:1 and about 1:25. In another embodiment, the ratio of cationic delivery agent:hydrophobic active agent is at least about 1:2, 1:5 or 1:10 and up to about 1:10, 1:15, 1:20 or 1:25. In one embodiment, the composition of the invention includes at least about 0.1 mg/ml, 0.5 mg/ml, 1 mg/ml, 2 mg/ml, 3 mg/ml, 4 mg/ml, or 5 mg/ml and up to about 5 mg/ml, 10 mg/ml, 15 mg/ml, 20 mg/ml or 25 mg/ml cationic delivery agent.

Cationic delivery agents used in embodiments herein include compounds containing a portion having a positive charge in aqueous solution at neutral pH along with a portion that can exhibit affinity for hydrophobic surfaces (such as hydrophobic or amphiphilic properties) and can therefore interface with hydrophobic active agents. In some embodiments, cationic delivery agents used in embodiments herein can include those having the general formula X-Y, wherein X is a positively charged group in aqueous solution at neutral pH and Y is a moiety exhibiting hydrophobic properties. In some embodiments, the cationic delivery agent can include a hydrophilic head and a hydrophobic tail, along with one or more positively charged groups, typically in the area of the hydrophilic head.

Cationic delivery agents can specifically include cationic lipids and net neutral lipids that have a cationic group. Exemplary lipids can include, but are not limited to, 3β-[N—(N',N'-dimethylaminoethane)-carbamoyl]cholesterol hydrochloride (DC-cholesterol); 1,2-dioleoyl-3-trimethylammonium-propane (DOTAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecenoyl)-3-dimethylammonium-propane (DODAP); 1,2-dilinoleyloxy-3-dimethylaminopropane (DLinDMA) and derivatives thereof. Additional lipids can include, but are not limited to, 1,2-dioleoyl-sn-glycero-3-phosphoethanolamine (DOPE); cholesterol; 1,2-dioctadecanoyl-sn-glycero-3-phosphocholine (DSPC); 1,2-distearoyl-sn-glycero-3-phosphoethanolamine (DSPE).

Cationic delivery agents can specifically include cationic polymers. Cationic delivery agents can also include polycation-containing cyclodextrin, histones, protamines, cationized human serum albumin, aminopolysaccharides such as chitosan, peptides such as poly-L-lysine, poly-L-ornithine, and poly(4-hydroxy-L-proline ester, and polyamines such as polyethylenimine (PEI; available from Sigma Aldrich), polypropylenimine, polyamidoamine dendrimers (PAMAM; available from Sigma Aldrich), cationic polyoxazoline and poly(beta-aminoesters). Cationic delivery agents can also specifically include cationic lipidoids (as described by K. T. Love in the publication PNAS 107, 1864-1869 (2010)). Other exemplary cationic polymers include, but are not limited to, block copolymers such as PEG-PEI and PLGA-PEI copolymers.

In one embodiment, the cationic delivery agent includes polyethyleneimine (PEI). PEI is a basic cationic aliphatic polymer which can be linear or branched. Linear PEI is a solid at room temperature and includes predominantly secondary amines. Branched PEIs are liquid at room temperature and include primary, secondary and tertiary amino groups. The ratio of primary:secondary:tertiary amino groups reflects the amount of branching, wherein the relative amount of secondary amino groups decreases as the amount of branching increases. In one embodiment, PEI includes primary:secondary:tertiary amino groups at a ratio of between about 1:3:1 and 1:1:1, or between about 1:2:1 and 1:1:1. In another embodiment, PEI includes primary:secondary:tertiary amino groups at a ratio of between about 1:2:1 and 1:1:1, 1:1.1:1, 1:1.2:1, 1:1.3:1, 1:1.4:1, 1:1.5:1, 1:1.6:1, 1:1.7:1, 1:1.8:1, or 1:1.9:1. In another embodiment, PEI is linear and includes predominantly secondary amines. In one embodiment, branched PEI includes no more than about 30%, 35%, 40%, 45%, 50%, 55%, 60%, 65%, 70%, or 75% secondary amine groups. In other embodiments, PEI includes one or more quaternary amine groups.

In one method, PEI is synthesized from monomers that include a three-membered ring in which two corners of the molecule have (—CH$_2$—) linkages and the third corner includes a secondary amine group (=NH). In the presence of a catalyst the three-membered ring is converted into a highly branched polymer with about 25% primary amine groups, 50% secondary amine groups, and 25% tertiary amine groups. The branched polymers can be copolymerized to produce PEI having a variety of molecular weights, from 2 kD up to 5000 kD. In one embodiment, PEI has a molecular weight of at least about 25 kD, 50 kD, 70 kD, 75 kD, 100 kD, 150 kD, 200 kD, 250 kD, 300 kD, 350 kD, 400 kD, 450 kD, 500 kD, 550 kD, 600 kD, 650 kD, 700 kD, 750 kD, 800 kD, 850 kD, 900 kD, 950 kD or 1000 kD and up to about 1000 kD, 1500 kD, 2000 kD, 2500 kD, 3000 kD, 3500 kD, 4000 kD, 4500 kD or 5000 kD. Methods for synthesizing linear PEI are also known.

The inventors have found that linear PEI is not as effective as a cationic delivery agent for hydrophobic active agents when compared to branched PEI. This could be because linear PEI is less soluble in aqueous carriers, such as water, than branched PEI. In general, linear PEI is only soluble in aqueous solutions such as water when it is heated to a temperature of at least about 50° C. Branched PEI is generally soluble in aqueous carriers such as water and a 5% aqueous solution of PEI typically has a pH between about 10 and 12. As the pH of a solution or suspension containing PEI is changed, the nature of the PEI molecule also changes. In particular, when the pH of a solution or suspension of PEI is between about 5 and about 9, the stability of the solution can be improved. The pH of a PEI solution can be adjusted by titrating with an acid, such as hydrochloric acid (HCl) having a concentration between about 1M and about 10 M. Advantageously, a solution with a pH between about 5 and about 9 is well suited for use in vivo. Branched PEI is highly soluble or miscible in water. The solubility limit for branched PEI depends on the amount of branching and molecular weight. In one embodiment, branched PEI has a solubility of at least about 0.01 mg/ml, 0.1 mg/ml, 1 mg/ml, 5 mg/ml, 10 mg/ml, 25 mg/ml or 50 mg/ml, and up to about 25 mg/ml, 50 mg/ml, 75 mg/ml, 100 mg/ml, 150 mg/ml or 200 mg/ml at room temperature (i.e., between about 20° C. and about 25° C.). Generally, PEI is used as a cationic delivery agent in an aqueous solution having a concentration of at least about 0.1 μg/ml, 0.2 μg/ml, 0.3 μg/ml, 0.4 μg/ml, 0.5 μg/ml, and up to about 0.6 μg/ml, 0.7 μg/ml, 0.8 μg/ml, 0.9 μg/ml or 1 μg/ml, wherein the aqueous solution is buffered to a pH of at least about 5, 6 or 7 or up to about 7, 8 or 9.

In other embodiments of the present disclosure, cationic delivery agents having a positive charge in aqueous solutions at neutral pH include the following Compounds (A-I):

Compound A

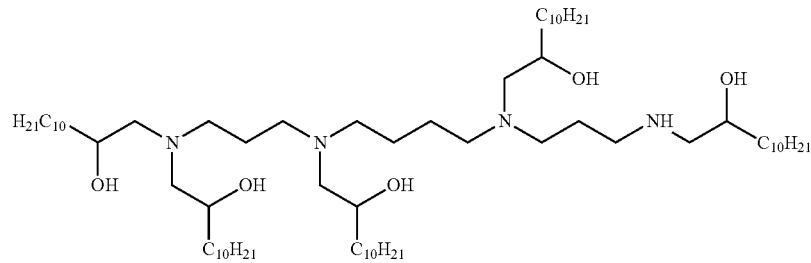

Compound B

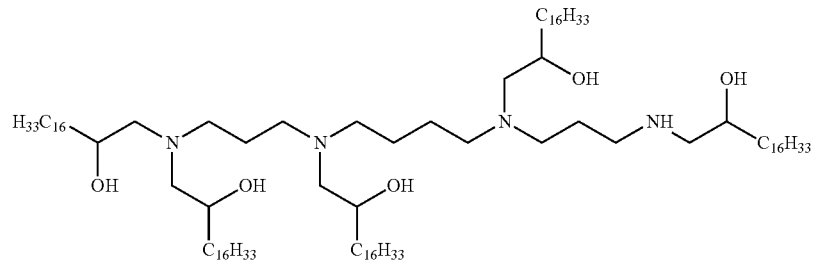

-continued

Compound C
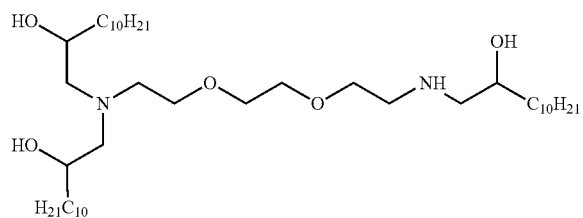

Compound D
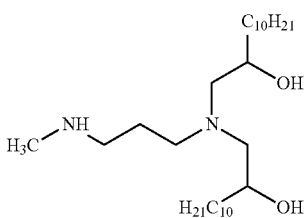

Compound E
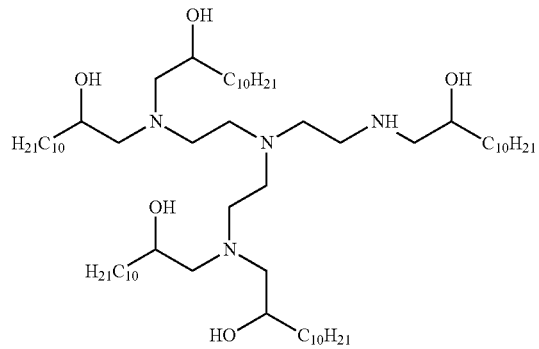

Compound F
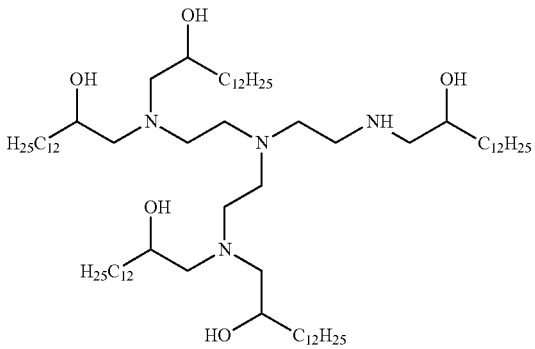

Compound G
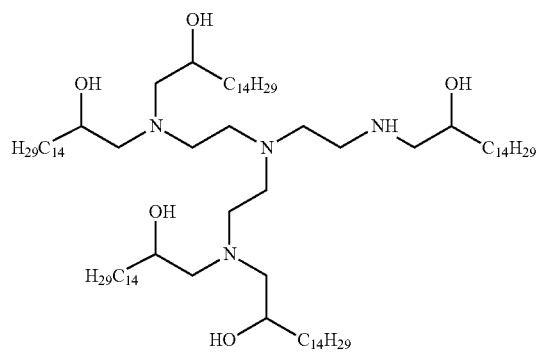

Compound H
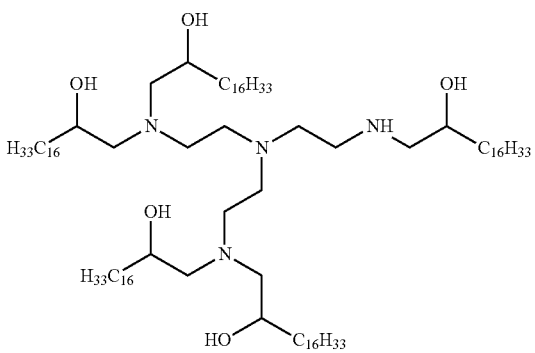

Compound I
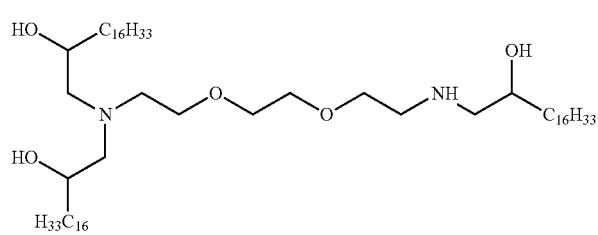

Additionally, other cationic delivery agents include structures of the general Formula I:

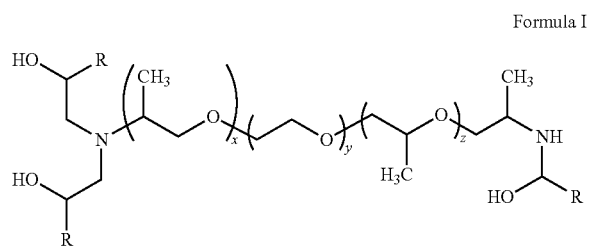

Formula I

TABLE 1

Values for Variables x + z, y and R for Compounds J-R of Formula I.

| Compound | x + z | y | R |
|---|---|---|---|
| Compound J | 6 | 12.5 | $C_{12}H_{25}$ |
| Compound K | 1.2 | 2 | $C_{12}H_{25}$ |
| Compound L | 6 | 39 | $C_{12}H_{25}$ |
| Compound M | 6 | 12.5 | $C_{14}H_{29}$ |
| Compound N | 1.2 | 2 | $C_{14}H_{29}$ |
| Compound O | 6 | 39 | $C_{14}H_{29}$ |
| Compound P | 6 | 12.5 | $C_{16}H_{33}$ |
| Compound Q | 1.2 | 2 | $C_{16}H_{33}$ |
| Compound R | 6 | 39 | $C_{16}H_{33}$ |

Methods for making cationic delivery agents, such as those listed above, are described in more detail in U.S.

patent application Ser. No. 13/469,844, entitled "DELIVERY OF COATED HYDROPHOBIC ACTIVE AGENT PARTICLES," the disclosure of which is hereby incorporated by reference herein in its entirety. In general, cationic delivery agents, such as those listed above, can generally be prepared by the reaction of an appropriate hydrophobic epoxide (e.g. oleyl epoxide) with a multifunctional amine (e.g. propylene diamine). Details of the synthesis of related cationic delivery agents are described by K. T. Love in the publication PNAS 107, 1864-1869 (2010) and Ghonaim et al., Pharma Res 27, 17-29 (2010).

It will be appreciated that polyamide derivatives of PEI (PEI-amides) can also be applied as cationic delivery agents. PEI-amides can generally be prepared by reacting PEI with an acid or acid derivative such as an acid chloride or an ester to form various PEI-amides. For example, PEI can be reacted with methyl oleate to form PEI-amides.

In yet other embodiments cationic delivery agents can include moieties used to condense nucleic acids (for example lipids, peptides and other cationic polymers). In some instances these cationic delivery agents can be used to form lipoplexes and polyplexes.

Additive Components

Additive components can be included with various embodiments herein. In some embodiments of the present disclosure the additive components can be hydrophilic in nature. Exemplary hydrophilic polymers include, but are not limited to, PEG, PVP and PVA.

Exemplary additive components can include saccharides. Saccharides can include monosaccharides, disaccharides, trisaccharides, oligosaccharides, and polysaccharides. Polysaccharides can be linear or branched polysaccharides. Exemplary saccharides can include but are not limited to dextrose, sucrose, maltose, mannose, trehalose, and the like. Exemplary saccharides can further include, but are not limited to, polysaccharides including pentose, and/or hexose subunits, specifically including glucans such as glycogen and amylopectin, and dextrins including maltodextrins, fructose, mannose, galactose, and the like. Polysaccharides can also include gums such as pullulan, arabinose, galactan, etc.

Saccharides can also include derivatives of polysaccharides. It will be appreciated that polysaccharides include a variety of functional groups that can serve as attachment points or can otherwise be chemically modified in order to alter characteristics of the saccharide. As just one example, it will be appreciated that saccharide backbones generally include substantial numbers of hydroxyl groups that can be utilized to derivatize the saccharide.

Saccharides can also include copolymers and/or terpolymers, and the like, that include saccharide and/or saccharide subunits and/or blocks.

Polysaccharides used with embodiments herein can have various molecular weights. By way of example, glycogen used with embodiments herein can have a molecular weight of greater than about 250,000. In some embodiments glycogen used with embodiments herein can have a molecular weight of between about 100,000 and 10,000,000 Daltons.

Refinement of the molecular weight of polysaccharides can be carried out using diafiltration. Diafiltration of polysaccharides such as maltodextrin can be carried out using ultrafiltration membranes with different pore sizes. As an example, use of one or more cassettes with molecular weight cut-off membranes in the range of about 1K to about 500 K can be used in a diafiltration process to provide polysaccharide preparations with average molecular weights in the range of less than 500 kDa, in the range of about 100 kDa to about 500 kDa, in the range of about 5 kDa to about 30 kDa, in the range of about 30 kDa to about 100 kDa, in the range of about 10 kDa to about 30 kDa, or in the range of about 1 kDa to about 10 kDa.

It will be appreciated that polysaccharides such as maltodextrin and amylose of various molecular weights are commercially available from a number of different sources. For example, Glucidex™ 6 (avg. molecular weight ~95,000 Da) and Glucidex™ 2 (avg. molecular weight ~300,000 Da) are available from Roquette (France); and MALTRIN™ maltodextrins of various molecular weights, including molecular weights from about 12,000 Da to 15,000 Da are available from GPC (Muscatine, Iowa). Examples of other hydrophobic polysaccharide derivatives are disclosed in US Patent Publication 2007/0260054 (Chudzik), which is incorporated herein by reference.

Exemplary additive components can include amphiphilic compounds. Amphiphilic compounds include those having a relatively hydrophobic portion and a relatively hydrophilic portion. Exemplary amphiphilic compounds can include, but are not limited to, polymers including, at least blocks of, polyvinylpyrrolidone, polyvinyl alcohol, polyethylene glycol, polyoxazolines (such as poly(2-alkyloxazoline) and derivatives) and the like. Exemplary amphiphilic compounds can specifically include poloxamers. Poloxamers are nonionic triblock copolymers composed of a central hydrophobic chain of polyoxypropylene flanked by two hydrophilic chains of polyoxyethylene. Poloxamers are frequently referred to by the trade name PLURONIC®. It will be appreciated that many aspects of the copolymer can be varied such the characteristics can be customized. One exemplary poloxamer is PLURONIC® F68 (non-ionic, copolymer of ethylene and propylene oxide commercially available from BASF Corporation; also designated as F68 and poloxamer F68), which refers to a poloxamer having a solid form at room temperature, a polyoxypropylene molecular mass of approximately 1,800 g/mol and roughly 80% polyoxyethylene content, with a total molecular weight of approximately 8,400 g/mol, the copolymer terminating in primary hydroxyl groups.

In other embodiments, the delivery composition of the invention can include one or more additional components, such as a diluent, excipient, adjuvant, emulsifier, buffer, stabilizer, preservative, and the like. In one embodiment, the delivery composition includes one or more contrast agents, for example, an iodinated radiocontrast agent.

In another embodiment, the delivery composition of the invention can include one or more agents that enhance tissue penetration, including, but not limited to zonulin, propylene glycol, mono-, di- or tri-glycerides etc.

Exemplary additive components can further include compounds that stabilize poorly water soluble pharmaceutical agents. Exemplary additive components providing such stabilization include biocompatible polymers, for example albumins. Additional additive components are described in U.S. Pat. No. 7,034,765 (De et al.), the disclosure of which is incorporated herein by reference. Stabilization of suspensions and emulsions can also be provided by compounds, for example, such as surfactants (e.g. F68).

Nucleic Acids

Nucleic acids used with embodiments of the invention can include various types of nucleic acids that can function to provide a therapeutic effect. Exemplary types of nucleic acids can include, but are not limited to, ribonucleic acids (RNA), deoxyribonucleic acids (DNA), small interfering RNA (siRNA), micro RNA (miRNA), piwi-interacting RNA (piRNA), short hairpin RNA (shRNA), antisense nucleic acids, aptamers, ribozymes, locked nucleic acids and catalytic DNA. In a particular embodiment, the nucleic acid used is siRNA and/or derivatives thereof.

Hydrophilic Base Coatings

In various embodiments, a hydrophilic base coating is included. One class of hydrophilic polymers useful as polymeric materials for hydrophilic base coat formation is synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Examples of polymers that can be formed from these monomers include poly(acrylamide), poly(methacrylamide), poly(vinylpyrrolidone), poly(acrylic acid), poly(ethylene glycol), poly(vinyl alcohol), and poly (HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,Ndimethylacrylamide-co-aminopropylmethacrylamide) and poly(acrylamide-co-N,Ndimethylaminopropylmethacrylamide) are described in example 2 of U.S. Pat. No. 7,807,750 (Taton et al.), the disclosure of which is incorporated herein by reference.

In some embodiments, the hydrophilic polymer is a vinyl pyrrolidone polymer, or a vinyl pyrrolidone/(meth)acrylamide copolymer such as poly(vinylpyrrolidone-comethacrylamide). If a PVP copolymer is used, it can be a copolymer of vinylpyrrolidone and a monomer selected from the group of acrylamide monomers. Exemplary acrylamide monomers include (meth)acrylamide and (meth)acrylamide derivatives, such as alkyl(meth)acrylamide, as exemplified by dimethylacrylamide, and aminoalkyl(meth)acrylamide, as exemplified by aminopropylmethacrylamide and dimethylaminopropylmethacrylamide. For example, poly(vinylpyrrolidone-co-N,N dimethylaminopropylmethacrylamide) is described in example 2 of U.S. Pat. No. 7,807,750 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. This provides a hydrophilic polymer having a pendent activatable photogroup that can be applied to the expandable and collapsible structure, and then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075, the disclosure of which is incorporated herein by reference. Methods for the preparation of photopolyacrylamide are described in U.S. Pat. No. 6,007,833, the disclosure of which is incorporated herein by reference.

In another embodiment, the polymers and copolymers as described are derivatized with one or more polymerizable group(s). Polymers with pendent polymerizable groups are commonly referred to macromers. The polymerizable group(s) can be present at the terminal portions (ends) of the polymeric strand or can be present along the length of the polymer. In one embodiment polymerizable groups are located randomly along the length of the polymer.

Optionally, the coating can include a cross-linking agent. A crosslinking agent can promote the association of polymers in the coating, or the bonding of polymers to the coated surface. The choice of a particular crosslinking agent can depend on the ingredients of the coating composition.

Suitable crosslinking agents include two or more activatable groups, which can react with the polymers in the composition. Suitable activatable groups include photoreactive groups as described herein, like aryl ketones, such as acetophenone, benzophenone, anthraquinone, anthrone, quinone, and anthrone-like heterocycles. The photoactivatable cross-linking agent can be ionic, and can have good solubility in an aqueous composition. Thus, in some embodiments, at least one ionic photoactivatable cross-linking agent is used to form the coating. The ionic cross-linking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable cross-linking agents include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603,040 (Swan) and U.S. Pat. No. 7,138,541 (Swan) the disclosures of which are incorporated herein by reference.

Other exemplary ionic photoactivatable cross-linking agents include ethylenebis(4-benzoylbenzyldimethylammonium) dibromide and hexamethylenebis(4-benzoylbenzyldimethylammonium) dibromide and the like. See U.S. Pat. No. 5,714,360 (Swan et al.) the disclosures of which are incorporated herein by reference.

In yet other embodiments, restrained multifunctional reagents with photoactivable cross-linking groups can be used. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Additional cross-linking agents can include those having formula $Photo^1$-LG-$Photo^2$, wherein $Photo^1$ and $Photo^2$ independently represent at least one photoreactive group and LG represents a linking group comprising at least one silicon or at least one phosphorus atom, wherein the degradable linking agent comprises a covalent linkage between at least one photoreactive group and the linking group, wherein the covalent linkage between at least one photoreactive group and the linking group is interrupted by at least one heteroatom. See U.S. Publ. Pat. App. No. 2011/0245367 (Kurdyumov, et al.), the disclosure of which is incorporated herein by reference. Further cross-linking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

Natural polymers can also be used to form the hydrophilic base coat. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

Substrates

The substrate can be formed from any desirable material, or combination of materials, suitable for use within the body. In some embodiments the substrate is formed from compliant and flexible materials, such as elastomers (polymers with elastic properties). Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, polyether-polyamide copolymers, and the like. The substrate can be made of a single elastomeric material, or a combination of materials.

Other materials for the substrate can include those formed of polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

Beyond polymers, and depending on the type of device, the substrate can also be formed of other materials such as metals (including metal foils and metal alloys) and ceramics.

Aqueous Carrier

In one embodiment, the delivery composition includes a hydrophobic active agent and a cationic delivery agent in a pharmaceutically acceptable aqueous carrier. As used herein, a "pharmaceutically acceptable carrier" refers to a carrier or diluent that does not cause significant irritation to an organism and does not abrogate the biological activity and properties of the administered composition. In one embodiment, the aqueous carrier includes water or buffered saline. In a more particular embodiment, the aqueous carrier includes deuterium-depleted water (DDW). In one embodiment, the hydrophobic active agent and/or the cationic delivery agent are suspended in water. In one embodiment, the carrier includes a minor amount (e.g., less than about 20%, 15%, 10%, 9%, 8%, 7%, 6%, 5%, 4%, 3%, 2% or 1%) of a biocompatible solvent. As used herein, the term "biocompatible solvent" refers to a solvent that is considered non-toxic and does not elicit an immunological response at the amounts included in the carrier. Examples of biocompatible solvents include, but are not limited to, ethanol, ethyl lactate, acetone, dimethylsulfoxide (DMSO), and combinations thereof. In one embodiment, the hydrophobic active agent is suspended in water as a coated therapeutic agent. In one embodiment, a mixing or agitation step can be performed in order to allow the hydrophobic active agent to interface with the cationic delivery agent. In some embodiments, the cationic delivery agent surrounds and/or encapsulates the particulate hydrophobic active agent to form a coated active agent particle.

In one embodiment, the pH of the composition is adjusted to at least about 5, 6 or 7 and up to about 7, 8 or 9.

Devices

It will be appreciated that embodiments herein include, and can be used in conjunction with, various types of devices including, but not limited to, drug delivery devices such as drug eluting balloon catheters, drug-containing balloon catheters, stents, grafts, and the like.

Some embodiments described herein can be used in conjunction with balloon expandable flow diverters, and self-expanding flow diverters. Other embodiments can include uses in contact with angioplasty balloons (for example, but not limited to, percutaneous transluminal coronary angioplasty and percutaneous transluminal angioplasty). Yet other embodiments can include uses in conjunction with sinoplasty balloons for ENT treatments, urethral balloons and urethral stents for urological treatments.

Other embodiments of the present disclosure can further be used in conjunction with micro-infusion catheter devices. In some embodiments, micro-infusion catheter devices can be used to target active agents to the renal sympathetic nerves to treat, for example, hypertension.

Embodiments included herein can also be used in conjunction with the application of various active agents to the skin (for example, but not limited to transdermal drug delivery).

Other exemplary medical applications wherein embodiments of the present disclosure can be used further encompass treatments for bladder neck stenosis (e.g. subsequent to transurethral resection of the prostrate), laryngotrachial stenosis (e.g. in conjunction with serial endoscopic dilatation to treat subglottic stenosis, treatment of oral cancers and cold sores and bile duct stenosis (e.g. subsequent to pancreatic, hepatocellular of bile duct cancer). By way of further example, embodiments herein can be used in conjunction with drug applicators. Drug applicators can include those for use with various procedures, including surgical procedures, wherein active agents need to be applied to specific tissue locations. Examples can include, but are not limited to, drug applicators that can be used in orthopedic surgery in order to apply active agents to specific surfaces of bone, cartilage, ligaments, or other tissue through physical contact of the drug applicator with those tissues. Drug applicators can include, without limitation, hand-held drug applicators, drug patches, drug stamps, drug application disks, and the like.

In some embodiments, drug applicators can include a surface having a hydrophilic polymer layer disposed thereon and coated therapeutic agent particles disposed on the hydrophilic polymer layer, the coated therapeutic agent particles comprising a particulate hydrophobic therapeutic agent; and a vinyl amine polymer disposed over the particulate hydrophobic therapeutic agent.

In use, various embodiments included herein can enable rapid transfer of therapeutic agents to specific targeted tissues. For example, in some embodiments, a care provider can create physical contact between a portion of a drug delivery device including a therapeutic agent and the tissue being targeted and the therapeutic agent will be rapidly transferred from the drug delivery device to that tissue. As such, precise control over which tissues the therapeutic agent is provided to can be achieved.

One beneficial aspect of various of the embodiments herein is that the therapeutic agent can be transferred from the drug delivery device or coating to the targeted tissue very rapidly. In some embodiments substantial transfer of the therapeutic agent from the drug delivery device or coating to the tissue occurs in 30 minutes or less. In some embodiments substantial transfer of the therapeutic agent from the drug delivery device or coating to the tissue occurs in 15 minutes or less. In some embodiments substantial transfer of the therapeutic agent from the drug delivery device or coating to the tissue occurs in 10 minutes or less. In some embodiments substantial transfer of the therapeutic agent from the drug delivery device or coating to the tissue occurs in 5 minutes or less. In some embodiments substantial transfer of the therapeutic agent from the drug delivery device or coating to the tissue occurs in 2 minutes or less. In some embodiments substantial transfer of the therapeutic agent from the drug delivery device or coating to the tissue occurs in 1 minute or less.

In some embodiments, medical devices that can pass through a lumen of a bodily structure are included herein. By way of example, medical devices in accordance with embodiments herein can include capsular devices for transitory placement within a lumen of the body.

Referring now to FIG. 16, the medical device 1602 includes a capsule housing 1604 and an at least one moveable element 1606. In this particular embodiment, two moveable elements 1606 are shown. However, it will be appreciated that the device can include any particular number of moveable elements. In some embodiments, the device can include from 1 to 20 moveable elements. In some embodiments, the moveable elements can be arranged radially around the outside of the capsule housing 1604. The medical device 1602 can have a total width 1608. In this view, the moveable elements are in a non-deployed position.

FIG. 16 also shows portions of a tissue 1610 and tissue walls 1612 that form a lumen into which the medical device 1602 is disposed. It will be appreciated that the tissue 1610 can be from various parts of the body. By way of example, the tissue walls 1612 can be walls lining: a portion of the vasculature within a body, a portion of any segment of the alimentary canal (including but not limited to the esophagus, the stomach, the small intestine, or the large intestine), a portion of the bile duct system, of the like. In some embodiments, the tissue 1610 can include smooth muscle tissue.

Referring now to FIG. 17, the medical device 1602 includes a capsule housing 1604 and an at least one moveable element 1606. In this view, the moveable elements are in a deployed position. The medical device 1602 has a total width 1608 that is larger than the width when the moveable elements were in a non-deployed position. FIG. 17 also shows the tissue 1610 and tissue wall 1612. With the moveable elements in a deployed position, a portion of moveable elements is in contact with the tissue walls 1612. As further described below, a coating, which can include various components (such as polymers, additives, excipients, and/or active agents) as described herein, can be disposed on the moveable elements. Thus, when the moveable elements are in contact with the tissue walls, then the coating which includes an active agent can also be in contact with the tissue walls so that the active agent can be delivered to the tissue walls.

It will be appreciated that the device 1602 can include various components. By way of example, the device 1602 can include components such as that described in U.S. Pat. Nos. 5,279,607, 7,797,033; and in U.S. Publ. App. No. 2010/0130837, the content of all of which is herein incorporated by reference. Referring now to FIG. 18, the medical device 1602 includes a capsule housing 1604, control circuitry 1814, disposed within the capsule housing 1604, and at least one moveable element 1606. The control circuitry 1814 can be configured to execute various functions to control the device. In some embodiments, the control circuitry 1814 can be configured to cause the moveable element to move between a deployed position and a non-deployed position. The medical device 1602 can also include telemetry circuitry 1816, which can be configured to receive and/or send information to an external device. The medical device 1602 can also include power circuitry 1818 including, but not limited to, components such as a battery, capacitor, or the like. The medical device 1602 can include moveable element actuator 1820. In some embodiments, the moveable element actuator 1820 can include a component to provide a motive force to cause the moveable elements 1606 to move between the deployed position and the non-deployed position. The actuator 1820 can include various components such as a solenoid, linear actuator, piezoelectric actuator, electric motors of various types including servo motors, and the like.

Referring now to FIG. 19, an embodiment of a moveable element 1606 is shown. The at least one moveable element 1606 can be a wing-shaped element 1922. The at least one moveable element 1606 can include a front portion 1924 and a back portion 1926. The front portion 1924 can serve as a pivot point with respect to the device 1602 in some embodiments.

Referring now to FIG. 20, the at least one moveable element 1606 includes a substrate 2028 and a coating 2030 disposed over the substrate 2028. The at least one moveable element 1606 can include outer surface 2032. In various embodiment, the coating 2030 is disposed on the outer surface 2032. The coating 2030 can include various components as described herein. In some embodiments, the coating can include a hydrophilic polymer layer and coated therapeutic agent particles. In some embodiments, the coated therapeutic agent particles can include a particulate hydrophobic therapeutic agent and a vinyl amine polymer component. The at least one moveable element 1606 can also include inner surface 2034. In some embodiments, the moveable element 1606 can have a curvature, such as shown in FIG. 20, which allows the moveable element 1606 to fit more tightly against the device 1602 when the moveable element 1606 is in a non-deployed position.

Referring now to FIG. 21, another embodiment of a moveable element 1606 is shown. The at least one moveable element 1606 can include a shaft 2136. The at least one moveable element 1606 can also include a paddle 2138. The at least one moveable element 1606 can include a front side 1924 and a back side 1926.

Method of Making

In one embodiment, the invention is directed towards methods of making the delivery compositions described herein. In one embodiment, the delivery composition includes a hydrophobic active agent and a cationic delivery agent in an aqueous carrier. In a more particular embodiment, the cationic delivery agent includes PEI. In another embodiment, the cationic delivery agent includes branched PEI. In a specific embodiment, the hydrophobic active agent is paclitaxel, sirolimus (rapamycin), everolimus, biolimus A9, zotarolimus, tacrolimus, and pimecrolimus and mixtures thereof.

In some embodiments, the hydrophobic active agent can be processed, for example, by milling of the active agent. In some embodiments, processing of the hydrophobic active agent can include crystallization. In other embodiments, processing of the hydrophobic active agent can include lyophilizing of the active agent.

In one embodiment, the hydrophobic active agent is suspended in an aqueous carrier such as water. By combining the hydrophobic active agent and a cationic delivery agent, coated active agent particles can be formed. By way of example, a cationic agent, in water or other aqueous solvent, can be added to a hydrophobic active agent suspension. In some embodiments, a mixing or agitation step can be performed in order to allow the hydrophobic active agent to interface with the cationic agent. In some embodiments, the cationic agent will surround or encapsulate the particulate hydrophobic active agent. In one embodiment, the hydrophobic active agent has a particle size of at least about 0.1 µm, 0.2 µm, 0.3 µm, 0.4 µm, 0.5 µm or 1 µm and less than about 10 µm, 5 µm, 4 µm, 3 µm, 2µm or 1 µm.

In one embodiment, an active agent solution or suspension is first made by combining a hydrophobic active agent with an aqueous solvent to form an active agent solution or suspension. After the active agent solution or suspension is formed, the cationic delivery agent is added to form a delivery composition. In one embodiment, the hydrophobic active agent is crystallized before it is combined with the aqueous solvent to form the active agent solution or suspension. In another embodiment, the hydrophobic active agent is amorphous when it is combined with the aqueous solvent to form the active agent solution or suspension. In another embodiment, the cationic delivery agent is combined with an aqueous solvent to form a cationic delivery agent solution before the cationic delivery agent is combined with the active agent solution or suspension. In one embodiment, the pH of the cationic delivery agent solution is buffered to between about 5 and 9 before the cationic delivery agent is added to the active agent solution or suspension.

In another embodiment, the delivery composition is made by combining the hydrophobic active agent and the cationic delivery agent to form an active agent mixture. In one embodiment, the active agent mixture comprises solid hydrophobic active agent and pure or neat cationic delivery agent. In one embodiment, the solid hydrophobic active agent is crystalline. In another embodiment, the solid hydrophobic active agent is amorphous. In one embodiment, the method includes a step of crystallizing the hydrophobic active agent before it is combined with the cationic delivery agent. In another embodiment, the hydrophobic active agent is amorphous when it is combined with the cationic delivery agent. In one embodiment, the method includes a step of crystallizing the mixture of solid hydrophobic active agent and pure or neat delivery agent before combining the mixture with an aqueous carrier to form the delivery composition. In another embodiment, a mixture containing crystalline hydrophobic active agent and pure or neat delivery agent is combined with the aqueous carrier to form the delivery composition. In general, when solid hydrophobic active agent and solid hydrophobic cationic delivery agent are combined to form a mixture, the ratio of solid hydrophobic active agent:cationic delivery agent is less than about 1:5 to prevent the cationic delivery agent from solubilizing the hydrophobic active agent.

In various embodiments, coating solutions herein, both as compositions and as used with methods herein, can have a pH that is in a range of about 2.0 to about 8.0. In various embodiments, the pH of one or more coating solutions herein can be in a range having a lower bound and an upper bound, wherein the lower bound of the range can be any of 2.0, 2.5, 3.0, 3.5, 4.0, 4.5, 5.0, 5.5, 6.0, 6.5, 7.0, or 7.5 and the upper bound of the range can be any of 2.5, 3.0, 3.5, 4.0, 4.5, 5.0, 5.5, 6.0, 6.5, 7.0, 7.5, 8.0, wherein the upper bound of the range is higher than the lower bound of the range.

Kits and Articles of Manufacture

Another embodiment of the invention is directed towards kits and articles of manufacture. In particular, the present invention provides kits or packages including the delivery compositions described herein. In one embodiment, the invention provides a kit that includes one or more of the components of the delivery composition. As used herein "components of the delivery composition" can refer to one or more hydrophobic active agents, one or more cationic delivery agents, one or more pharmaceutically acceptable aqueous carriers, and any other additive, diluent, excipient, adjuvant, emulsifier, buffer, stabilizer, preservative included in the delivery composition. In one embodiment, the kit includes one or more hydrophobic active agents and one or more cationic delivery agent and instructions for combining the hydrophobic active agent and cationic delivery agent to form a delivery composition suitable for local administration. In one embodiment, the cationic delivery agent includes PEI. In another embodiment, the cationic delivery agent includes branched PEI. In a specific embodiment, the hydrophobic active agent is paclitaxel, sirolimus (rapamycin), everolimus, biolimus A9, zotarolimus, tacrolimus, and pimecrolimus and mixtures thereof.

In one embodiment, the kit includes at least about 1 mg/ml and up to about 25 mg/ml cationic delivery agent and at least about 5 mg/ml and up to about 125 mg/ml hydrophobic active agent, wherein the components are packaged individually, or combined, for example as a mixture of solids or as a liquid solution or suspension. In one embodiment, the kit includes at least about 1 mg/ml, 2 mg/ml, 3 mg/ml, 4 mg/ml, 5 mg/ml, or 10 mg/ml, 15 mg/ml, 20 mg/ml, or 25 mg/ml or up to about 25 mg/ml, 50 mg/ml, 75 mg/ml, 100 mg/ml, 125 mg/ml or 150 mg/ml hydrophobic active agent. In one embodiment, the kit includes at least about 0.1 mg/ml, 0.5 mg/ml, 1 mg/ml, 2 mg/ml, 3 mg/ml, 4 mg/ml, or 5 mg/ml and up to about 5 mg/ml, 10 mg/ml, 15 mg/ml, 20 mg/ml or 25 mg/ml cationic delivery agent. In one embodiment, the kit includes cationic delivery agent:hydrophobic active agent at a ratio of at least 1:25, for example, between about 1:1 and about 1:25, or at least about 1:2, 1:5 or 1:10 and up to about 1:10, 1:15, 1:20 or 1:25.

A number of packages or kits are known in the art for the use in dispensing pharmaceutical agents. The components of the delivery composition (for example, the hydrophobic active agent, the cationic delivery agent, the pharmaceutically acceptable aqueous carrier and/or any other additives) may be individually formulated or co-formulated and filled into suitable containers such as syringes, ampoules, or vials. It is envisioned that the aqueous carrier also may be provided in another container in the kit. The kits of the present invention also will typically include a means for containing the vials in close confinement for commercial sale such as, for example, injection or blow-molded plastic containers into which the desired vials are retained. In one embodiment, the kit includes an instrument for administration of the delivery composition, such as an inhalant, syringe, pipette, eye dropper, measuring spoon, or other such instrument, which can be used to apply the delivery composition to the desired tissue or organ of the patient.

In one embodiment, the kit provides one or more of the components of the delivery composition and instructions for combining the components for administration. In one embodiment, one or more of the components of the delivery composition in the kit is provided in dried or lyophilized forms. In one embodiment, the hydrophobic active agent, the cationic delivery agent, or both are provided as dried solids, individually or as a mixture. In another embodiment, the hydrophobic active agent, the cationic delivery agent, or both are provided as lyophilized solids, individually or as a mixture. In one embodiment, the hydrophobic active agent, the cationic delivery agent, or both are provided as amorphous solids, individually or as a mixture. In another embodiment, the hydrophobic active agent, the cationic delivery agent, or both are provided as crystalline solids, individually or as a mixture. When one or more components are provided as a dried solid, reconstitution generally is by the addition of a suitable aqueous carrier. In one embodiment, the aqueous carrier is water.

In another embodiment, one or more of the components of the delivery composition is provided as a solution or suspension. In one embodiment, the hydrophobic active agent, the cationic delivery agent, or both are provided as a solution or suspension, individually or as a mixture. For example, if individually provided, two solution components can be separated in a dual delivery syringe for ease of delivery to the site (for example dual delivery syringes and mini-dual delivery syringes available from Plas-Pak, Inc, Norwich, Conn.). In some instances, contents of a dual delivery syringe can be lyophilized to provide for a dual delivery syringe that contains a solution or suspension in one side and a dry powder in the other. Alternatively, the dual delivery syringe can contain lyophilized dry powder in both sides of the dual syringe. It is well known in the art that the lyophilized powder can be reconstituted at the point of use with physiologically acceptable fluid, such as phosphate buffered saline (PBS).

In one embodiment, one or more of the components of the delivery composition are provided as a dried solid in a container, individually or as a mixture, for example, as a crystallized solid or an amorphous solid, and are reconstituted with a pharmaceutically acceptable carrier prior to administration. In other embodiments, one or more of the components of the delivery composition are provided in as a liquid, in a container, individually or as a mixture, that may be administered with or without dilution. In one embodiment, one of the components of the delivery composition may be provided in solid form, which, prior to administration to a patient, is reconstituted with an aqueous liquid and another component of the delivery composition may be provided as a liquid solution or suspension, wherein the components are combined prior to administration. Each container may contain a unit dose of the active agent(s).

Methods of Use

The invention also provides a method for delivering a therapeutically effective amount of a hydrophobic active agent to a tissue, organ or organ system of a patient. In a more particular embodiment, the invention provides a method for local delivery of a therapeutically effective amount of a hydrophobic active agent to a solid tissue or organ of a patient. While not wishing to be bound by theory, it is believed that combining the hydrophobic active agent with a cationic delivery agent such as PEI improves adhesion of active agent to the tissue or organ surface, thereby increasing bioavailability and uptake of the hydrophobic active agent by tissue or organ to which it is applied. The cationic delivery agent may also disrupt some of the junctions between cells to increase permeability and allow the active agent to penetrate into the tissue or organ. It appears that the ability of the cationic delivery agent to improve therapeutic performance is most pronounced when used in combination with hydrophobic active agents. It is believed that more soluble hydrophilic active agents are more easily washed away from the surface of the tissue or organ by physiological fluids.

As used herein, the term "tissue" refers to an ensemble of similar cells from the same origin, that together carry out a specific function. Animal tissues can be grouped into four basic types: connective, muscle, nervous, and epithelial. Connective tissues are fibrous tissues made up of cells scattered throughout an extracellular matrix. Connective tissue helps maintain the shape of organs and helps holds them in place. Bone is an example of connective tissue. Muscle tissue functions to produce force and cause motion, either locomotion or movement within internal organs. Muscle tissue can be separated into three categories: visceral or smooth muscle, which is found in the inner linings of organs; skeletal muscle, in which is found attached to bone providing for gross movement; and cardiac muscle which is found in the heart. Nervous tissue functions to transmit messages in form of impulses. In the central nervous system, nervous tissue forms the brain and spinal cord. In the peripheral nervous system, nervous tissue forms the cranial nerves and spinal nerves. Epithelial tissue helps to protect organisms from microorganisms, injury, and fluid loss. The cells comprising an epithelial layer are linked via semipermeable, tight junctions; hence, this tissue provides a barrier between the external environment and the organ it covers. In addition to this protective function, epithelial tissue may also be specialized to function in secretion and absorption. Epithelial tissues include cells that cover organ surfaces such as the surface of the skin, the airways, the reproductive tract, and the inner lining of the digestive tract.

As used herein, the term "organ" refers to a functional grouping of one or more tissues. Functionally related organs may cooperate to form organ systems. Examples of organs and organ systems found in mammals include, but are not limited to: the cardiovascular system, which includes organs such as the heart and blood vessels; the digestive system, which includes organs such as salivary glands, esophagus, stomach, liver, gallbladder, pancreas, intestines, colon, rectum and anus; the endocrine system, which includes endocrine glands such as the hypothalamus, pituitary gland, pineal body or pineal gland, thyroid, parathyroid and adrenal glands; the excretory system, which includes organs such as kidneys, ureters, bladder and urethra; the immune system, which includes tonsils, adenoids, thymus and spleen; the integumentary system, which includes skin, hair and nails; the muscular system, which includes voluntary and involuntary muscles; the nervous system, which includes brain, spinal cord and nerves; the reproductive system, which includes the sex organs, such as ovaries, fallopian tubes, uterus, vagina, mammary glands, testes, vas deferens, seminal vesicles, prostate and penis; the respiratory system, which includes the pharynx, larynx, trachea, bronchi, lungs and diaphragm; and the skeletal system, which includes bones, cartilage, ligaments and tendons. As used herein, the terms "tissue" and "organs" refer to solid tissues or organs, rather than blood or other biological liquids such as spinal fluid, amniotic fluid or peritoneal fluid.

As used herein, an "individual" or a "patient" is a vertebrate, for example, a mammal. The term "mammal" can also refer to any animal classified as a mammal, including humans, domestic and farm animals, and zoo, sports, or pet animals, such as dogs, horses, cats, cows, etc. In a more particular embodiment, the mammal is human.

The term "effective amount" refers to an amount effective, at dosages and for periods of time necessary, to achieve the desired therapeutic or prophylactic result. A "therapeutically effective amount" of the delivery composition of the invention may vary according to factors such as the disease state, age, sex, and weight of the individual, and the ability of the substance/molecule, agonist or antagonist to elicit a desired response in the individual. A therapeutically effective amount is also one in which any toxic or detrimental effects of the composition are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount may be less than the therapeutically effective amount.

In one embodiment, the invention provides a method for treating a tissue or organ of a patient. As used herein, the terms "treat", "treating" and "treatment" refer to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishing of any direct or indirect pathological consequences of the disease, decreasing the rate of disease progression, amelioration or palliation of the disease state, and remission or improved prognosis. As used herein, the terms "prevent", "preventing" and "prevention" refer to a method for preventing an organism from acquiring a disorder.

The delivery composition may be a topical, syringable, or injectable formulation; and is suitable for local delivery of the active agent. For topical administration, the delivery composition is applied directly where its action is desired. Methods for topical delivery include the use of ointments, creams, emulsions, solutions, suspensions and the like. In other embodiments, the delivery composition is administered by application through a cannula, by injection, or as part of a lavage. Compositions for these types of local delivery can include solutions, suspensions and emulsions.

Examples of local administration include, but are not limited to, epicutaneous administration (i.e., application onto the skin); inhalation, for example, with asthma medications; as an enema for local administration to the bowel; ocular, for example, as eye drops for local administration to the conjunctiva; aural, for example, as ear drops; or intranasal. In other embodiments, an active agent can be administered locally from a device such as a balloon catheter. In another embodiment, local administration includes the lavage of an open wound, the lavage containing delivery compositions described herein with antimicrobials or other wound healing medicaments. In a more particular embodiment, local administration includes oral lavage, for example, a mouthwash.

In some embodiments, the delivery composition can be administered using a balloon catheter. The delivery composition can be infused through a lumen or lumens of a balloon catheter to administer the composition to the desired site where the drug effect is warranted. For example, the site can be a segment of an artery, vein or neurovascular. The method allows for isolation and subsequent perfusion of the target organ (e.g. for tumor treatment). One specific embodiment of administration can be the use of a dual occlusion balloon (e.g. TAPAS balloon system available from Spectranectics International, BV, Leusden, The Netherlands) for precise targeting of a treatment area (e.g. intra-arterially). Use of delivery compositions as disclosed herein can increase targeting of the treatment area with the drug being delivered, thus further minimizing unwanted systemic effects of the drug. Other balloon catheter methods of use include balloon sinuplasty (e.g. Relieva® and Relieva Ultirra™; available from Acclarent, Menlo Park, Calif.)

In yet other embodiments, a medical device such as a balloon catheter can be coated with the delivery composition described herein. In one embodiment, the balloon catheter can be coated in a collapsed state. In another embodiment, the balloon catheter can be coated in a partially or fully expanded state. In one embodiment, the balloon catheter can be coated with the coating materials described herein and a bioactive material such as a chemical ablative (e.g. vincristine, paclitaxel) and further used for renal artery denervation therapy for hypertension.

Delivery compositions of the present disclosure can also be used in conjunction with microinfusion catheters. Such catheters can be used to deliver drug, for example, for renal denervation for direct infusion into the vessel wall (Bullfrog® and Cricket™ microinfusion catheters available from Mercator MedSystems, Inc.). Microinfusion catheters with delivery compositions of the present disclosure can also be used to form an embolic block, such as in neurovascular applications or treatment of the vascular supply of tumors. Other neurovascular methods of use include, but are not limited to, brachytherapy treatment for brain cancer applications (GliaSite Radiation Therapy System available from IsoRay, Medical, Richland, Wash.).

Delivery compositions described herein can also be used in connection with treating stenosis such as bladder neck stenosis (BNS), a complication associated with transurethral resection of the prostate; laryngotracheal stenosis, for example, in conjunction with serial endoscopic dilation to treat subglottic stenosis; and bile duct stenosis, for example, subsequent to pancreatic, hepatocellular or bile duct cancer.

Delivery compositions described herein can be combined with treatments that use RF-susceptible microparticles to improve uptake of the microparticles in the tissue at the site of the tumor or other targeted organ. Other embodiments for topical administration include, but are not limited to, oral cavity delivery of chemotherapeutics, for example with mouthwashes. Additionally, studies have shown that delivery of rapamycin to the oral cavity can prevent radiation-induced mucositis and that it can be desirable to reduce the systemic levels of rapamycin to avoid toxicities associated with the drug (*Cell Stem Cell*, Sep. 7, 2012, Vol. 11:3, pp. 287-288).

Delivery compositions described herein can be used to increase drug-uptake in the lung. One embodiment envisioned to be used for delivery compositions for inhalation therapy can be a metered-dose inhaler (available from 3M Company, St. Paul, Minn.). Compositions described herein can increase drug uptake in the lung to provide for improved speed of drug effect, an important aspect when treating disease states such as asthma.

Other methods of use include treatment of joint disorders (e.g. arthritis). Local injections of drug (e.g. cortisone) are desirable to be kept at the site of the affected joint for extended term.

Some embodiments of the method of use include localized treatment of the lining of the esophagus. Barrett's esophagus (pre-cancer esophagus lining) after BARRX treatment (ablation) requires delivery of local healing agents to the affected site for improved outcomes. Delivery compositions disclosed herein can increase uptake of healing agents by the treated esophagus.

Other exemplary methods of use for the local delivery compositions described herein include direct injections into a cancerous tumor, intraperitoneal tumor treatment, and sclerotherapy. Additionally, percutaneous delivery systems of biologics for the treatment of cardiovascular disease can use the delivery composition of the present disclosure. Treatments such as those under the trade name JVS-100, promotes tissue repair through recruitment of endogenous stem cells to the damaged organ (available from BioCardia, Inc, San Carlos, Calif.). These devices allow delivery into the heart using the Helical Infusion Catheter for transendocardial intramyocardial injection of therapies (also from BioCardia).

Additional Embodiments

As described above, some embodiments can include a hydrophilic base coat or layer. In some embodiments, a hydrophilic polymer solution is formed by combining a hydrophilic polymer with one or more solvents. Exemplary hydrophilic polymers are described in greater detail above. The hydrophilic polymer solution can then be applied to a suitable substrate, such as an expandable balloon disposed on a catheter shaft. Many different techniques can be used to apply the hydrophilic polymer solution to the substrate. By way of example, exemplary techniques can include brush coating, drop coating, blade coating, dip coating, spray coating, micro-dispersion, and the like.

In some embodiments, such as where a photo-polymer is used to form the hydrophilic layer, an actinic radiation application step can be performed in order to activate latent photoreactive groups on the hydrophilic polymer or on a cross-linker in order to covalently bond the hydrophilic polymer the substrate surface. By way of example, after applying the hydrophilic polymer solution to the substrate, the device can be subjected to UV exposure at a desirable wavelength for a period of time.

Next a hydrophobic active agent can be obtained and processed in order to prepare it for deposition. In some embodiments, processing of the hydrophobic active agent can include steps such as milling of the active agent. In some embodiments, processing of the hydrophobic active agent can include steps such as recrystallization of the active agent. In some embodiments, processing of the hydrophobic active agent can include lyophilizing of the active agent.

In various embodiments, the hydrophobic active agent, as a particulate, can be suspended in water. Using the hydrophobic active agent and a vinyl amine polymer, coated therapeutic agent particles can be formed. By way of example, a vinyl amine polymer, in water or a different solvent, can be added to the hydrophobic active agent suspension. In various embodiments, a mixing or agitation step can be performed in order to allow the hydrophobic active agent to interface with the vinyl amine polymer. In some embodiments, the vinyl amine polymer will surround the particulate hydrophobic active agent.

In some embodiments, a nucleic acid solution can be added to the mixture, either before or after addition of the vinyl amine polymer and the mixing/agitation steps. In some embodiments, an additive component such as those described above can be added to the mixture. The mixture can be applied to the substrate of a device, either directly or on top of a hydrophilic base coat. By way of example, exemplary techniques for application can include brush coating, drop coating, blade coating, dip coating, spray coating, micro-dispersion and the like.

The solution including the vinyl amine polymer and the hydrophobic active agent can include various amounts of the active agent. By way of example, the solution can include from 1 to 500 mg/ml of the active agent in some embodiments. In some embodiments the solution can include from 10 to 250 mg/ml of the active agent. In some embodiments, the solution can include form 50 to 200 mg/ml. In some embodiments, the solution can include form 100 to 200 mg/ml. In some embodiments, the solution can include form 100 to 180 mg/ml. In some embodiments, the solution can include about 10, 20, 30, 40, 50, 60, 70, 80, 90, 100, 110, 120, 130, 140, 150, 160, 170, 180, 190, 200, 210, 220, 230, 240, or 250 mg/ml of the active agent wherein each of those amounts can serve as the upper or lower bound of a range.

After application, the composition can be allowed to dry. In the context of drug eluting balloon catheters or a drug-containing balloon catheter, for example, the balloons can be folded, pleated and sheathed in a sheath. In some embodiments, balloons can be placed in an oven for a period of time.

In some embodiments of the present disclosure, an active agent that is not hydrophobic can be modified to be essentially hydrophobic for disposition on the hydrophilic polymer layer. Exemplary modifications can include the preparation of prodrugs, whereby the hydrophobicity of the active agent can be modified by covalent linkage to a polymer. Other exemplary prodrugs can include an active agent that is formed in-situ by bond cleavage of the prodrug. Other exemplary modifications can include, but are not limited to, particles (e.g. nanoparticles or microparticles) containing the active agent encapsulated in a hydrophobic polymer. In some embodiments the hydrophobic polymer can be biodegradable, releasing the active agent upon delivery to the targeted tissue. Other exemplary modifications can include, but are not limited to, micelles or other constructs of the like with altered hydrophobicity, formed as a result of the interaction between the active agent and a lipid additive.

The present invention may be better understood with reference to the following examples. These examples are intended to be representative of specific embodiments of the invention, and are not intended as limiting the scope of the invention.

EXAMPLES

As used in the Examples, the term "jar-Milled Paclitaxel" refers to Paclitaxel (LC laboratories) that was suspended in water at 65 mg/mL and milled using 5 mm stabilized zirconia 5×5 mm cylindrical beads (Stanford Materials Corp). After milling for 18 hours the slurry was removed from the beads and lyophilized. The term "sonicated Paclitaxel" refers to Paclitaxel crystals that were obtained by suspending paclitaxel (LC Laboratories) in water at 50 mg/mL. The paclitaxel was micronized using a sonic probe for 30 seconds, and leaving the resulting suspension for three days at room temperature on an orbital shaker with a 1 hour sonication treatment per day in a sonic bath over the course of the three days. The mixture was lyophilized.

Example 1

Polyethylenimine (PEI) Mediated Transfer of Paclitaxel (PTX) to Surfaces

Delivery of paclitaxel to surfaces with or without seeded endothelial cells was studied in-vitro using untreated 24-well polystyrene tissue culture plates (TCPS); Matrigel™ coated 24-well cell culture plates (BD Matrigel™ Matrix Thin-Layer cell; available from Becton Dickinson Biosciences, Franklin Lakes, N.J.), or 24-well cell culture plates treated with heparin-containing HP01 coating or collagen containing CL01 coating (available from SurModics, Eden Prarie, Minn.). Human coronary endothelial cells (HCAECs, available Lonza, Walkersville, Md.) were cultured in EGM™-2MV growth media (available from Lonza, Walkersville, Md.). One day prior to paclitaxel transfer studies, cells were seed in the various culture plates at 50,000 cells per well in 0.5 mL of medium. Suspensions of paclitaxel (available from LC Laboratories, Woburn, Mass.) in water were prepared at 55.2 mg/ml paclitaxel with or without PEI (available from Polysciences, Warrington, Pa., MW=750 kDa) at 4.8 mg/ml. The suspensions were sonicated briefly. Resulting suspensions (6.7 µL) were added to cell media (100 µL) and put in the cell culture plates and incubated for 3 minutes. Suspensions were also added to the different 24-well plates with 100 µL medium (100 µL) but without seeded cells. After incubation plates were rinsed three times with phosphate buffered saline (500 µL per well) and then allowed to dry overnight. Paclitaxel remaining in plates as a result of adhesion was dissolved in 250 µL methanol and quantified by HPLC. The amount of transferred paclitaxel is shown in FIG. 1.

Example 2

Delivery of Paclitaxel to Surfaces with or without Seeded Endothelial Cells

Figure 2:
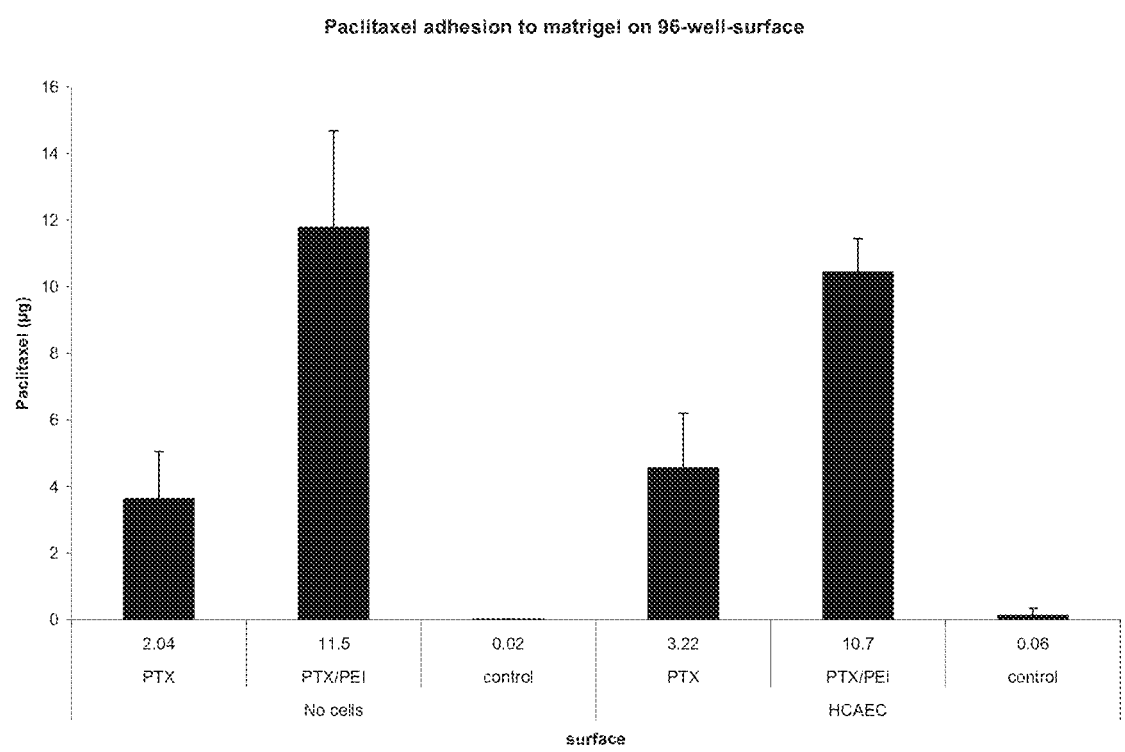
FIG. 2 is a graph showing the amount of paclitaxel transferred to Matrigel™ surfaces with or without seeded endothelial cells in the presence or absence of PEI.

Delivery of paclitaxel to surfaces with or without seeded endothelial cells was studied in-vitro using Matrigel™ coated 96-well cell culture plates (BD Matrigel™ Matrix Thin-Layer cell, available from Becton Dickinson Biosciences, Franklin Lakes, N.J.). Human coronary endothelial cells (HCAECs, available from Lonza, Walkersville, Md.) were cultured in EGM™-2MV growth media (available from Lonza, Walkersville, Md.). One day prior to paclitaxel transfer studies, cells were seed in the various culture plates at 20,000 cells per well in 0.2 mL of medium. Suspensions of paclitaxel (LC Laboratories, Woburn, Mass.) in water were prepared at 11 mg/ml paclitaxel with or without PEI (available from Polysciences, Warrington, Pa.; MW=750 kDa) at 1 mg/ml. Suspensions were sonicated briefly prior to use. Resulting suspensions (5 µL) were added to 0.1 mL of cell media and put in the cell culture plates and incubated for 3 minutes. Suspensions were also added to the Matrigel™ coated plate with 0.1 mL medium but without seeded cells. After incubation plates were rinsed three times with phosphate buffered saline (0.2 mL per well) and then allowed to dry overnight. Paclitaxel remaining in plates as a result of adhesion was dissolved in 250 µL methanol/0.1% acetic acid and quantified by HPLC. The amount of transferred paclitaxel is shown in FIG. 2.

Example 3

Figure 3:
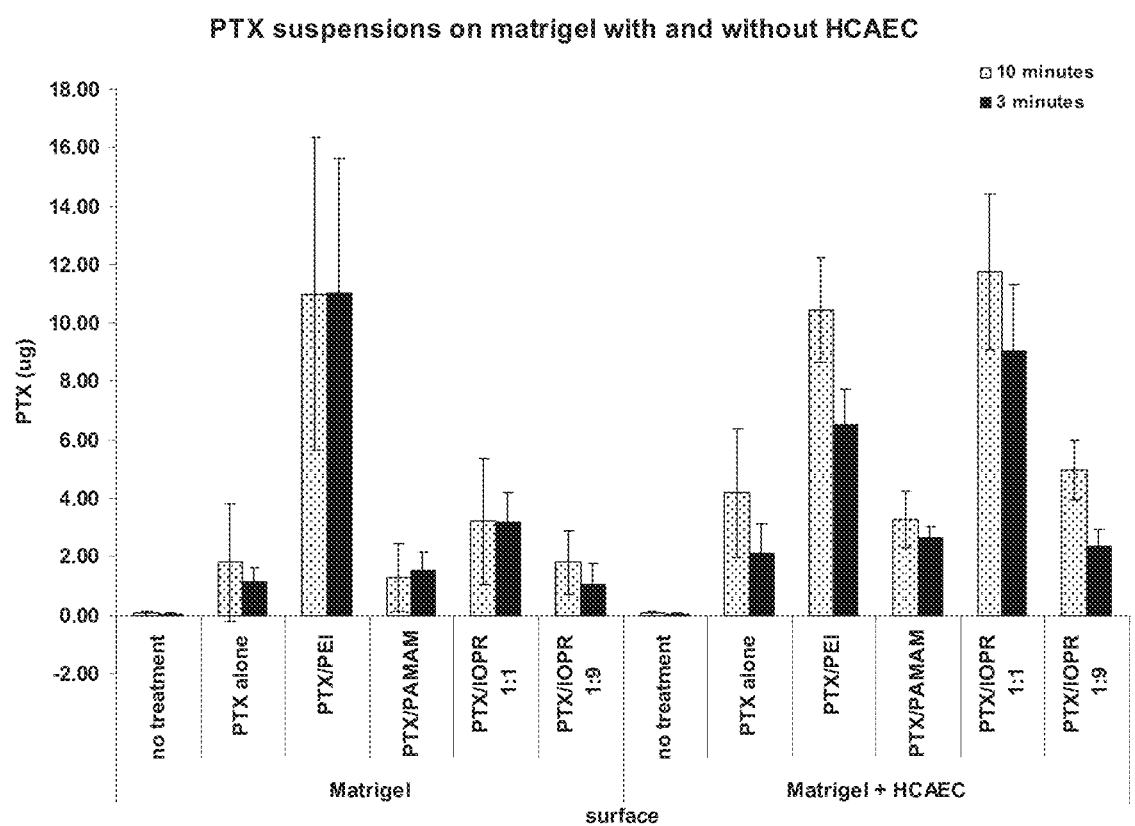
FIG. 3 is a graph showing delivery of paclitaxel to endothelial cells and tissues using cells grown on Matrigel™ coated cell culture plates in the presence or absence of PEI and other excipients such as radio-opaque iopromide.

Polyethyleneimine (PEI) Mediated Transfer of Paclitaxel (PTX) to Endothelial Cell Surface or Extracellular Matrix Surfaces Delivery of paclitaxel to endothelial cells and tissue was studied in vitro using cells grown on Matrigel™ coated cell culture plates. Human coronary endothelial cells (HCAECs, Lonza, Walkersville, Md.) were cultured in EGM™-2MV growth media (Lonza, Walkersville, Md.). One day prior to paclitaxel transfer studies, cells were seed in 96 well BD Matrigel™ Matrix Thin-Layer cell culture plates at 20,000 cells per well in 0.2 mL of medium. Suspensions of paclitaxel (LC Laboratories, Woburn, Mass.) in water were prepared at 11 mg/ml paclitaxel and with PEI (Polysciences, Warrington, Pa.; MW=750 kDa) or PAMAM, ethylene diamine core, gen 4, dendrimer (Sigma, Milwaukee, Wis.; 14,214 Da) at 0.96 mg/mL (92:8 w/w ratio) or iopromide at 11 mg/mL (IOPR, 1:1 w/w ratio). Suspensions were sonicated briefly prior to use. Resulting suspensions (5 µL) were added to the cell culture plates and incubated for 3 or 10 minutes. Suspensions were also added to Matrigel™ coated plates with medium but without cells. After incubation plates were rinsed three times with phosphate buffered saline (200 µL per well) and then allowed to dry overnight. Paclitaxel remaining in plates was dissolved in methanol (250 µL) and quantified by HPLC. The amount of transferred paclitaxel is shown in FIG. 3.

Example 4

Adhesion of Paclitaxel to Surfaces in the Presence of Heparin

Figure 4:
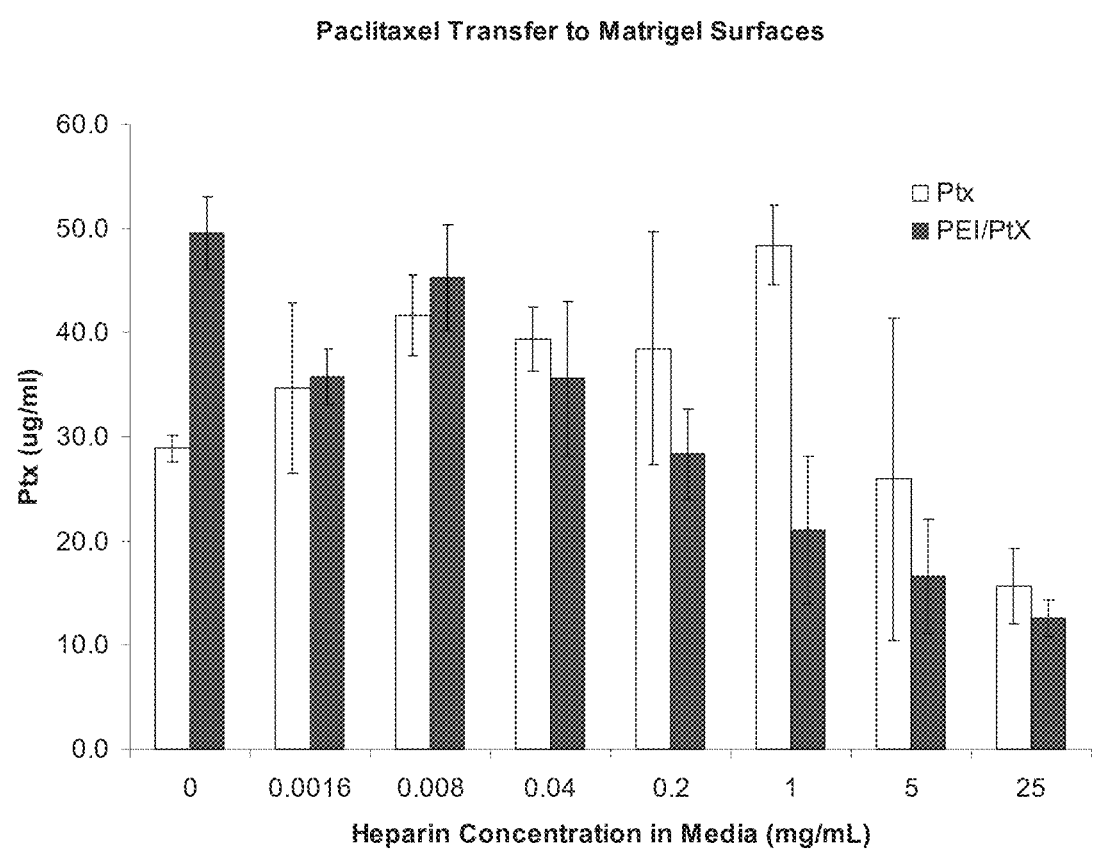
FIG. 4 is a graph showing the amount of paclitaxel transferred to Matrigel™ surfaces in the presence of varying concentrations of heparin in the presence or absence of PEI.
Figure 5:
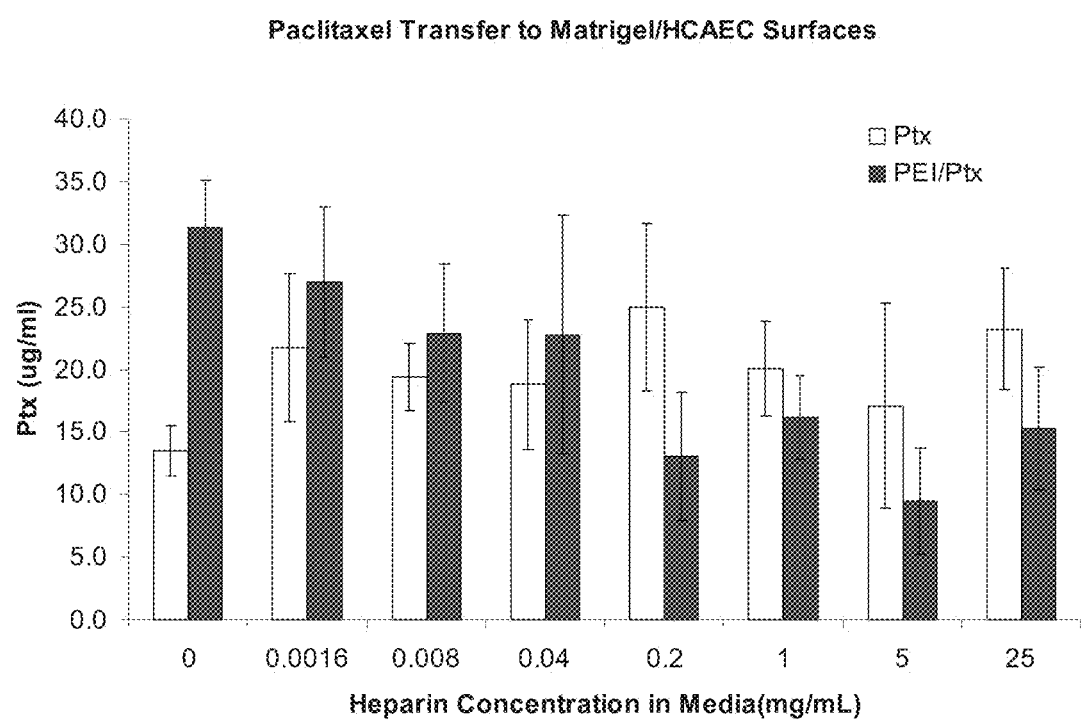
FIG. 5 is a graph showing the amount of paclitaxel transferred to Matrigel™/HCAEC surfaces in the presence of varying concentrations of heparin in the presence or absence of PEI.

Adhesion of paclitaxel to surfaces in the presence of heparin at varied concentrations with or without seeded endothelial cells was studied in-vitro using Matrigel™ coated 96-well cell culture plates (BD Matrigel™ Matrix Thin-Layer cell, BD Biosciences, San Jose, Calif.). Human coronary endothelial cells (HCAECs, Lonza, Walkersville, Md.) were cultured in EGM™-2MV growth media (Lonza, Walkersville, Md.). One day prior to paclitaxel transfer studies, cells were seed in the various culture plates at 20,000 cells per well in 0.2 mL of medium. Prior to adding paclitaxel, heparin (Sodium Salt, Celsus, Cincinnati, Ohio) was dissolved in growth medium at concentrations of 25, 5, 1, 0.2, 0.04, 0.008 and 0.0016 mg/ml and media in cell culture plates was replaced with heparin containing medium. Suspensions of paclitaxel (LC Laboratories, Woburn, Mass.) in water were prepared at 11 mg/ml paclitaxel with or without PEI (Polysciences, Warrington, Pa.) at 1 mg/ml. Suspensions were sonicated briefly prior to use. 5 µL of suspensions were added to the growth media in plates with and without cells and incubated for 4 minutes. After incubation plates were rinsed three times with phosphate buffered saline (0.2 mL per well) and then allowed to dry overnight. Paclitaxel remaining in plates as a result of adhesion was dissolved in methanol (60 µL) and quantified by HPLC. The amount of transferred paclitaxel with and without PEI and varying heparin concentrations is shown in FIGS. 4 and 5.

Example 5

Adhesion of Paclitaxel to Surfaces with or without Seeded Endothelial Cells

Figure 6:
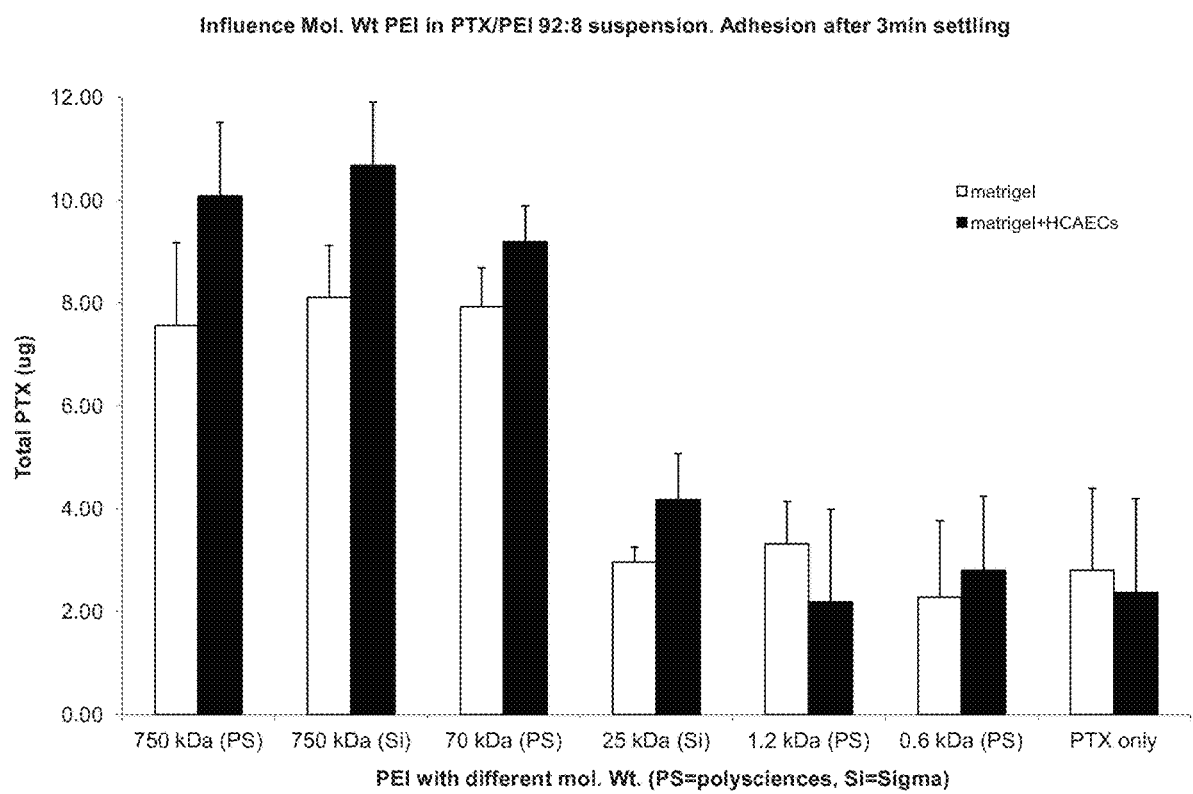
FIG. 6 is a graph showing the influence of molecular weight in adhesion of paclitaxel to surfaces with or without seeded endothelial cells.

Adhesion of paclitaxel to surfaces with or without seeded endothelial cells was studied in-vitro using Matrigel™ coated 96-well cell culture plates (BD Matrigel™ Matrix Thin-Layer cell). Human coronary endothelial cells (HCAECs, Lonza, Walkersville, Md.) were cultured in EGM™-2MV growth media (Lonza). One day prior to Paclitaxel transfer studies, cells were seeded in wells of column 7 to 12 of the culture plate at 20,000 cells per well in 0.2 mL of medium. After 24 hours incubation the medium was replaced with 100 ul fresh medium in all wells. Suspensions of Paclitaxel (LC Labs, 'sonicated') in aqueous branched PEI solutions were prepared at 11 mg/ml paclitaxel and PEI at 1 mg/ml. Branched PEI of different molecular weights were used: 750 kDa from both polysciences and Sigma, 70 kDa and 25 kDa from Sigma, 1200 Da and 600 Da from polysciences. All suspensions were sonicated briefly prior to use to ensure that all components were well distributed. In 12 wells per formulation (6 with and 6 without HCAEC seeded on top of the matrigel): 5 μL of the suspension was added to 0.1 mL of cell media. The plate was incubated for 3 minutes during which time the suspension was allowed to settle. After incubation the plate was rinsed three times with phosphate buffered saline (0.2 mL per well) and then allowed to dry overnight. Paclitaxel remaining in the plate as a result of adhesion was dissolved in 250 μL methanol/0.1% acetic acid and quantified by HPLC. The amount of transferred paclitaxel is shown in FIG. 6.

Example 6

Preparation of Materials

A. Preparation of (NVF-Co-NVP) Polymers A-D (Varying Molar Ratios of 1-Vinyl-2-Pyrrolidinone (NVP) and N-Vinylformamide (NVF))

Deionized water (72.2 g), N-vinylformamide (NVF, 5.85 g; available from Sigma Aldrich, Milwaukee, Wis.), N-vinylpyrrolidone (NVP, 9.14 g; available from Sigma Aldrich), and 2,2'-Azobis(2-methylpropionamidine)dihydrochloride (Vazo 56WSP; 0.192 g; available from Sigma-Aldrich) were placed in a 100 ml bottle with screw top cap. The solution was sparged with nitrogen for 10 minutes. The jar was capped and the solution was rotated in an oven at 55° C. overnight. A portion of the ensuing aqueous solution (~6.7%) was placed in dialysis tubing (MWCO 12-14 kDa; SPECTRA/POR® available from VWR, Radnor, Pa.) and dialyzed against water for 3 days. The dialyzed solution was lyophilized following 5 stages at the temperatures, pressures and times listed below in Table 2. A white solid (0.92 g) resulted.

TABLE 2

| | Stages | | | | |
|---|---|---|---|---|---|
| | 1 | 2 | 3 | 4 | final |
| Temperature (° C.) | −10 | 0 | 10 | 25 | 25 |
| Pressure (milltorr) | 400 | 200 | 100 | 50 | <20 |
| Time (hours) | 3 | 3 | 3 | 3 | >5* |

PVP (4.0 g; K-30; available from BASF, Port Arthur, Tex.) was dissolved in DI water (19.2 mL). A proton NMR was recorded for the PVP solution. The solution was treated with NaOH (0.15 g. of 50% aq.) and rotated in an oven at 80° C. overnight. The polymer solution was neutralized using HCl conc (0.2 mL; final pH=3-4). After neutralization the solution was difiltered using 10 kDa membrane (0.10 m² pellicon mini cassette; available from Millipore; Billerica, Mass.) against DI water. The solution was lypholized as described above to yield 3.12 g white solid. A proton NMR was recorded for the PVP treated with NaOH. In comparing the proton NMR spectrum of PVP against the proton NMR spectrum of PVP treated with NaOH, no differences could be seen between the spectra.

Four co-polymers of various monomer ratios were made as shown in Table 3.

TABLE 3

| Polymer ID | Mole % NVF | N-Vinylformamide (g) | N-Vinylpyrrolidone (g) | Vazo 56WSP (g) | Water (g) | dialyzed and lyophilized (g) | Weight of polymer isolated (g) |
|---|---|---|---|---|---|---|---|
| Polymer A | 100.00 | 15.000 | 0.000 | 0.250 | 72.180 | 5.290 | 0.771 |
| Polymer B | 50.00 | 5.852 | 9.144 | 0.192 | 53.380 | 4.570 | 0.920 |
| Polymer C | 5.00 | 0.490 | 14.511 | 0.165 | 42.350 | 3.830 | 1.120 |
| Polymer D | 0.00 | 0.000 | 15.000 | 0.161 | 41.350 | 3.770 | 1.060 |

B. Preparation of Polymers A10, A20, A50 and A100 (Varying Hydrolysis of pNVF)

Polymer solution A was treated with various amounts of NaOH and rotated in an oven at 80° C. overnight. This reaction is illustrated in equation I below.

Equation I

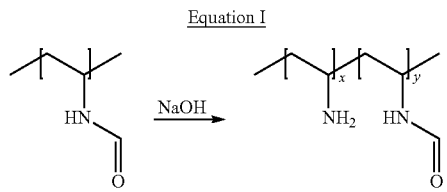

The polymer solutions were neutralized using HCl conc. (polymer A10 and Polymer A20 solutions adjusted to pH=9.0; polymer A50 and Polymer A100 solutions adjusted to pH=10.0), dialyzed, and lyophilized (as described above). Table 4 lists the reagents used and amounts.

TABLE 4

| Polymer (% hydrolysis; theory) | Weight of polymer solution A (g) | Polymer Weight (g calculated) | NVF (calculated meq) | NaOH solution (50%, g) | mEquiv of NaOH (calculated) | Lyophilized polymer weight (g) | % Hydrolysis (by NMR analysis) |
|---|---|---|---|---|---|---|---|
| Polymer A10 (10) | 20.4 | 3.5 | 31.5 | 0.252 | 3.15 | 1.07 | 3.3 |
| Polymer A20 (20) | 20.4 | 3.5 | 31.5 | 0.504 | 6.3 | 1.15 | 14.9 |
| Polymer A50 (50) | 20.4 | 3.5 | 31.5 | 1.26 | 15.75 | 1.18 | 43.3 |
| Polymer A100 (100) | 20.4 | 3.5 | 31.5 | 2.56 | 32 | 1.04 | 75.1 |

C. Preparation of Polymers E-J

A second series of co-polymers was made according to Table 5. In step 1 the monomers were placed in a bottle, sparged with nitrogen gas for 10 minutes, and rotated in an oven at the selected temperature for 14 hours. In step 2, each polymer solution in its entirety was diluted with water, treated with NaOH, and refluxed for at least 20 hours. The reaction for copolymers including N-vinyl formamide and N-vinyl pyrrolidone is illustrated in Equation II below.

TABLE 5

| | Step 1 Polymerization | | | | | | Step 2 Hydrolysis | |
|---|---|---|---|---|---|---|---|---|
| Polymer ID | Mole % NVF | N-Vinylformamide (g) | N-Vinylpyrrolidone (g) | Vazo 56WSP (g) | Water (ml) | Polymerization temperature (° C.) | Added water (ml) | Added 50% NaOH solution (g) |
| Polymer E | 100.00 | 15.000 | 0.000 | 0.244 | 72.18 | 70 | 428.0 | 33.76 |
| Polymer F | 80.00 | 10.785 | 4.215 | 0.223 | 63.51 | 55 | 475.7 | 24.30 |
| Polymer G | 60.00 | 7.346 | 7.653 | 0.199 | 56.46 | 55 | 483.5 | 16.50 |
| Polymer H | 40.00 | 4.482 | 10.515 | 0.183 | 50.65 | 55 | 489.9 | 10.10 |
| Polymer I | 20.00 | 2.064 | 12.931 | 0.168 | 45.60 | 55 | 495.3 | 4.70 |
| Polymer J | 10.00 | 1.000 | 14.000 | 0.162 | 43.40 | 70 | 457.0 | 2.24 |

Equation II

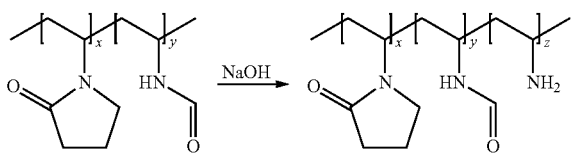

Each hydrolyzed polymer solution was difiltered using a 10 kDa membrane (0.10 m² pellicon mini cassette; available from Millipore; Billerica, Mass.) until the pH of the permeate was less than 7, which required about 15 to 20 liters of permeate.

Paclitaxel crystals were obtained by suspending paclitaxel (LC Laboratories; Woburnn, Mass.) in water at 50 mg/mL. The paclitaxel was micronized using a sonic probe for 30 seconds, and leaving the resulting suspension for three days at room temperature on an orbital shaker with a 1 hour sonication treatment per day in a sonic bath over the course of the three days ("Sonicated Paclitaxel"). The mixture was lyophilized.

Unless otherwise indicated nylon balloons (20×3.5 mm) were used in all studies.

Hydrophilic basecoats (R) were deposited onto the nylon balloon surfaces. The hydrophilic basecoat solution included 6.25 g/L polyvinyl pyrrolidone (PVP) with benzoylbenzoic acid groups; 1.25 g/L polyacrylamide; 2.5 g/L PVP (K90); and 0.05 g/L photo-crosslinker; in a solvent solution of 85:15 water/isopropanol. Crosslinkers were prepared as described in US Patent Application Publication 2012/0046384, Kurdyumov et al. After coating, the basecoat material was dried at room temperature for 15 minutes and then irradiated with UV light for 3 minutes.

Example 7

Paclitaxel (PTX) Adsorption from Suspensions—Comparison with Polymers with Pendent Primary Amines Half of the number of wells (columns 7-12) in Matrigel® coated 96-well plates (BD Biosciences) were seeded with human coronary artery endothelial cells (HCAEC)-(200 μL of 10⁵ cells/mL) and incubated at 37° C. for 24 hours.

Suspensions of 11 mg/mL paclitaxel crystals (prepared as described in patent '485 with sonication) in water with dissolved polymers at 1 mg/ml (92:8 ratio PTX/PEI), were prepared.

The following polymers were used:

TABLE 6

| Example | Polymer |
|---|---|
| CEx 1 | Branched poly(ethyleneimine) (PEI; 750 kDa; available from Polysciences) |
| CEx 2 | Branched poly(ethyleneimine) (PEI; 70 kDa; available from Polysciences) |
| Ex 1 | Poly(allylamine) (PAA; 25 kDa; available from Polysciences, Warrington, PA) |
| Ex 2 | 100% pNVF (poly(N-vinylformamide; Polymer A above) |
| Ex 3 | 50% poly(N-vinylformamide); (Polymer A50 above) |
| Ex 4 | 100% pNVA (Polymer A100 above; hydrolyzed poly(N-vinylformamide) |
| Ex 5 | PVP-co-pNVA 50:50 mol fraction ratio |

Figure 12:
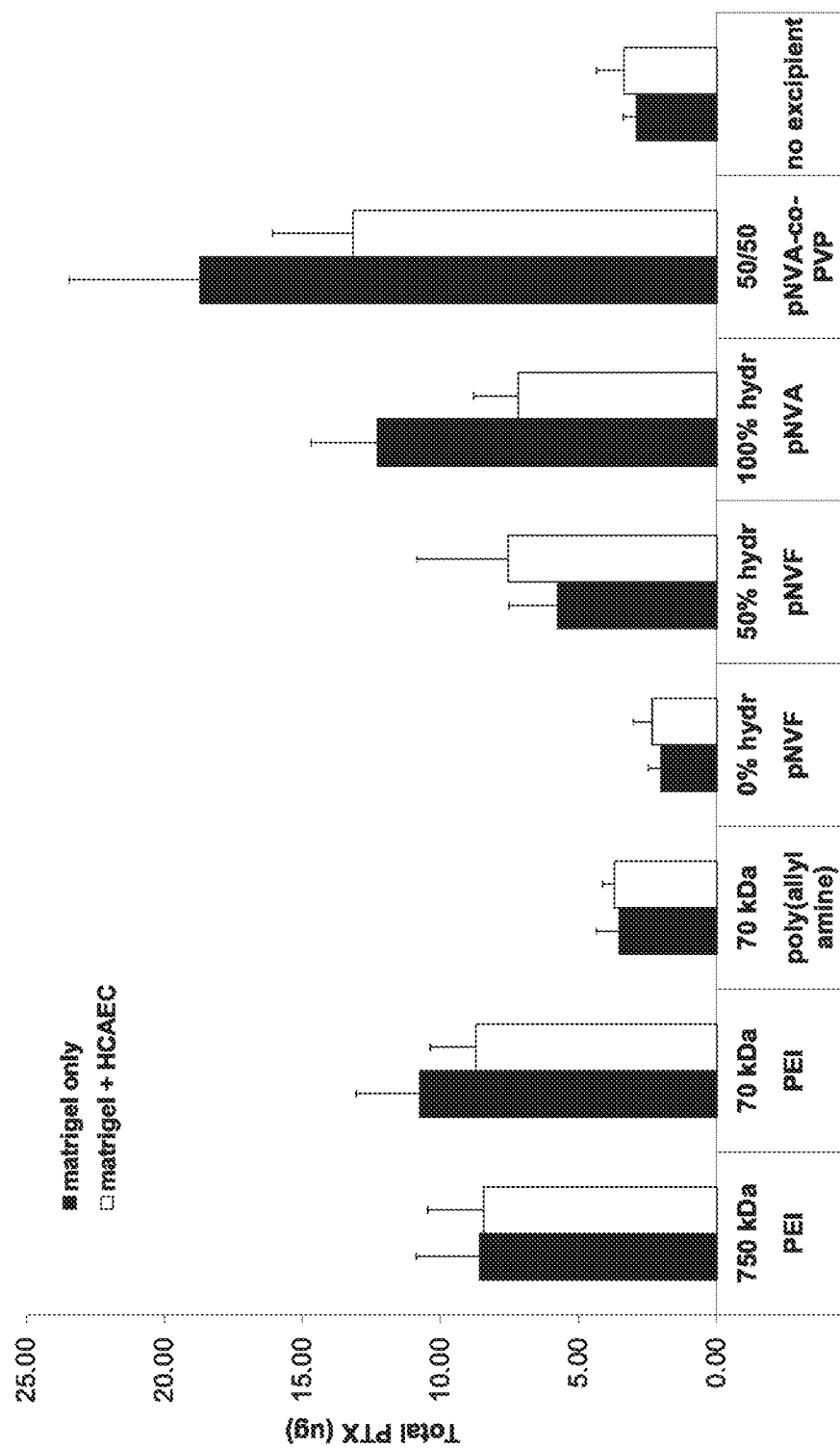
FIG. 12 is graph showing amounts of paclitaxel adsorbed to a matrigel surface comparing the effects of different excipients.

Each of the formulations (5 μL) in Table 6 above was pipetted in the 100 μL medium of 8 wells without cells and 8 wells with HCAEC (Human Coronary Artery Endothelial Cells; available from Lonza, Cologne, Germany) in the Matrigel™ (available from Becton, Dickinson and Company, Franklin Lakes, N.J.) coated well-plate and left for 3 minutes. Immediately upon completion of exposure time the wells were rinsed 3 times with 200 μL PBS. Adsorbed PTX was dissolved in MeOH/0.1% acetic acid (AcOH) and quantified by HPLC (see FIG. 12).

As noted above, various water-soluble poly-amines have been synthesized based on copolymerizing or polymerizing N-vinyl formamide (pNVF) and subsequent hydrolysis of the N-formamide group to obtain poly(N-vinyl amine) (pNVA) groups.

Example 8

Paclitaxel (PTX) Adsorption from Suspensions—Copolymers of PVP and Poly(N-Vinyl Amine): Polymers with Pendent Primary Amines Matrigel® coated 96-well plates (BD Biosciences) were used without seeding any cells on the surface. 100 µL cell medium was pipetted in the wells and the plate was warmed to 37° C. Suspensions of 11 mg/mL paclitaxel crystals (prepared as described in patent 485 with sonication) in water with dissolved polymers at 1 mg/ml (92:8 w/w ratio paclitaxel vs polymer) were prepared.
The following polymers were used:
 a. PVP-co-pNVA 20:80 mol fraction ratio
 b. PVP-co-pNVA 40:60 mol fraction ratio
 c. PVP-co-pNVA 50:50 mol fraction ratio
 d. PVP-co-pNVA 60:40 mol fraction ratio
 e. PVP-co-pNVA 80:20 mol fraction ratio
 f. 100% PVP (K90, BASF)
 g. 100% pNVA.

Per formulation 5 µL was pipetted in the 100 µL medium in 6 wells. Upon addition the plate was left for 3 minutes for the suspensions to settle. Immediately upon completion of exposure time the wells were rinsed 3 times with 200 µL PBS. Adsorbed PTX was dissolved in MeOH/0.1% v/v AcOH and quantified by HPLC Z-potential of the formulations were acquired using DLS (Malvern Zetasizer). All mixtures were diluted in DI water 500×.

Figure 13:
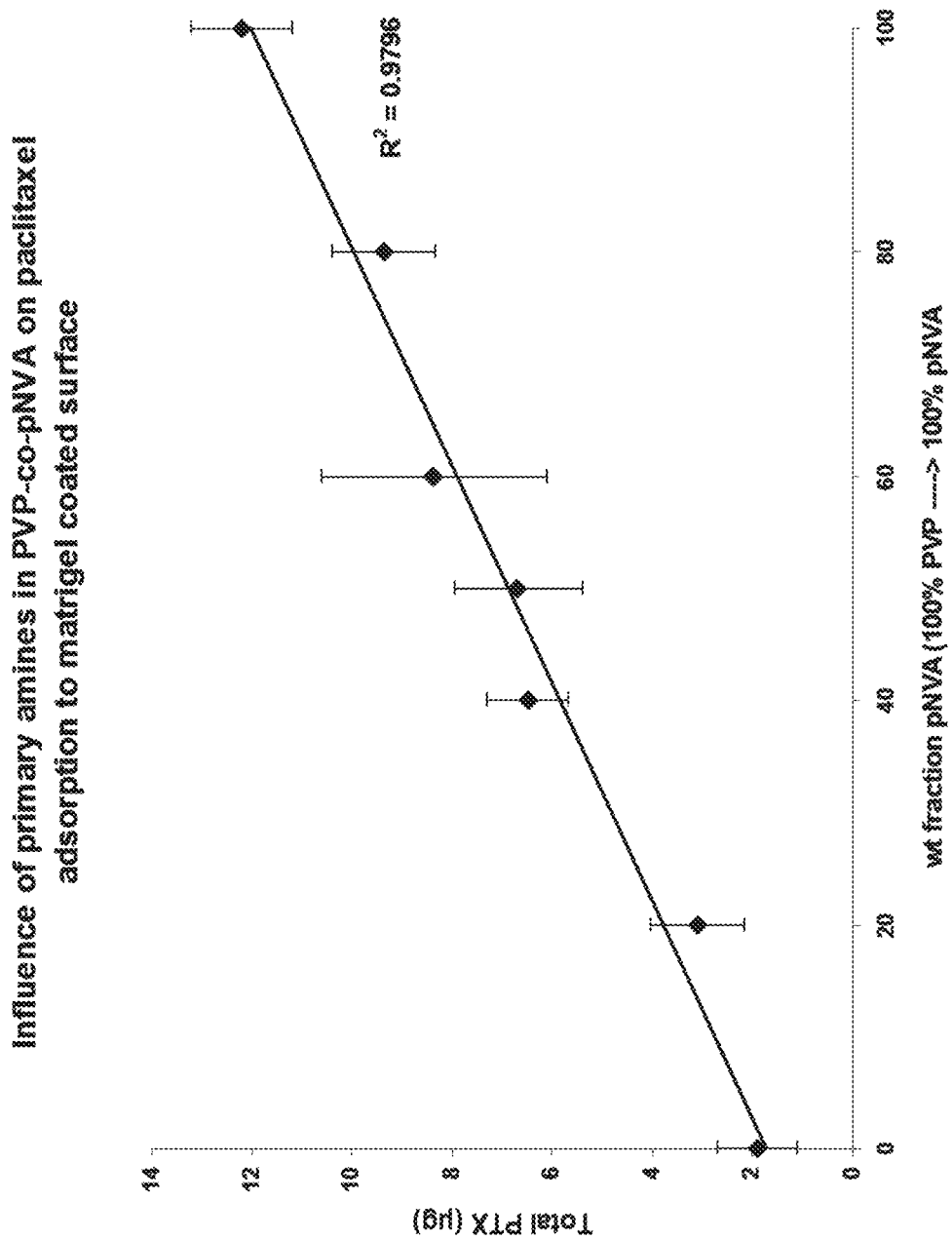
FIG. 13 is a graph showing amounts of paclitaxel adsorbed to a matrigel surface while varying the fractions of PVP and pNVA in a copolymer.
Figure 14:
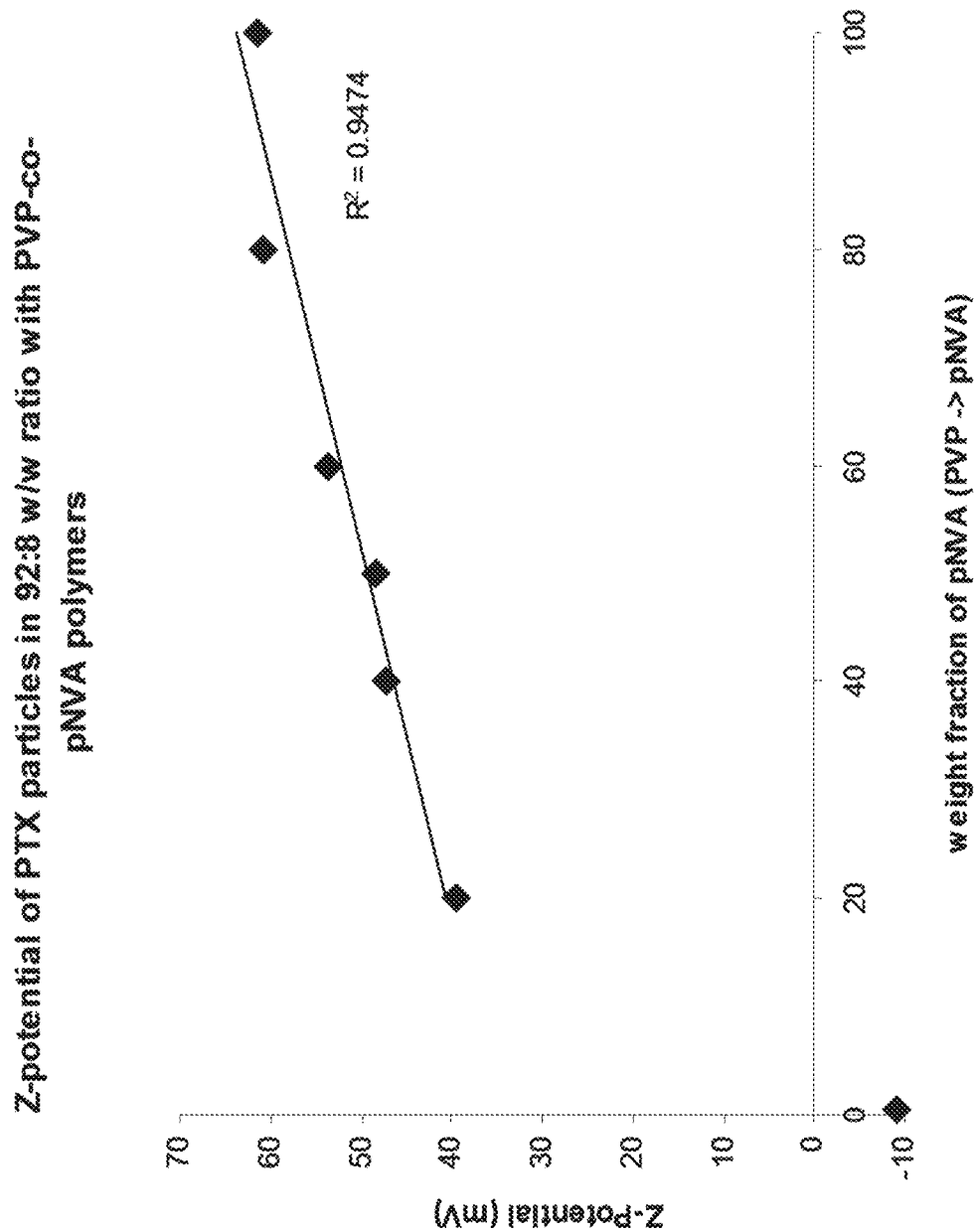
FIG. 14 is a graph showing the zeta potential (mV) of paclitaxel particles while varying the fractions of PVP and pNVA in a copolymer.

A linear correlation between the wt % of the pNVA fraction versus adhered paclitaxel was found ($r^2$=0.98) (see FIG. 13). A similar linear correlation was found between the wt % of the pNVA fraction versus the Zeta-potential of paclitaxel crystals (see FIG. 14).

Example 9

Ex-Vivo Testing with Rapamycin

In the experiments balloon stubbies (20 mm) were used that were coated as described above. Rapamycin (available from LC-Laboratories) was dissolved in acetone at 200 mg/mL. Twice one mL of the solution was pipetted quickly into 20 mL DI water while stirring. The mixture was left stirring for 30 minutes at room temp to allow the majority of acetone to evaporate. The mixture was then freeze-dried overnight.

The following coating solutions were prepared:
 a) Rapamycin solids at 50 mg/mL in water with 10 mg/mL PEI 750 kDa at pH 7
 b) Rapamycin solids at 50 mg/mL in water with 10 mg/mL poly(N-vinyl amine)
 c) Rapamycin solids at 50 mg/mL in water with 10 mg/mL 50/50 poly(PVP-co-N-vinyl amine)
 d) Rapamycin solids at 50 mg/mL in water (no excipient)

Figure 15:
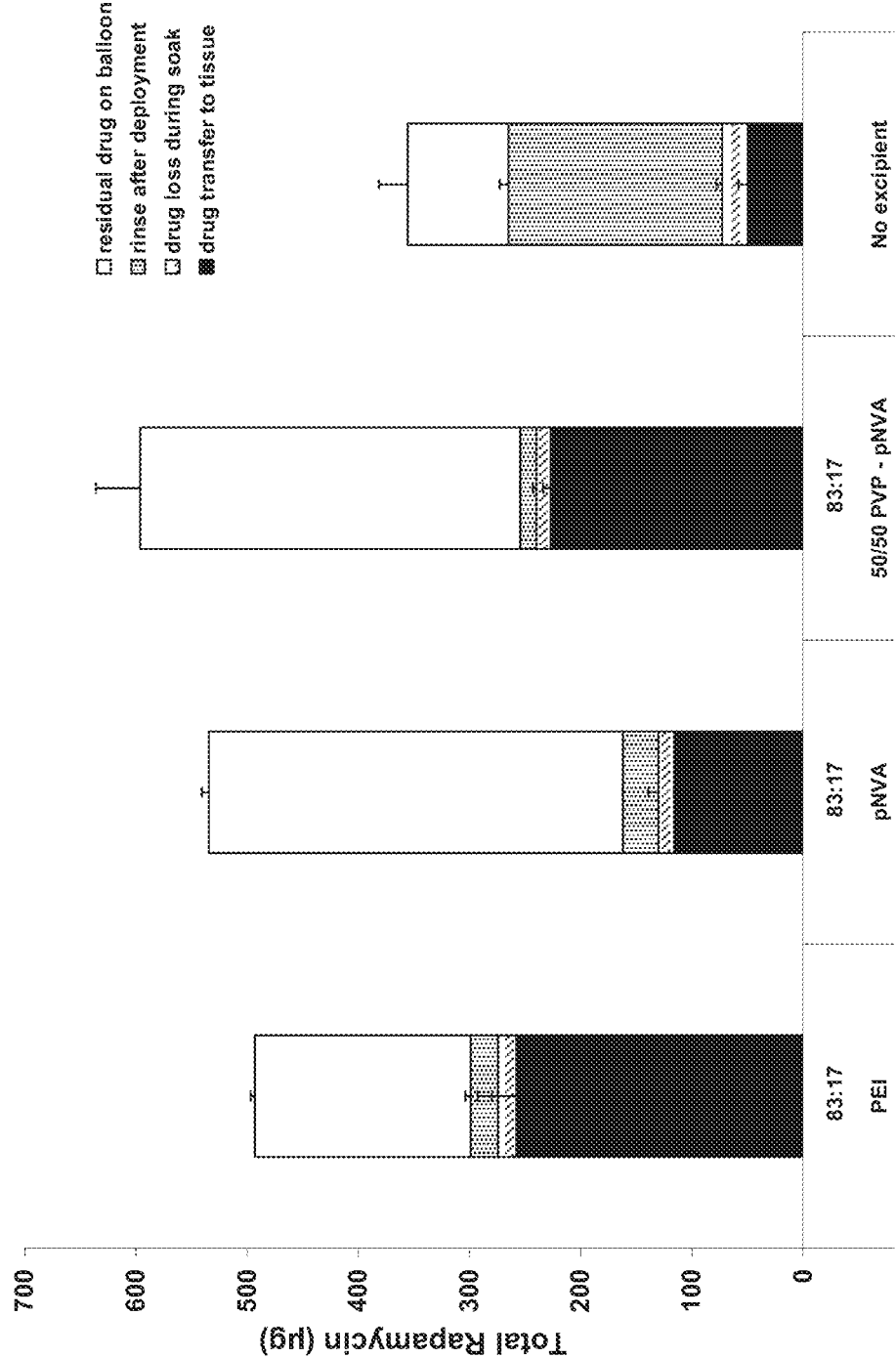
FIG. 15 is a graph showing disposition of rapamycin comparing the effects of different excipients.

HT-coated balloons received 14 µL of top-coat aiming for 700 µg (~3 µg/mm$^2$). The stubbies were dried overnight, pleated and folded and 'baked' for 1 hour at 50° C. and tested in excised arteries. PBS was used for the soaking of the stubbies for 30 seconds prior to expansion in arteries. PBS was used as medium for the arteries for subsequent inflation and rinsing. The results are shown in FIG. 15.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

In the Specification and claims, the term "about" is used to modify, for example, the quantity of an ingredient in a composition, concentration, volume, process temperature, process time, yield, flow rate, pressure, and like values, and ranges thereof, employed in describing the embodiments of the disclosure. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

All publications and patent applications in this specification are indicative of the level of ordinary skill in the art to which this invention pertains. All publications and patent applications are herein incorporated by reference to the same extent as if each individual publication or patent application was specifically and individually indicated by reference. To the extent inconsistencies arise between publications and patent applications incorporated by reference and the present disclosure, information in the present disclosure will govern.

The invention has been described with reference to various specific and preferred embodiments and techniques. However, it should be understood that many variations and modifications may be made while remaining within the spirit and scope of the invention.

What is claimed is:

1. A drug delivery device comprising:
 a substrate;
 an uncharged hydrophilic polymer layer disposed on the substrate, the uncharged hydrophilic polymer layer comprising a biostable synthetic hydrophilic polymer comprising one or more of acrylic monomers, vinyl monomers, and ether monomers; and
 a coated therapeutic agent particle layer disposed on the uncharged hydrophilic polymer layer, the coated therapeutic agent particle layer consisting of coated therapeutic agent particles comprising:

a particulate hydrophobic therapeutic agent; and
PVP-co-pNVA at a mol fraction of 20:80 PVP:pNVA to 80:20 PVP:pNVA; and
wherein the coated therapeutic agent particle layer is configured as an outermost layer of the drug delivery device for direct contact with an in vivo environment.

2. The drug delivery device of claim 1, the coated therapeutic agent particles exhibiting a Zeta potential of greater than +10 mV.

3. The drug delivery device of claim 1, the particulate hydrophobic therapeutic agent having an average diameter of between 100 nm and 10 μm.

4. The drug delivery device of claim 1, the particulate hydrophobic therapeutic agent having an average diameter of between 0.3 μm to about 1 μm.

5. The drug delivery device of claim 1, the particulate hydrophobic therapeutic agent selected from the group consisting of paclitaxel, sirolimus, and analogs thereof.

6. The drug delivery device of claim 1, the uncharged hydrophilic polymer layer covalently bonded to the substrate.

7. The drug delivery device of claim 1, the uncharged hydrophilic polymer layer cross-linked with a photoactivatable cross-linking agent.

8. The drug delivery device of claim 1, the device comprising a drug-containing balloon catheter.

9. A drug delivery coating comprising
a polymeric layer, the polymeric layer comprising an uncharged hydrophilic surface configured to be disposed on a substrate, the uncharged hydrophilic polymer layer comprising a biostable synthetic hydrophilic polymer comprising one or more of acrylic monomers, vinyl monomers, and ether monomers;
a coated therapeutic agent particle layer disposed on the hydrophilic surface, the coated therapeutic agent particle layer consisting of coated therapeutic agent particles comprising:
a particulate hydrophobic therapeutic agent core; and
PVP-co-pNVA at a mol fraction of 20:80 PVP:pNVA to 80:20 PVP:pNVA; and
wherein the coated therapeutic agent particle layer is configured as an outermost layer of the drug delivery device for direct contact with an in vivo environment.

10. A medical device comprising:
a capsule housing;
control circuitry disposed with in the capsule housing;
at least one moveable element operably connected to the capsule housing,
the moveable element comprising
a substrate and
a coating disposed on the substrate, the coating comprising;
an uncharged hydrophilic polymer layer disposed on the substrate, the uncharged hydrophilic polymer layer comprising a biostable synthetic hydrophilic polymer comprising one or more of acrylic monomers, vinyl monomers, and ether monomers; and
a coated therapeutic agent particle layer disposed on the hydrophilic polymer layer, the coated therapeutic agent particle layer consisting of coated therapeutic agent particles comprising:
a particulate hydrophobic therapeutic agent; and
PVP-co-pNVA at a mol fraction of 20:80 PVP:pNVA to 80:20 PVP:pNVA; and
wherein the coated therapeutic agent particle layer is configured as an outermost layer of the drug delivery device for direct contact with an in vivo environment.

11. The medical device of claim 10, the control circuitry configured to cause the moveable element to move between a deployed position and a non-deployed position; the medical device comprising a total width, wherein the total width of the medical device is greater in the deployed configuration than in the non-deployed configuration.

12. The drug delivery device of claim 1, further comprising PVP-co-pNVA at a mol fraction of 40:60 PVP:pNVA to 60:40 PVP:pNVA.

13. The drug delivery device of claim 1, further comprising PVP-co-pNVA at a mol fraction of 50:50 PVP:pNVA.

* * * * *